US009708593B2

(12) United States Patent
Hetzler et al.

(10) Patent No.: US 9,708,593 B2
(45) Date of Patent: Jul. 18, 2017

(54) OLEAGINOUS BACTERIAL CELLS AND METHODS FOR PRODUCING LIPIDS

(71) Applicant: Neste Oil Oyj, Espoo (FI)

(72) Inventors: Stephan Hetzler, Munster (DE); Stefan Uthoff, Munster (DE); Daniel Broker, Haltern am See (DE); Alexander Steinbuchel, Altenberge (DE); Perttu Koskinen, Helsinki (FI)

(73) Assignee: Neste Oyj, Espoo (FI)

( * ) Notice: Subject to any disclaimer, the term of this patent is extended or adjusted under 35 U.S.C. 154(b) by 0 days.

(21) Appl. No.: 14/646,986

(22) PCT Filed: Oct. 16, 2013

(86) PCT No.: PCT/FI2013/050989
§ 371 (c)(1),
(2) Date: May 22, 2015

(87) PCT Pub. No.: WO2014/080070
PCT Pub. Date: May 30, 2014

(65) Prior Publication Data
US 2015/0322417 A1 Nov. 12, 2015

Related U.S. Application Data

(63) Continuation-in-part of application No. PCT/FI2013/050727, filed on Jul. 2, 2013.

(60) Provisional application No. 61/729,807, filed on Nov. 26, 2012.

(30) Foreign Application Priority Data

Nov. 26, 2012 (EP) .................................... 12194227

(51) Int. Cl.
C12P 7/64 (2006.01)
C12N 1/20 (2006.01)
C12N 9/42 (2006.01)
C11B 1/02 (2006.01)

(52) U.S. Cl.
CPC ............ *C12N 9/2437* (2013.01); *C11B 1/025* (2013.01); *C12N 9/2434* (2013.01); *C12P 7/64* (2013.01); *C12P 7/6463* (2013.01); *C12Y 302/01004* (2013.01); *C12P 7/6409* (2013.01); *C12P 2203/00* (2013.01); *C12Y 302/01006* (2013.01); *C12Y 302/01008* (2013.01); *C12Y 302/01021* (2013.01); *C12Y 302/01074* (2013.01); *C12Y 302/01091* (2013.01); *Y02E 50/13* (2013.01)

(58) Field of Classification Search
CPC ............................. C12P 7/6463; C12N 9/2437
USPC ............................................. 435/134, 252.3
See application file for complete search history.

(56) References Cited

U.S. PATENT DOCUMENTS

| 9,096,859 B2 * | 8/2015 | Bokinsky ............... C12N 9/248 |
| 2012/0115195 A1 | 5/2012 | Keasling et al. |
| 2012/0190090 A1 * | 7/2012 | Bokinsky ............... C12N 9/248 435/160 |

FOREIGN PATENT DOCUMENTS

| WO | 2008006832 | | 1/2008 |
| WO | 2009035551 | A1 | 3/2009 |
| WO | 2010075529 | A2 | 7/2010 |
| WO | 2011100571 | | 8/2011 |
| WO | 2012085340 | A1 | 6/2012 |
| WO | 2012085346 | A1 | 6/2012 |

OTHER PUBLICATIONS

The written opinion of the International Searching Authority (Nov. 28, 2013).*
Alvarez, H.M. et al. Triacylglycerols in Prokaryotic Microorganisms. Appl Microbiol Biotechnol (2002) 60: 367-376.
Argyros, D.A. et al. High ethanol titers from cellulose by using metabolically engineered thermophilic, anaerobic microbes. Applied and Environmental Microbiology, Dec. 2011, vol. 77, No. 23, pp. 8288-8294.
Brigham, C. J. et al. Bacterial carbon storage to value added products. Journal of Microbial & Biochemical technology [online], 2011, S3:002 [retrieved on Sep. 20, 2013]. Retrieved from the Internet .URL: http://www.omicsonline.org/1948-5948/pdfdownload.php?download=JMBT-S3-002.pdf> from p. 6, left column, second paragraph to p. 10, left column, second paragraph.
Dashtban, M. et al. Fungal bioconversion of lignocellulosic residues; opportunities & perspectives. International Journal of Biological Sciences, Sep. 2009, vol. 5, No. 6, pp. 578-595.
Han, S. J. et al. Characterization of a bifunctional cellulase and its structural gene. The cel gene of *Bacillus* sp. D04 has exo-and endoglucanase activity. Journal of Biological Chemistry, Oct. 1995, vol. 270, No. 43, pp. 26012-26019.
Hetzler, S. et al. Establishment of cellobiose utilization for lipid production in Rhodococcus opacus PD630. Appled and Environmental Microbiology, May 2013, vol. 79, No. 9, pp. 3122-3125.
Hetzler, S. et al. Saccharification of cellulose by recombinant Rhodococcus opacus PD630 strains. Applied and Environmental Microbiology, Sep. 2013, vol. 79, No. 17, pp. 5159-5166.
Holder, J. Comparative and Functional Denomics of Rhodococcus Opacus PD630 for Biofuels Development. PLoS Genetics, Sep. 2011, vol. 7, Issue 9, pp. 1-18.

(Continued)

*Primary Examiner* — Tekchand Saidha
(74) *Attorney, Agent, or Firm* — Andrus Intellectual Property Law, LLP

(57) ABSTRACT

This invention relates to cells and methods for producing lipids using cellulosic carbon source. More specifically the invention relates to oleaginous bacterial cells, wherein genes encoding at least one cellulolytic activity has been introduced. This invention also relates to methods for lipid production by cultivating an oleaginous bacterial strain or strains capable of expressing one or more cellulolytic activity.

22 Claims, 17 Drawing Sheets

(56) References Cited

OTHER PUBLICATIONS

Hui, L., et al. Direct Microbial Conversion of Wheat Straw into Lipid by a Cellulolytic Fungus of Aspergillus Oryzae A-4 in Solid-state Fermentation. Bioresource Technology 101 (2010) 7556-7562.

Lai, X., et al. Cloning and Sequencing of a Cellobiose Phosphotransferase System Operon from Bacillus Stearothermophilus XL-65-6 and Functional Experession in *Escherichia Coli*. J. Bacteriol (1993) 175(20): 6441.

Li, Sijin, et al., Overcoming Glucose Repression in Mixed Sugar Fermentation by Co-Expressing a Cellobiose Transporter and a B-glucosidase in *Saccharomyces cerevisiae*. Molecular BioSystems (2010) 6: 2129-2132.

Xiong, X., et al. Engineering of a Xylose Metabolic Pathway in Rhodococcus Strains. Appl. Environ. Microbiol. 2012, 78 (16): 5483.

International Search Report for Application No. PCT/FI2013/050989, date of mailing Nov. 28, 2013.

Written Opinion for Application No. PCT/FI2013/050989, date of mailing Nov. 28, 2013.

International Preliminary Report on Patentability for Application No. PCT/FI2013/050989, date of mailing May 26, 2015.

Supplementary European Search Report for EP13856111 dated Apr. 14, 2016.

Brigham, C. J. et al. Bacterial carbon storage to value added products. Journal of Microbial & Biochemical technology [online], 2011, S3:002 [retrieved on Sep. 20, 2013]. Retrieved from the Internet .URL: http://www.pmicsonline.org/1948-5948/pdfdownload.php?download=JMBT-S3-002.pdf> from p. 6, left column, second paragraph to p. 10, left column, second paragraph.

UniProtKB-Q9LAV5 (Q9LAV5_THEFU), Beta-glucosidase, http://www.uniprot.org/uniprot/Q9LAV5 (Jan. 11, 2017).

UniProtKB-P50401 (GUXA_CELFA), Exoglucanase A, http://www.uniprot.org/uniprot/P50401 (Jan. 11, 2017).

UniProtKB-P07984 (GUNA_CELFI), Endoglucanase A, http://www.uniprot.org/uniprot/P07984 (Jan. 11, 2017).

UniProtKB-P26225 (GUNB_CELFI), Endoglucanase B, http://www.uniprot.org/uniprot/P26225 (Jan. 11, 2017).

UniProtKB-P14090 (GUNC_CELFA), Endoglucanase C, http://www.uniprot.org/uniprot/P14090 (Jan. 11, 2017).

UniProtKB-P07986 (GUX_CELFI), Exoglucanase/ xylanase, http://www.uniprot.org/uniprot/P07986 (Jan. 11, 2017).

Jonathan Caspi, et al., "Thermobifida fusca exoglucanase Cel6B is incompatible with the cellulosomal mode in contrast to endoglucanase Cel6A", Syst Sunth Biol (2010) 4: 193-201.

G. Andre, et al., "Computational and experimental studies of the catalytic mechanism of Thermobifida fusca cellulase Cel6A (E2)", Protein Engineering, Design and Selection, Oxford Academic (2003) 16 (2): 125-134.

Koning, et al., "Cellobiose uptake in the hyperthermophilic archaeon Pyrococcus furiosus is mediated by an inducible, high-affinity ABC transporter", Journal of Bacteriology, 183(7), 4979-4984. DOI: 10.1128/JB.183.17.4979.2001.

Written Description Training Materials, Revision 1, Mar. 25, 2008.

\* cited by examiner

OLEAGINOUS BACTERIAL CELLS AND METHODS FOR PRODUCING LIPIDS

CROSS REFERENCE TO RELATED APPLICATION

The present application is the U.S. national stage of International Application No. PCT/FI2013/050989, filed Oct. 16, 2013, which international application was published on May 30, 2014, as International Publication No. WO2014/080070, which application is a continuation-in-part of International Application No. PCT/FI2013/050727, filed Jul. 2, 2013, which international application was published on May 30, 2014, as International Publication No. WO/2014/080069, which application claims priority to U.S. Provisional Patent Application No. 61/729,807, filed Nov. 26, 2012, and European Patent Application No. 12194227.0, filed Nov. 26, 2012, the contents of which are incorporated herein by reference in their entireties.

The present invention relates to oleaginous bacterial cells and methods for producing lipids. More specifically, the invention relates to oleaginous bacterial cells that have been modified to be able to utilize cellulosic substrate or cellobiase as a carbon source and bacterial production of lipids using, at least partly, cellulosic material or cellobiose as carbon source.

BACKGROUND OF THE INVENTION

Lignocellulose is the most abundant biopolymer on earth. Lignocellulose is the major structural component of woody plants and non-woody plants such as grass or straw. Lignocellulosic biomass is a complex substrate in which crystalline cellulose is embedded within a matrix of hemicellulose and lignin. Lignocellulose represents approximately 90% of the dry weight of most plant material with cellulose typically making up between 20% to 50% of the dry weight of lingo-cellulose and hemicellulose typically making up between 20% and 40% of the dry weight of lignocellulose. Large amounts of lignocellulosic residues are produced through forestry, timber and pulp and paper industries and agricultural practices (straw, stover, bagasse, husk, chaff) and many agroindustries. Also municipal waste contain fractions that can be considered as lignocellulose residues, such as paper or cardboard waste, garden waste or waste wood from construction. Due to high abundance and low price lignocellulosic residues are preferred materials for production of biofuels or raw materials thereof, such as lipids. In addition, dedicated woody or herbaceous energy crops with biomass productivity have gained interest as biofuel use.

The production of biofuels, especially ethanol, from lignocellulosic materials by microbial fermentations has been studied extensively. The greatest challenge for utilization of lignocellulosics for microbiological production of biofuels or biofuel feedstocks lays in the complexity of the lignocellulose material and in its resistance to biodegradation. In lignocellulose, cellulose (20-50% of plant dry weight) fibers are embedded in covalently found matrix of hemicellulose (20-40%), pectin (2-20%) and lignin (5-20%) forming very resistant structure for biodegradation. Further, the sugar residues of hemicellulose contain a varying mixture of hexoses (e.g., glucose, mannose and galactose), and pentoses (e.g., xylose and arabinose) depending on the biomass.

Microorganism-based lipids (i.e. single cell oils) can be used as raw materials for production of biofuels such as biodiesel, renewable diesel or bio jet fuel.

The key steps in cellulose degradation and subsequent fermentation into biofuels include the saccharification of the polymeric substrate into simple sugars, usually mediated by the action of at least three enzymes (endoglucanase (E.C. 3.2.1.4), exoglucanase (E.C. 3.2.1.91) and β-glucosidase (E.C. 3.2.1.21)) that act in a synergistic manner. These enzymes are usually produced in a dedicated process, representing major expense factor in lignocellulose-based biofuel processes. Simultaneous saccharification and fermentation (SSF) by a single microorganism, also known as consolidated bioprocessing (CBP), is regarded as potential alternative to the dedicated enzyme production by combining both saccharification and biofuel production. Consolidated bioprocessing offers the potential for lower cost and higher efficiency than processes featuring dedicated cellulase production. This can result in avoided costs of capital, substrate and other raw materials, and utilities associated with cellulase production. However, several challenges must be overcome to achieve economically viable production processes, and the maybe most important aspect, given that lipid-producing (oleaginous) organisms are used, is the large quantity of enzyme needed for the efficient hydrolyzation of cellulose, which can be achieved e.g. by genetic engineering. A recent investigation reported on engineered *Escherichia coli* strains, which were engineered to utilize pretreated lignocellulosic substrates to produce biodiesel, butanol and pinene (Bokinsky et al., 2011).

*Rhodococcus opacus* strain PD630 is the model oleaginous prokaryote regarding accumulation and biosynthesis of lipids, which serve as carbon and energy storage and can account up to 87% of the cell dry mass in this strain. In wild-type *R. opacus* PD630 the lipids consist mainly of triacylglycerols and are stored intracellularly. *R. opacus* has been considered as production strain for triacylglycerols (TAGs) from renewable resources for the production of biodiesel, monoalkyl esters of short chain alcohols and long chain fatty acids, due to its high substrate tolerance, high density culturing and rapid growth, which make it favorable over other production organisms. Unfortunately, in contrast to other *Rhodococcus* strains like *R. erythropolis*, *R. opacus* PD630 does not use cellobiose (1,4-β-D-glucopyranosyl-D-glucopyranose), the main product of extracellular bacterial and fungal cellulases, as sole carbon and energy source. Genetic analysis suggested that this inability is caused by the lack of a β-glucosidase, rendering the strain unable to hydrolyze cellobiose into its glucose monomers.

WO2011/163348 discloses an integrated suite of process to make jet fuel from wood. Publication proposes [paragraph 0037] that tri-acylglycerol could be produced by fermenting cellulose or hemicellulose from wood with lipid accumulating microbes such as algae or bacteria. However, none of the disclosed embodiments uses cellulosic substrates as a carbon source in fermentation.

Production of oil from lignocellulosic residue materials by microorganisms is attractive from sustainability point-of-view. Although lignocellulose is the most abundant plant material resource, its usability has been curtailed by its rigid structure. In addition to effective pretreatment also reasonably costly enzymatic hydrolysis is required before oleaginous cells could utilize cellulosic substrates. Thus there is a need for oleaginous bacterial strains that could utilize cellulosic substrate at least to some extent. There is also a need for methods of producing lipids on cellulosic substrate. This invention meets these needs.

SUMMARY OF THE INVENTION

An aim of this invention is to provide means for lipid production using renewable low cost substrate, especially cellulosic substrate.

First object of the present invention is an oleaginous bacterial cell. Characteristics of said cell are defined in claim 1.

Second object of the present invention is a method for lipid production from cellulosic materials by bacterial cells. Characteristic features of said method are defined in claim 8.

Third object of the present invention is an oleaginous bacterial cell. Characteristics of said cell are defined in claim 16.

Fourth object of the present invention is a method for lipid production from cellobiose materials by bacterial cells. Characteristic features of said method are defined in claim 17.

Fifth object of the invention is a method of producing lipids. According to the invention said method comprises cultivating cells according to this invention.

To achieve these objects the invention is characterized by the features that are enlisted in the independent claims. Other claims represent the preferred embodiments of the invention.

The invention allows consolidated bioprocessing of cellulosic materials for production of single cell oil for biofuels. It omits or decreases the use of externally produced enzymes and can result in significant improvements in cost-efficiency.

BRIEF DESCRIPTION OF THE DRAWINGS

FIG. 12. Physical maps of the constructed plasmid pEC-K18mob2::cel6a

YP_288996 and YP_288997) and bglC encoding a cytoplasmic β-glucosidase, (accession no. YP_288998) from *T. fusca*.

Figure 19:
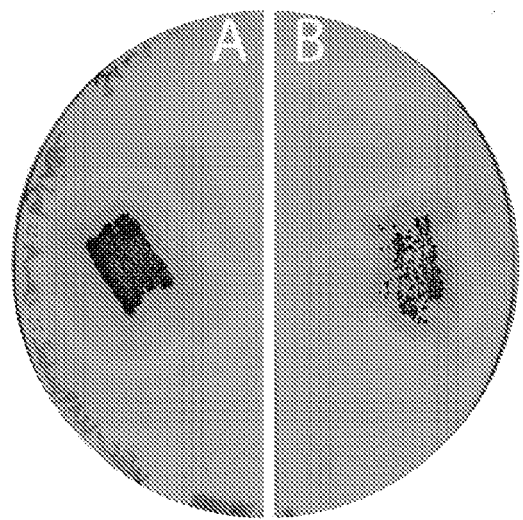

FIG. 19. Qualitative endocellulase enzyme assay. Recombinant strains of *R. opacus* PD630 were transferred onto MSM plates containing 0.5% (wt/vol) carboxymethylcellulose plus 0.5% (wt/vol) glucose as carbon source and 50 μg×mL$^{-1}$ kanamycin. Plates were stained with 0.1% (wt/vol) Congo Red and destained with 1 M NaCl after 2 days of incubation at 30° C. (A) *R. opacus* pEC-K18mob2::cenA::bglABC (B) *R. opacus* pCelluloseCB.

Figure 20:
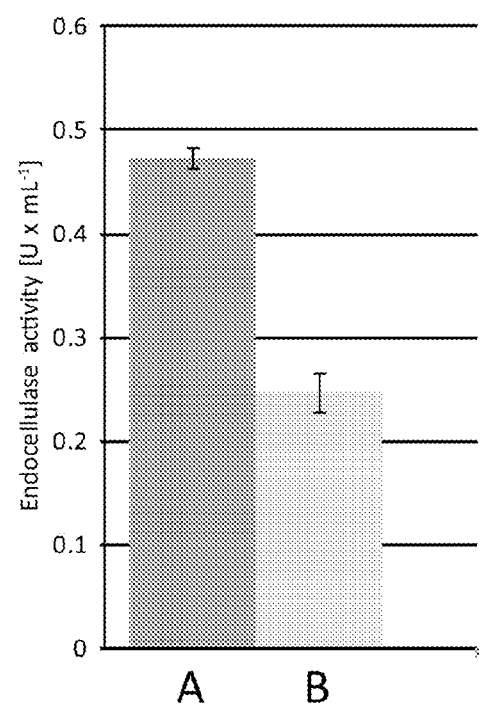

FIG. 20. Endocellulase activity in the culture medium determined for recombinant *R. opacus* PD630. Activity was determined with Azo-CMC (Megazyme, Ireland) at 30° C. (A) *R. opacus* pCelluloseCB; (B) *R. opacus* pEC-K18mob2::cenA::bglABC.

Figure 21:
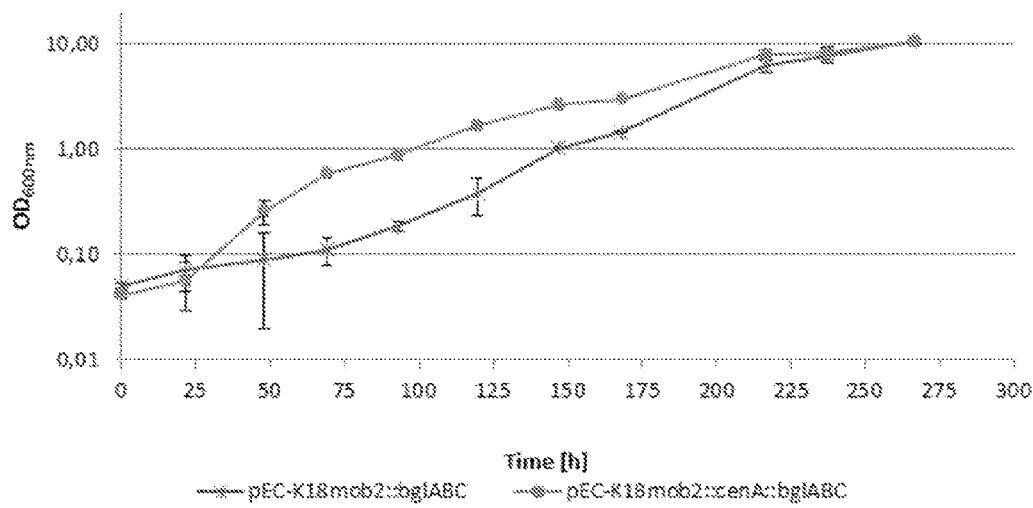

FIG. 21. Growth of the recombinant strains *R. opacus* PD630 pEC-K18mob2::bglABC and *R. opacus* PD630 pEC-K18mob2::cenA::bglABC in presence of cellobiose as sole carbon and energy source. Cells were cultivated in liquid MSM containing 1.3% (wt/vol) cellobiose. Error bars indicate standard deviation of triplicate measurements.

Figure 22:
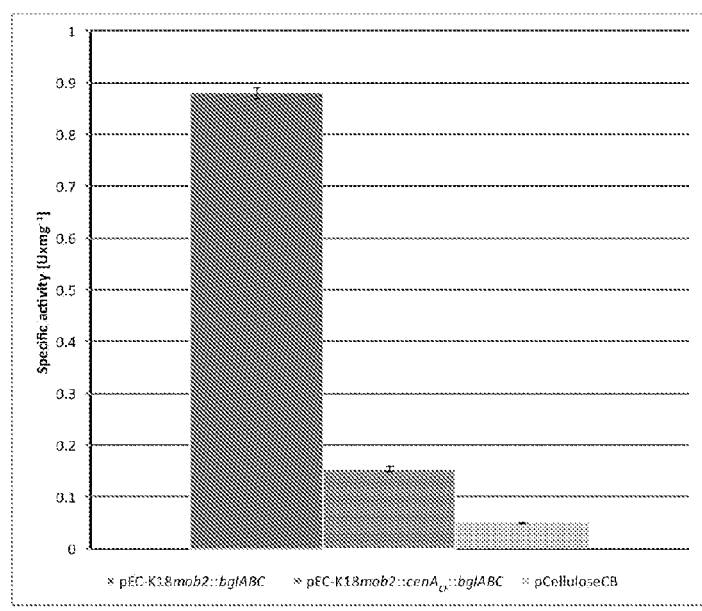

FIG. 22. Specific activity of the β-glucosidase BglC in the soluble protein fractions of recombinant *R. opacus* PD630. Activity was determined with pNPG according to Adin et al. 2008 at 30° C.

Figure 23:
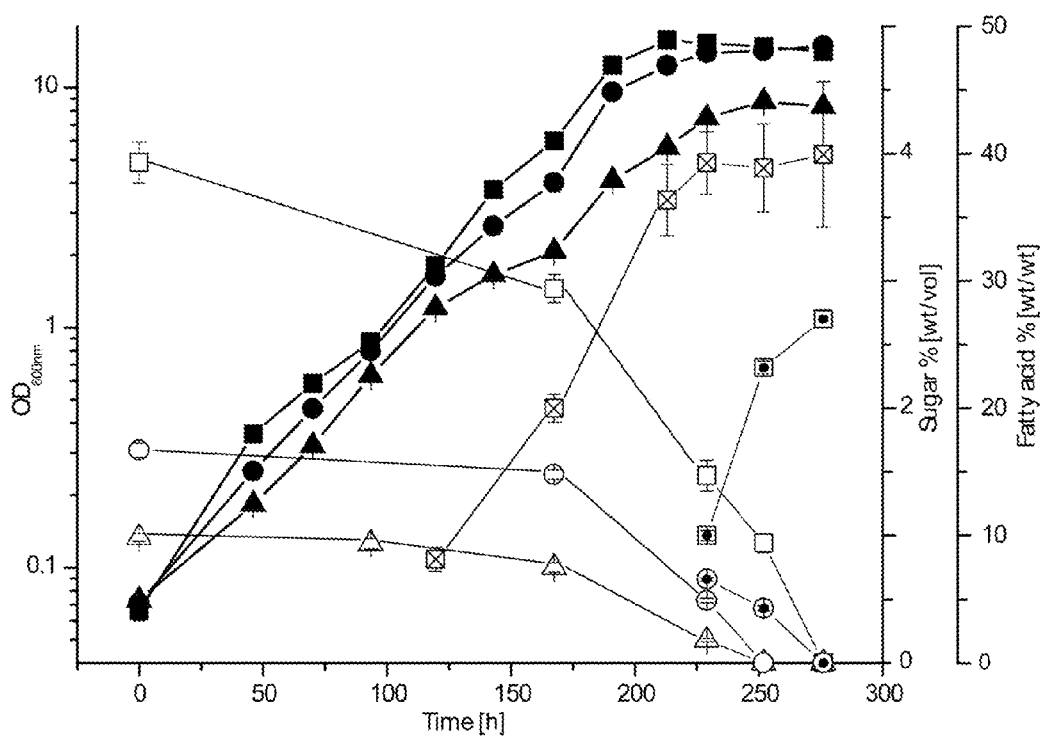

FIG. 23. Growth of the recombinant strain *R. opacus* PD630 pEC-K18mob2::bglABC in presence of different cellobiose concentrations. Cells were cultivated in liquid MSM containing 0.8, 1.5 or 4% (wt/vol) cellobiose as sole carbon source: ▲ 1% (wt/vol) cellobiose, ● 1.7% (wt/vol) cellobiose, ■ 4% (wt/vol) cellobiose. Cellobiose concentrations in the medium: Δ 1% (wt/vol) culture, ○ 1.7% (wt/vol) culture, □ 4% (wt/vol) culture. Glucose concentrations in the medium: 1.7% (wt/vol) culture; 4% (wt/vol) culture. Fatty acid content: 4% (wt/vol) culture. Error bars indicate standard deviations of triplicate measurements.

DETAILED DESCRIPTION OF THE INVENTION

An aim of the present invention is to establish a bacterial strain and a method for the production of lipids/fatty acids using a carbon source that is at least partially in cellulosic form. The inventors have surprisingly found that it is possible to modify oleaginous bacterial cells so that they can utilize cellulosic carbon source or cellobiose in lipid production. This results that easily available and renewable cellulosic materials can be used as a carbon source in lipid production without expensive separate hydrolysis to disaccharides and monosaccharides typically utilized by bacterial cells accumulating lipids.

"An oleaginous bacterial cell" refers here to a bacterial cell which accumulates at least 10% (w/w) of their biomass dry weight as lipids when cultivated in conditions optimal for lipid production. Preferably oleaginous bacterial cell accumulates at least 15%, more preferably at least 20%, even more preferably at least 30%, at least 40%, at least 50% and most preferably at least 60% (w/w) of their biomass as lipid.

In this connection terms "cellulosic material" or "cellulosic biomass" refer to biomass that is composed of cellulose and optionally other fractions such as hemicellulose, and lignin. Lignocellulose is the most common form of cellulosic material in the nature. Cellulosic material may also contain starch or other sugars in addition to cellulose and lignin.

The present invention provides an oleaginous bacterial cell wherein genes encoding at least one endocellulase, exocellulase and cellobiase activity operably linked to a suitable promoter sequence have been introduced. An advantage of such cells is the ability to benefit cellulosic carbon source in lipid production.

In other words said oleaginous cell is genetically modified to express also cellulolytic activities. "A cell genetically modified to express cellulolytic activities" means that said cell is genetically modified to express increased amounts of cellulolytic activities for hydrolysing cellulosic material to cellobiose (disaccharide) or cellobiose to monosaccharides or both, when compared to cell that is not modified to express cellulolytic activities. Preferably the organism expresses cellulolytic activities in sufficient amount for hydrolysing cellulosic material to disaccharides or monosaccharides that can be used as a carbon source in lipid production.

Some oleaginous bacterial cells are able to utilise disaccharides (of cellulose) without genetic modification. In such case the cell is able to utilize cellulolytic substrate after introducing genes encoding endocellulase and exocellulase activities.

Usually the cell is modified to express cellulolytic activities (or a cellulolytic activity) by introducing genes encoding polypeptides having said activity and suitable regulatory elements. Common way of introducing genes to a cell is transformation using methods known in the art. Stable transformation is preferred allowing culturing without selection pressure and facilitating large scale cultivation. As used herein, the term "stable transformation" refers to a cell carrying an inserted exogenous nucleic acid molecule which is capable of replication either as an autonomously replicating plasmid or as part of the host chromosome. Thus, all bacterial cells modified according to this invention are recombinant cells.

Preferably the cell is transformed using exogenous genes encoding cellulolytic activities. In this connection term exogenous means genes obtained from other bacterial strain or from completely other organism. Regulatory elements can be selected by known methods. Genes derived from the same species are deemed endogenous genes.

Cellulolytic activities hydrolyse cellulose to monosaccharides in synergistic manner. Endocellulases are enzymes having activity on internal bonds of cellulose. Endoglucanases (EC 3.2.1.4) are an example of endocellulases and hydrolyse internal glycosidic bonds of the cellulose chain. Exoglucanases (EC 3.2.1.91) are exocellulases and hydrolyse cellulose from the end of the glucose chain and produce mainly cellobiose. Cellobiases i.e. beta-glucosidases (EC 3.2.1.21) hydrolyze soluble oligosaccharides including cellobiose to glucose. A skilled man is aware that also several enzymes belonging to other EC-classes exhibit activity on cellulose; examples of such enzymes are beta-glucanases and hemicellulases.

Some oleaginous bacterial cells, such as *R. opacus* (PD630) used in experimental part of this application, are not able to utilize cellobiose. Thus, in on embodiment the oleaginous bacterial cell expressing one or more cellulolytic activities further comprises genes encoding sugar transporter system capable of cellobiose intake. Said transporter enables the intake of disaccharides that are then hydrolyzed to monosaccharides and used as a carbon source.

According to one embodiment the transporter is ABC type-transporter. In one embodiment the transporter is BglA (SEQ ID NO: 13) or BglB (SEQ ID NO: 15) having an amino acid sequence shown as SEQ ID NOs: 13 and 15, respectively, or sequence having at least 80%, preferably at least 90% and most preferably at least 95% identity to SEQ ID NO: 13 or SEQ ID NO: 15. BglA and BglB are encoded by sequences shown as SEQ ID NOs: 14 and 16, respectively.

According to one other embodiment the oleaginous bacterial cell expressing one or more cellulolytic activities is capable of secreting cellobiase activity. This may result from modified gene encoding said activity or from introducing means for expressing suitable secretion system to said cell. One embodiment of the invention is to introduce means for cellobiase expression and secretion to oleaginous bacterial cells already modified to express endo- and exoglucanase activities. Still further embodiment is to supplement the culturing media of oleaginous bacterial cell according to the invention with external cellobiase activity. Also other supplemental cellulolytic activities can be added, when necessary.

The term "operably linked" refers to a relationship between two nucleic acid sequences wherein the expression of one of the nucleic acid sequences is controlled by, regulated by or modulated by the other nucleic acid sequence.

The term "promoter" refers to a polynucleotide that regulates expression of a selected polynucleotide sequence operably linked to the promoter, and which effects expression of the selected polynucleotide sequence.

In one embodiment of the invention at least one endocellulase activity is selected from the group of
(a) endoglucanases, beta-glucanases and xylanases; and
(b) enzymes belonging to class EC 3.2.1.4, EC 3.2.1.6 and EC 3.2.1.8; and
(c) a polypeptide having cellulolytic activity and comprising an amino acid sequence having at least 70%, preferably at least 80%, more preferably at least 90%, still more preferably at least 95% and most preferably at least 98% identity to polypeptide having SEQ ID NO: 1 (CenA), SEQ ID NO: 3 (CenB), SEQ ID NO: 5 (CenC) or SEQ ID NO: 11 (Cel6A); or a polypeptide encoded by a nucleotide having SEQ ID NO: 2 (cenA), SEQ ID NO: 4 (cenB), SEQ ID NO: 6 (cenC) or SEQ ID NO: 12 (cel6A) or a complementary strand thereof; and
(d) any combination thereof.

In one embodiment of the invention at least one exocellulase activity is selected from the group of
(a) cellulose 1,4-β-cellobiosidases and 1,4-beta-glucan cellobiohydrolases; and
(b) enzymes belonging to class EC 3.2.1.91 or EC 3.2.1.74; and
(c) a polypeptide having cellulolytic activity and comprising an amino acid sequence having at least 70%, preferably at least 80%, more preferably at least 90%, still more preferably at least 95% and most preferably at least 98% identity to polypeptide having SEQ ID NO: 9 (Cex) or SEQ ID NO: 7 (CbhA); or a polypeptide encoded by a nucleotide having SEQ ID NO: 10 (cex) or SEQ ID NO: 8 (cbhA) or a complementary strand thereof; and
(d) any combination thereof.

In one embodiment of the invention at least one cellobiase activity is selected from the group of
(a) cellobiases and beta-glucosidases and beta-galactosidase; and
(b) enzymes belonging to class EC 3.2.1.21; and
(c) a polypeptide having cellulolytic activity comprising an amino acid sequence having at least 70%, preferably at least 80%, more preferably at least 90%, still more preferably at least 95% and most preferably at least 98% identity to polypeptide having SEQ ID NO: 17 (BglC); or a polypeptide encoded by a nucleotide having SEQ ID NO: 18 (bglC) or a complementary strand thereof; and
(d) any combination thereof.

In one embodiment the cellulolytic activities are selected from the group consisting of cenA, cenB, cenC, cex and cbhA of *Cellulomonas fimi* having accession number ATCC484 and cel6A of Thermobifida *fusca* having accession number DSM43792.

In one preferred embodiment of the invention the oleaginous bacterial cell belongs to genus *Rhodococcus*, preferably to species *Rhodococcus opacus*. One preferred embodiment is *Rhodococcus opacus* strain PD630 used also in experimental part of this application. *Rhodococcus opacus* has very high capacity of lipid production.

According to one embodiment the lipid pathway of oleaginous bacterial cell of the invention is modified in order to enhance lipid production, to alter fatty acid profile and/or to produce fatty acid derivatives. Any modifications known in the art can be used. Enhanced lipid production will improve the process yield and economy.

According to one preferred embodiment the oleaginous bacterial cell of the invention accumulates at least 15%, more preferably at least 20%, even more preferably at least 30%, at least 40%, at least 50% and most preferably at least 60% (w/w) of their biomass dry weight as lipid when cultivated in conditions suitable or optimal for lipid production.

The present invention also provides a method for lipid production comprising the steps of
(a) providing a culturing medium where at least part of the carbon source is in cellulosic form; and
(b) providing a bacterial strain capable of expressing and secreting one or more cellulolytic activity/cellulolytic activities; and
(c) contacting said medium and said strain; and
(d) cultivating said medium and said strain in conditions allowing expression of said cellulolytic activities; and
(e) providing (i) the cellulolytic bacterial strain of (b) being oleaginous, or (ii) another oleaginous bacterial strain genetically modified to use cellobiose as a carbon source; and
(f) contacting the culturing medium of step (c) or the spent culturing medium obtained from step (c) with said strain; and
(g) cultivating the strain in conditions allowing the lipid production; and (h) recovering the lipids.

Method of the invention allows using cellulosic material in lipid production without separate cellulose hydrolysis to sugars. Bacterial strain is a population of bacterial cells descending from a single bacterial cell or pure culture.

In one embodiment the bacterial strains are cultivated sequentially. The bacterial strain capable of expressing and secreting one or more cellulolytic activity are separated from the spent culturing medium before contacting said culturing medium with oleaginous strain. After removing the cells the spent culturing medium is transferred to another cultivation vessel (fermentor) for contacting with oleaginous strain. Preferably the cellulosic substrate is essentially hydrolysed to disaccharides (such as cellobiose) or monosaccharides during the first cultivation step.

In another embodiment the oleaginous strain is contacted with spent culturing medium containing the cells capable of expressing cellulolytic activity. In one embodiment the degradation of the cellulosic substrate is continued when the oleaginous bacterial strain is contacted with the culturing media.

The skilled man understands that when two separate strain (i.e. first cell capable of expressing and secreting one or more cellulolytic activity and a second oleaginous cell) are cultivated sequentially it may be necessary to adjust cultivation conditions (such as nutrients, pH, temperature, aeration) that are suitable for expression of the desired genes for each cultivation step.

In one embodiment the bacterial strain secreting cellulolytic activity and the oleaginous strain are cultivated simultaneously in the same culturing medium.

In this connection "a culturing medium" refers here to a medium used for cultivating microorganisms, in particular bacteria. The culturing medium contains a carbon source and a nitrogen source and may be supplemented with minerals, micronutrients, macronutrients, growth factors and buffering agents. At the beginning of the cultivation at least part of the carbon source is in cellulosic form (to be hydrolysed during cultivation). In another embodiment part of the carbon source contains cellobiose. A phrase "a culturing medium where at least part of the carbon source is in cellulosic form" means that at least 10% (w/w), preferably at least 30%, more preferably at least 50%, still more preferably at least 60% and most preferably at least 80% of the carbon source is in cellulosic form. Term "cellulosic form" means that cellulose is in oligomeric or polymeric form containing at least 10 subunits. Preferably cellulosic material is separated at least partly from hemicellulose fraction in order to enhance availability to cellulolytic activities.

Term "cellulolytic activity" means any hydrolytic activity towards cellulose and/or its degradation products. Especially it means endo- and exoglucanase activities (so called major cellulases) and cellobiase activity and combinations thereof.

Conditions allowing lipid production refers to cultivation conditions where microorganisms can produce at least 10% of lipids from their dry cell weight.

Conditions allowing expression of said cellulolytic activities refers to cultivation conditions where microorganism produces cellulolytic activities, preferably in amount that is sufficient for hydrolysis of cellulolytic carbon source to cellobiose or cellobiose to monosaccharides, or both.

The term "lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as triacylglycerols, diacylglycerols, or monoacylglycerols. Preferred lipids in the present invention are fats, oils, waxes, acylglycerols and fatty acids and their derivatives, in particular triacylglycerols and wax esters.

The term "acylglycerol" refers to an ester of glycerol and fatty acids. Acylglycerols occur naturally as fats and fatty oils. Examples of acylglycerols include triacylglycerols (TAGs, triglycerides), diacylglycerols (diglycerides) and monoacylglycerols (monoglycerides).

"Oil recovery" or "Lipid recovery" refers to a process, in which the lipid (intracellular lipid) is recovered by mechanical, chemical, thermomechanical and/or autocatalytic methods or by a combination of these methods from the microorganism cells. In certain embodiments lipids can also occur extracellularly and in these cases oil recovery refers to a process, in which the lipids are recovered from spent culture medium by mechanical, chemical and/or thermomechanical methods.

According to one embodiment the bacterial strain capable of expressing and secreting one or more cellulolytic activity/cellulolytic activities secretes endoglucanase and exoglucanase activities and oleaginous strain expresses, in addition to lipid pathway, also cellobiase activity. Endo- and exocellulase activities hydrolyse cellulose to oligomers and to disaccharides as described before. Cellobiase activity hydrolyses disaccharides to monosaccharides.

Cellobiase activity can be secreted or cellobiose can be taken into the cell for hydrolysis. According to one embodiment the oleaginous cell according to step (e) further expresses transporters for cellobiose intake.

In the preferred embodiment the bacterial cell expressing and secreting cellulolytic activity (cellulolytic activities) is the oleaginous cell. In other words the bacterial strain is capable of secreting cellulosic activity and producing lipids from cellulosic sugars i.e. single strain is capable of producing lipids from the raw materials in cellulosic form. Utilization of a single strain allows in principle more simple and efficient operation of the bioprocess since cultivation conditions can be optimized for single strain.

In one embodiment the culturing medium is further supplemented with one or more cellulolytic activity or pretreated with an organism (e.g. fungi or bacteria) secreting high amounts of cellulolytic activities.

In one embodiment at least 10%, preferably at least 20%, at least 30%, at least 40%, at least 50%, more preferably 60 to 100%, and most preferably 80 to 100% of the carbon source is in cellulosic form.

In a preferred embodiment the carbon source is pretreated cellulose. An effective pretreatment can liberate the cellulose from the lignin seal and/or open the cellulose (crystalline) structure so as to render it accessible for a subsequent hydrolysis step by cellulolytic activities. Pretreatment can be done using the methods known in the art, e.g. strong acid hydrolysis, mild acid hydrolysis, steam explosion, ammonia fiber expansion, alkaline treatment, organosolve methods (use of solvents, such as ethanol etc. or organic acids), ionic liquids, thermochemical methods, sulfite pretreatment to overcome recalcitrance of lignocellulose (SPORL), alkaline wet oxidation and ozone pretreatment. Cellulose of plant material without any pretreatment is poorly accessible to enzymatic activities. The lignocellulose material may be (thermo)mechanically treated, e.g. particle size reduced with any methods, such as, but not limited to, crushing or milling, prior to or in between of pre-treatment.

According to one embodiment of the invention the cellulose fraction of the cellulosic material is at least partly separated from lignocellulose or lignocellulose structure is treated in such a way that cellulose fraction in lignocellulose has become more accessible to enzymatic activities compared to its natural state.

Preferably the oleaginous cell according to the invention utilizes cellulosic material as the main carbon source for growth and oil production.

This invention is also directed to an oleaginous bacterial cell, specifically *Rhodococcus*, preferably *Rhodococcus opacus* and more preferably *Rhodococcus opacus* PD630 cell, wherein a gene(s) encoding at least one cellobiase activity operably linked to a suitable promoter sequence has been introduced. According to preferred embodiment also a gene(s) encoding cellobiose sugar transporter(s) operably linked to a suitable promoter sequence has been introduced into said cell. Suitable activities and transporters have been discussed above. Such cell can produce lipids using cellobiase as a carbon source.

This invention is also directed to a method for lipid production comprising the steps of
  (a) contacting the cells of an oleaginous bacterial strain capable of expressing at least one cellobiase activity and optionally cellobiose transporter(s) with a culture medium wherein at least part of the carbon source is cellobiose, preferably cellobiose from hydrolysis of cellulosic substrate; and
  (b) cultivating the cells of said bacterial strain in conditions allowing the lipid production; and
  (c) recovering the lipids.

In preferred embodiment the strain is *Rhodococcus opacus*, most preferably *Rhodococcus opacus* PD630 carrying genes encoding cellobiase activity and cellobiose sugar transporters.

In this connection "lipid-containing cell mass" stands for a cell mass with a lipid content of at least 10%, preferably at least 15%, preferably at least 20% (w/w), more preferably at least 30%, most preferably at least 50% or more of dry matter of the microorganism.

Preferably oleaginous bacterial cell accumulates at least 15%, more preferably at least 20%, even more preferably at least 30%, at least 40%, at least 50% and most preferably at least 60% (w/w) of their biomass as lipid After cultivation the bacterial cells containing lipids may be separated from the spent culture medium by any known methods, such as using a filtration or decanting techniques. Alternatively, centrifugation with industrial scale commercial centrifuges of large volume capacity may be used to separate the desired products.

In various embodiments of the invention, oil, or precursors for oil, may be recovered from cell biomass or spent culture medium using any method known in the art. In various embodiments of the invention, microorganism cells may be disrupted to facilitate the separation of oil and other components. Any method known for cell disruption may be used, such as extrusion, ultra sonication, osmotic shock, mechanical shear force, cold press, thermal shock, enzyme-catalysed or self-directed autolysis. Also extraction with organic solvents can be used.

The oil extracted residual cell mass can be used for energy production, e.g. combusted or treated with anaerobic digestion process, or utilized as animal feed. Oil-extracted residual cell mass, or fraction thereof, can also be recycled back to the bioprocesses to be used as a source of carbon and/or nutrients.

"Residual cell mass" stands for a solid, semi-solid or flowing material fraction, which contains microorganisms treated for the recovery of intracellular lipids The method can be applied to any lignocellulosic materials including woody plants or non-woody, herbaceous plants or other materials containing cellulose. Materials can be agricultural residues (such as straw, e.g. wheat straw, rice straw, chaff, hulls, corn stover, corn cobs, sugarcane bagasse, tops and leaves); dedicated energy crops (such as switchgrass, *Miscanthus, Arundo donax*, reed canary grass, willow, water hyacinth), wood materials or residues (including forestry, sawmill, and pulp and/or paper mill residues or fractions), moss or peat, microorganisms or municipal paper or cardboard waste. Also low lignin materials, materials such as macroalgae or microalgae biomass can be used. In addition, the materials can be also cellulose fractions from industrial practises.

"Biofuel" refers to solid, liquid or gaseous fuel mainly derived from biomass or biowaste and is different from fossil fuels, which are derived from the organic remains of prehistoric plants and animals.

According to EU directive 2003/30/EU "biodiesel" refers to a methyl-ester produced from vegetable oil or animal oil, of diesel quality to be used as biofuel. More broadly, biodiesel refers to long-chain alkyl esters, such as methyl, ethyl or propyl-esters, from vegetable oil or animal oil of diesel quality. Biodiesel can also be produced from microorganism lipids, whereby microorganism lipid can originate from a bacterium, a fungus (a yeast or a mold), an algae or another microorganism.

"Renewable diesel" refers to a fuel which is produced by a hydrogen treatment of lipids of an animal, vegetable or microorganism origin, or their mixtures, whereby microorganism lipid can originate from a bacterium, a fungus (a yeast or a mold), an algae or another microorganism. Renewable diesel can be produced also from waxes derived from biomass by gasification and Fischer-Tropsch synthesis. Optionally, in addition to hydrogen treatment, isomerization or other processing steps can be performed. Renewable diesel process can also be used to produce jet fuel and/or gasoline. The production of renewable diesel has been described in patent publications EP 1396531, EP 1398364, EP 1741767 and EP 1741768.

Biodiesel or renewable diesel may be blended with fossil fuels. Suitable additives, such as preservatives and antioxidants may be added to the fuel product.

"Lubricant" refers to a substance, such as grease, lipid or oil, that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demulsifiers, antifoaming agents, cosolvents, and lubricity additives (see for example U.S. Pat. No. 7,691,792). Base oil for lubricant can originate from mineral oil, vegetable oil, animal oil or from a bacterium, fungi (a yeast or a mold), an algae or another microorganism. Base oil can also originate from waxes derived from biomass by gasification and Fischer-Tropsch synthesis. Viscosity index is used to characterise base oil. Typically high viscosity index is preferred.

The lipids produced according with the method described in this invention can be used as feedstock for the production of biodiesel, renewable diesel, jet fuel or gasoline. Biodiesel consists of fatty acid methyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogen deoxygenation, hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications.

Lipids produced with the method can be used as base oils for lubricants (lubrication oils) or as a starting material for production of base oils for lubricants.

The invention is illustrated by the following non-limiting examples. It should be understood that the embodiments given in the description above and the examples are for illustrative purposes only, and that various changes and modifications are possible within the scope of the invention.

EXAMPLES

The experimental part demonstrates introducing endo- and exocellulases to *R. opacus* and degradation cellulosic substrates to dimeric cellobiose as Examples 1 to 6, introducing cellobiase and cellobiase transporters to *R. opacus* and fat/oil production using cellobiose as a carbon source as Examples 7 to 13, construction of oleaginous strain capable of utilizing cellulosic substrate as Example 14 and complete cellulose degradation as Example 15.

Sequence numbers referring to sequences used in this study are listed in Table 1.

TABLE 1

Figure 16:
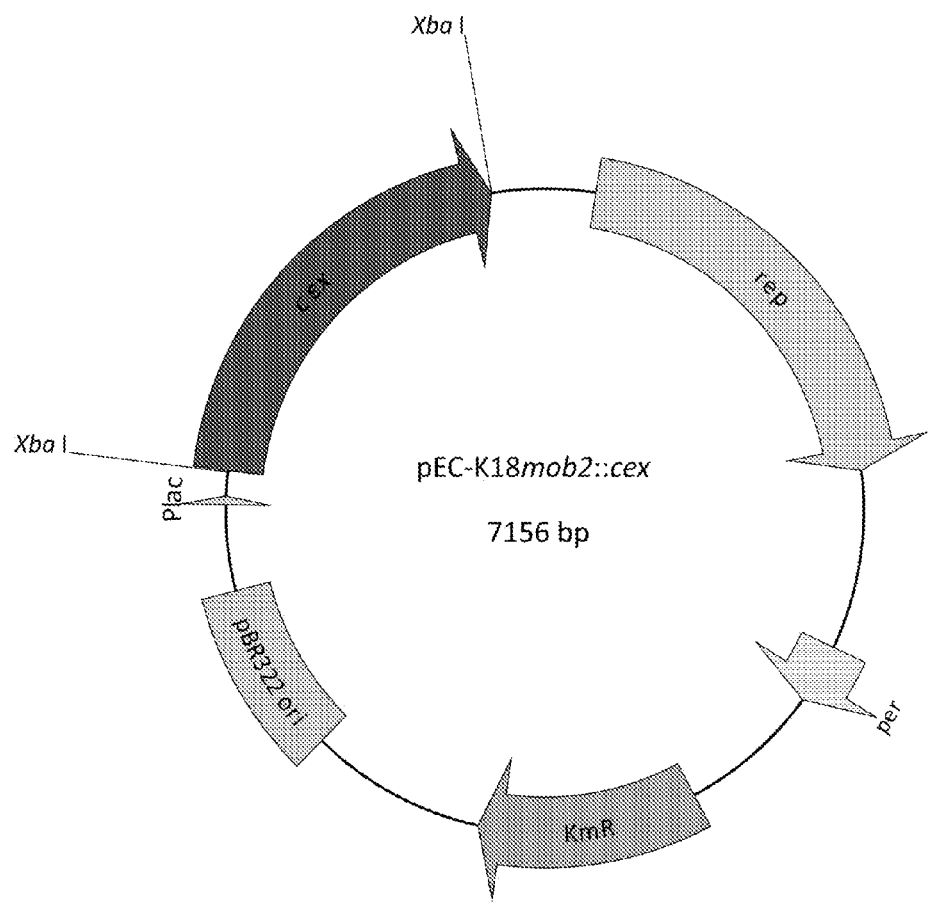
FIG. 16. Physical maps of the constructed plasmid pEC-K18mob2::cex

| Gene/protein | SEQ ID NO: | Comment |
|---|---|---|
| CenA | 1 | CenA Acc. No. P07984.1 |
| cenA | 2 | cenA Acc. No. M15823.1 |
| CenB | 3 | CenB Acc. No. YP_004451558.1 |
| cenB | 4 | cenB Acc. No. M64644.1 |
| CenC | 5 | CenC Acc. No. YP_004453058.1 |
| cenC | 6 | cenC Acc. No. X57858.1 |
| CbhA | 7 | CbhA Acc. No. YP_004453442.1 |
| cbhA | 8 | cbhA Acc. No. L25809.1 |
| Cex | 9 | Cex Acc. No. P07986.1 |
| cex | 10 | cex Acc. No. M15824.1 |
| Cel6A | 11 | Cel6A Acc. No. YP_289135.1 |
| cel6A | 12 | cel6A Acc. No. M73321.1 |
| BglA | 13 | BglA Acc. No. YP_288996 |
| bglA | 14 | bglA Acc. No. AF086819.2 |
| BglB | 15 | BglB Acc. No. YP_288997 |
| bglB | 16 | bglB Acc. No. AF086819.2 |
| BglC | 17 | BglC Acc. No. YP_288998 |
| bglC | 18 | bglC Acc. No. AF086819.2 |
| bglABC | 19 | see: FIG. 16 and Example 7 |
| FcenA | 20 | primer |
| RcenA | 21 | primer |
| FcenB | 22 | primer |
| RcenB | 23 | primer |
| FcenC | 24 | primer |

TABLE 1-continued

| Gene/protein | SEQ ID NO: | Comment |
|---|---|---|
| RcenC | 25 | primer |
| Fcex | 26 | primer |
| Rcex | 27 | primer |
| FcbhA | 28 | primer |
| RcbhA | 29 | primer |
| Fcel6A | 30 | primer |
| Rcel6A | 31 | primer |
| FbglABC | 32 | primer |
| RbglABC | 33 | primer |
| FcenA-SP | 34 | primer |
| FbglRER | 35 | primer |
| RbglRER | 36 | primer |
| FbglVH2 | 37 | primer |
| RbglVH2 | 38 | primer |
| Fbglx | 39 | primer |
| Rbglx | 40 | primer |
| FbglABC2 | 41 | primer |
| RbglABC2 | 42 | primer |
| FcenA2 | 43 | primer |
| RcenA2 | 44 | primer |

Example 1. Establishing Cellulose Degradation in *R. opacus* PD630

For heterologous expression in *R. opacus* PD630, 6 cellulases from two different cellulolytic Gram positive bacteria, *Cellulomonas fimi* ATCC484 (CenA, CenB, CenC, Cex and CbhA) and *Thermobifida fusca* DSM43792 (Cel6A), were chosen, due to their high activity toward cellulose, a suitable signal peptide which should allow secretion of these cellulases by *R. opacus* PD630 and the high G+C content of the respective genes, which should match the *R. opacus* PD630 codon usage.

All the genes were ligated either to the vector pEC-K18mob2 under the control of the lac-promoter or the vector pJAM2 under the control of the acetamidase-promoter and transferred to *E. coli* Mach1-T1 for qualitative activity assays. It was shown earlier that heterologous expression of cellulases from Gram positive bacteria in *E. coli* led to the accumulation of these enzymes in the cytoplasm and periplasm and that the increased level of expression resulted in the non-specific leakage of the premature but active enzyme into the medium (Guo Z. et al., 1988).

TABLE 2

Bacterial strains, plasmids and oligonucleotides used in this study

| Strain, plasmid or primer | Relevant characteristics | Source or reference |
|---|---|---|
| Strains | | |
| *E. coli* XL10 Gold | endA1 glnV44 recA1 thi-1 gyrA96 relA1 lac Hte Δ(mcrA)183 Δ(mcrCB-hsdSMR-mrr)173 tet$^R$ F'[proAB lacI$^q$ZΔM15 Tn10(Tet$^R$ Amy Cm$^R$)] | Stratagene |
| *E. coli* Mach1-T1 | F$^-$ φ80(lacZ)ΔM15 ΔlacX74 hsdR(r$_K$-, m$_K$+) ΔrecA1398 endA1 tonA | Invitrogen |
| *R. opacus* PD630 | TAG producing strain | (Alvarez et al., 1996) |
| *C. fimi* ATCC484 | Cellobiose utilization | (Stackebrandt E, 1979) |
| *T. fusca* DSM43792 | Cellobiose utilization | (McCarthy, 1984) |
| Plasmids | | |
| pEC-K18mob2 | | (Tauch et al., 2002) |

TABLE 2-continued

Bacterial strains, plasmids and oligonucleotides used in this study

Figure 11:
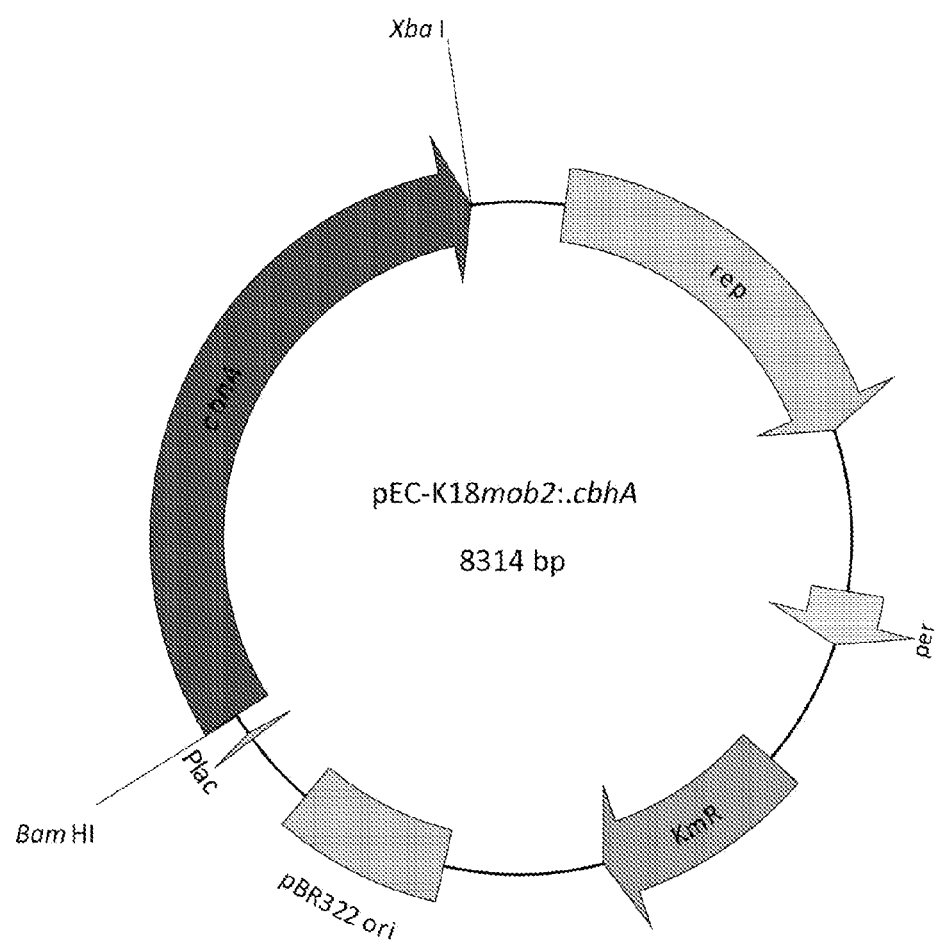
FIG. 11. Physical maps of the constructed plasmid pEC-K18mob2:.cbhA
Figure 12:
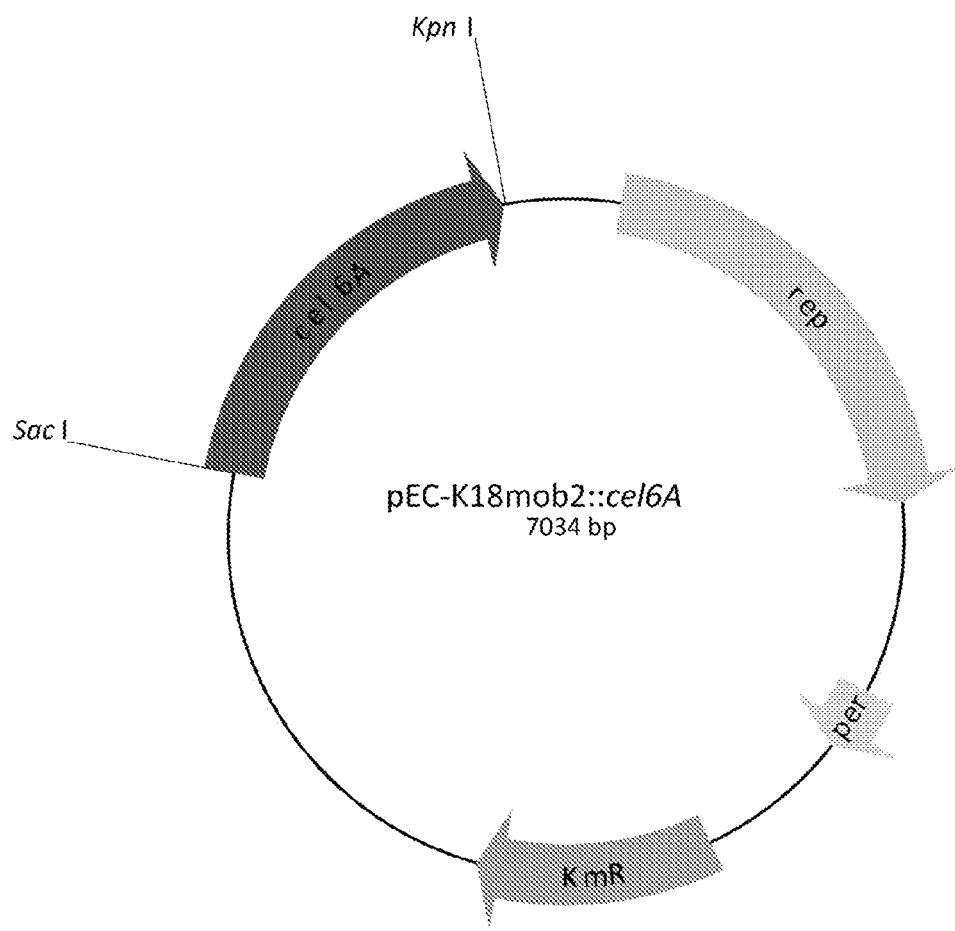
Figure 13:
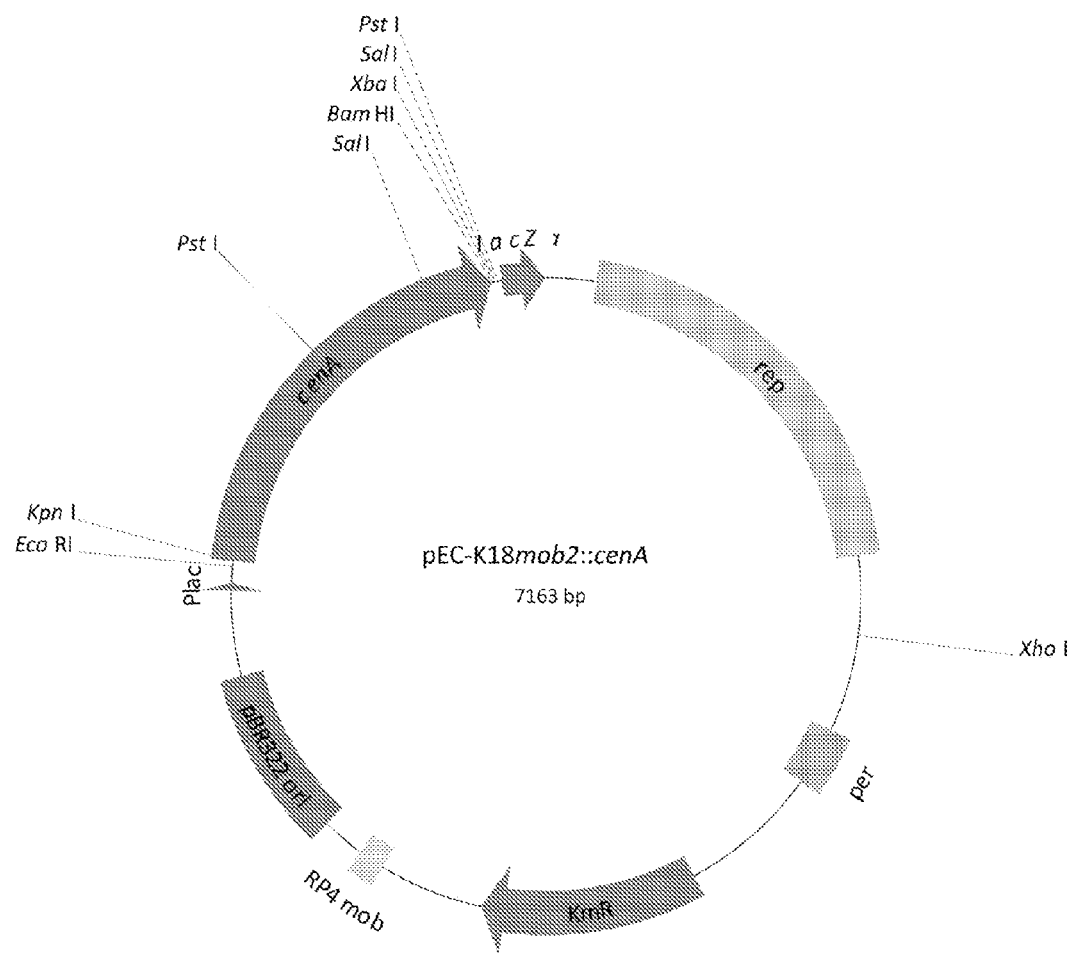
FIG. 13. Physical maps of the constructed plasmid pEC-K18mob2::cenA
Figure 14:
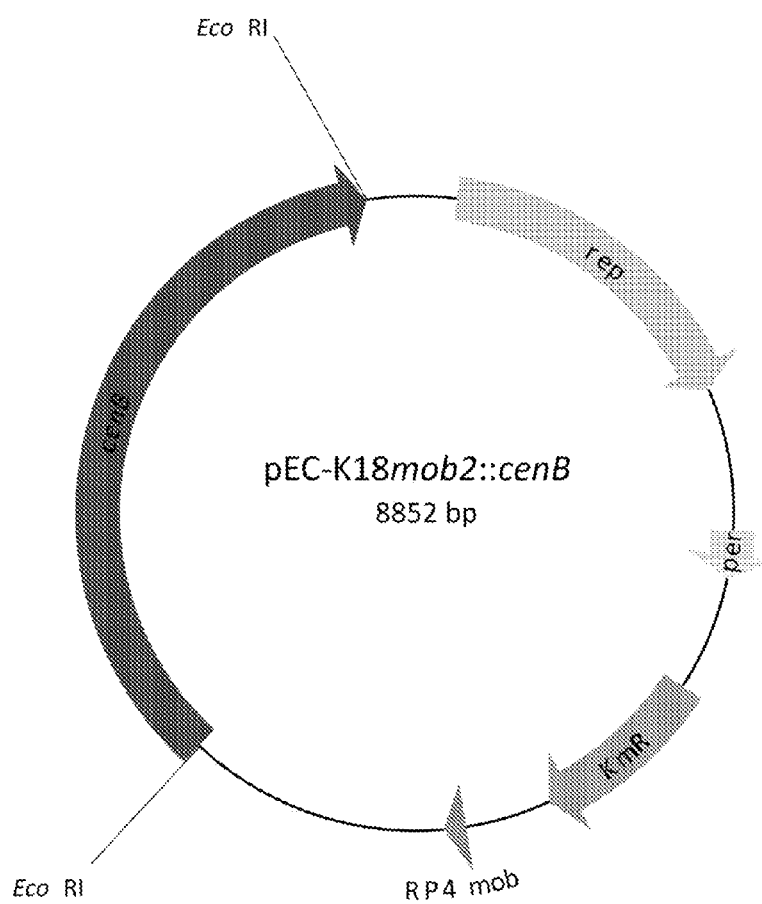
FIG. 14. Physical maps of the constructed plasmid pEC-K18mob2::cenB
Figure 15:
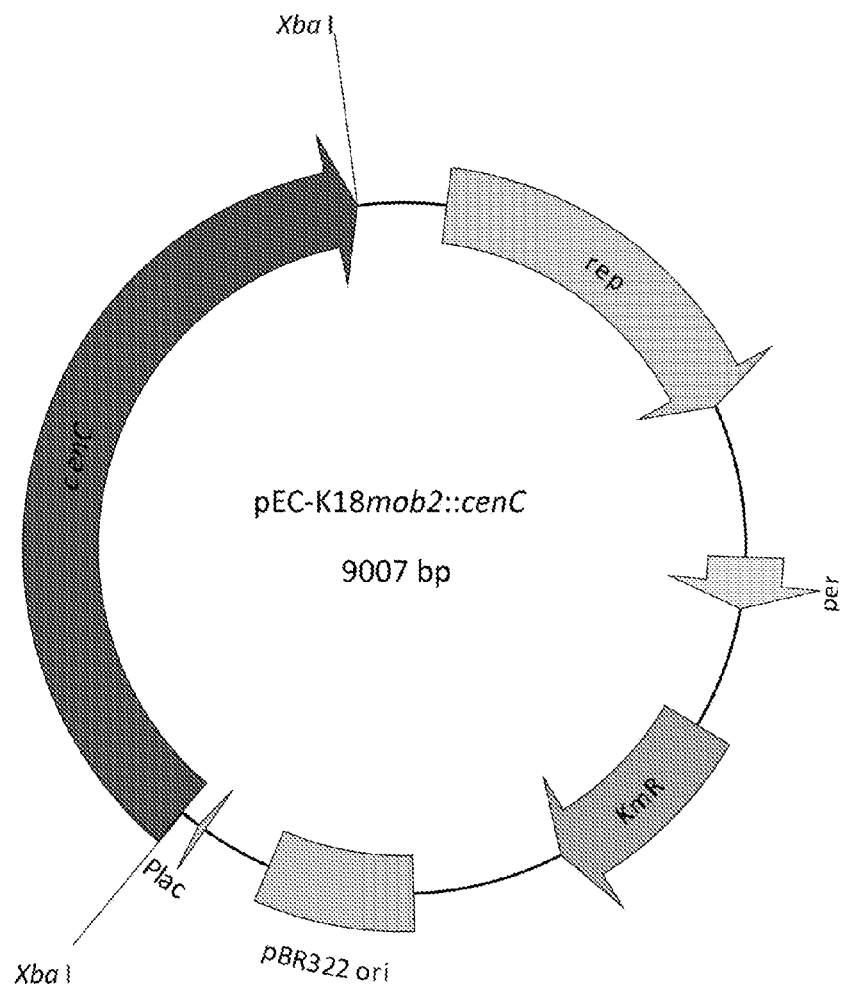
FIG. 15. Physical maps of the constructed plasmid pEC-K18mob2::cenC

| Strain, plasmid or primer | Relevant characteristics | Source or reference |
|---|---|---|
| pJAM2 | | (Triccas et al., 1998) |
| pEC-K18mob2::cenA | cenA as EcoRI/BamHI fragment | this study; FIG. 13 |
| pEC-K18mob2::cenB | cenB as EcoRI fragment | this study; FIG. 14 |
| pEC-K18mob2::cenC | cenC as XbaI fragment | this study; FIG. 15 |
| pEC-K18mob2::cex | cex as EcoRI fragment | this study; FIG. 16 |
| pEC-K18mob2::cbhA | cbhA as BamHI/XbaI fragment | this study; FIG. 11 |
| pEC-K18mob2::cel6A | cel6A as SacI/KpnI fragment | this study; FIG. 12 |
| pEC-K18mob2::cenA-SP | cenA-SP as EcoRI/BamHI fragment | this study |
| pEC-K18mob2::cenBA | cenBA as EcoRI/BamHI fragments | this study |
| pJAM2::cenC::cex::cbhA | cenC, cex and cbhA as XbaI/ClaI fragments | this study |
| Oligonucleotides | | |
| FcenA | GGGAGCTCCTTGATGTCCACCCGCAGAACC | |
| RcenA | TCACCACCTGGCGTTGCGCGCC | |
| FcenB | AAAGAATTCGGAAGAGGACCCCATGCTCCGCC | |
| RcenB | AAAGAATTCTCAGCCGCAGACCTCACCGTTCACG | |
| FcenC | AAATCTAGAAGGGGAGACAGAGTGGTTTCTCGCAGGTCATC | |
| RcenC | AAATCTAGATCAGCTGCGCGGACGCTGCACGGCGAGCTC | |
| Fcex | AAAGAATTCAAGGAGGAGATCAAATGCCTAGGACCACGCCCGC | |
| Rcex | ATATGAATTCTCAGCCGACCGTGCAGGGCG | |
| FcbhA | AAAGGATCCGGAGGACCACGTGTCCACACTCGGC | |
| RcbhA | AAATCTAGATCAGCCGAGCGTGCAGGC | |
| Fcel6A | AAAGAGCTCGGAAGAGGACCCCATGTCCCCCAGACCTCTTCGC | |
| Rcel6A | AAAGGTACCTCAGCTGGCGGCGCAGGTAAG | |
| FcenA-SP | AAAGAATTCGGGAGCTCCTTGATGGCTCCCGGCTGCCGCGTCGACTAC | |

Isolation, Analysis and Modification of DNA:

Plasmid DNA was prepared from crude lysates by the alkaline extraction method (Birnboim & Doly, 1979). Total DNA of *C. fimi* ATCC484, and *T. fusca* DSM43792 was prepared using the Qiagen DNeasy Blood & Tissue Kit (Qiagen, Hilden, Germany) according to the manufacturer's protocol. Restriction endonucleases (Fermentas, St. Leon Rot, Germany) were applied under conditions recommended by the manufacturer. All other genetic procedures and manipulations were conducted as described by (Sambrook et al., 1989).

Constructions of Plasmids and Transfer to *E. coli*:

The coding regions of cenA, cenB, cenC, cex and cbhA from *C. fimi* ATCC484 and cel6A from *T. fusca* DSM43792 were amplified by PCR using oligonucleotides FcenA and RcenA for cenA, FcenB and RcenB for cenB, FcenC and RcenC for cenC, Fcex and Rcex for cex, FcbhA and RcbhA for cbhA and Fcel6A and Rcel6A for cel6A, and FcenA-SP and RcenA for cenA-SP, respectively (Table 1). For PCR, Herculase II DNA Polymerase (Agilent, Santa Clara, USA) was used according to the manufacturer's instructions. PCR products were extracted from gel after separation using the PeqGOLD gel extraction kit (Peqlab, Erlangen, Germany). All plasmids were transferred to *E. coli* strains XL10 Gold and Mach1-T1 by transformation (Hanahan, 1983).

Transfer into *R. opacus*:

For expression experiments in *R. opacus*, the *E. coli*/ *Corynebacterium glutamicum* shuttle vector pEC-K18mob2 (Tauch et al., 2002) and *E. coli*/*Mycobacterium smegmatis* shuttle vector pJAM2 (Triccas, Parish, Britton, & Gicquel, 1998) were used for cloning of cenA, cenB, cenC, cex, cbhA, cel6A and cenA-SP which conferred kanamycin (50-75 µg/ml) resistance for selection to *E. coli* and *R. opacus* strain PD630, using the respective restriction enzymes (Table 2).

Figure 9:
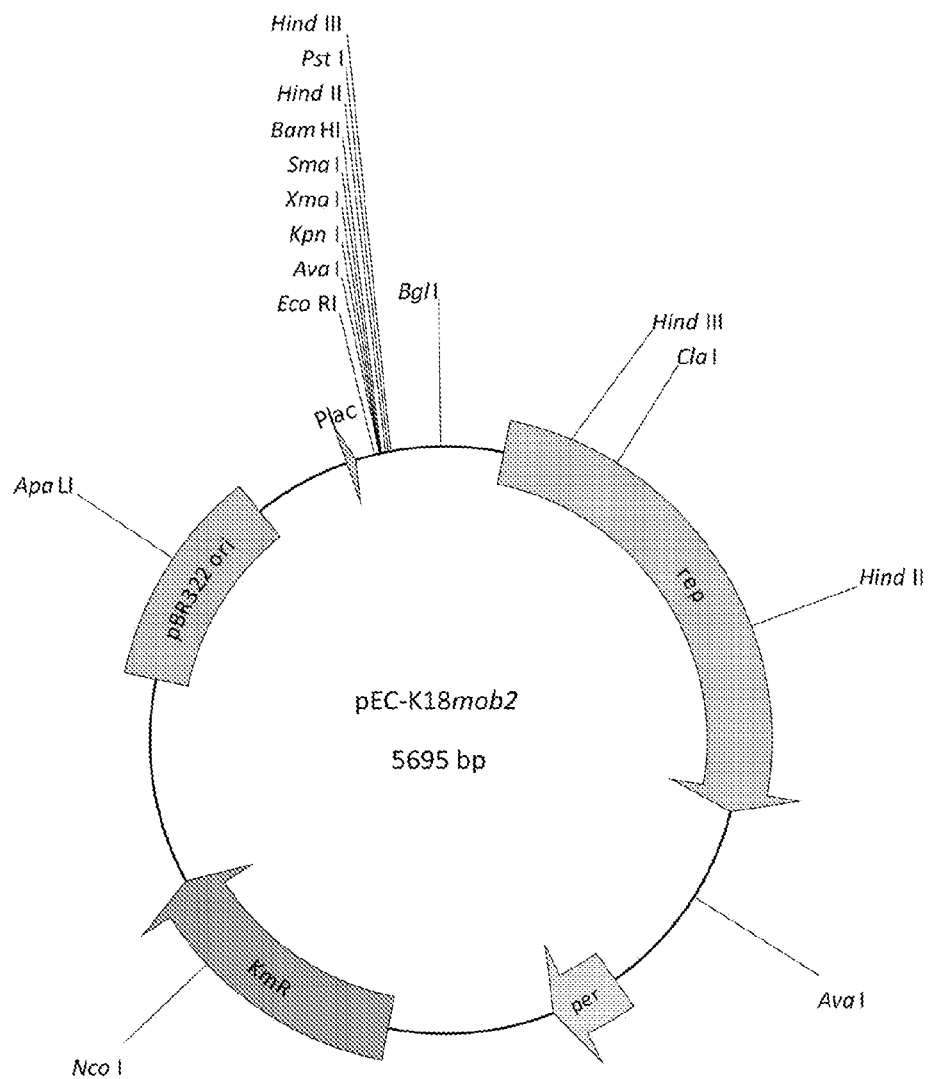
FIG. 9. Physical maps of the plasmid pEC-K18mob2.

Plasmids pEC-K18mob2 (FIG. 9), pEC-K18mob2::cenA (FIG. 13), pEC-K18mob2::cenB (FIG. 14), pEC-K18mob2::cenC (FIG. 15), pEC-K18mob2::cbhA (FIG. 11), pEC-K18mob2::cex (FIG. 16), pEC-K18mob2::cel6A, pEC-K18mob2::cenA-SP pJAM2 and pJAM2::cenC::cex::cbhA (Table 2) were transferred by electroporation applying the previously described protocol (Kalscheuer, Arenskotter, & Steinbuchel, 1999).

Example 2. Secretion Analysis of Cellulases

In order to proof if the cellulases are translocated through the membrane or if the cellulase activity in the medium is the result of cell death and subsequent leakage of the enzyme by cell lysis, the signal peptide as predicted by SignalP (Petersen, Brunak, von Heijne, & Nielsen, 2011) and previous determinations (Wong et al., 1986) was omitted from cenA by PCR and the product was ligated to vector pEC-K18mob2, yielding plasmid pEC-K18mob2::cenA-SP. The plasmid was transferred to *E. coli* Mach1-T1 and *R. opacus* PD630 and the cellulase-activity was determined. Neither colonies of recombinant *E. coli* nor *R. opacus* PD630 exhibited clear zone formation on MSM plates containing 1% (wt/vol) CMC after 2 days of incubation in contrast to the control strains harboring pEC-K18mob2::cenA (FIG. 13).

To check whether the modified CenA is active or not, the soluble cell and membrane fraction of disrupted *R. opacus* PD630 pEC-K18mob2::cenA-SP cells was screened for activity.

Preparation of Soluble Cell and Membrane Fractions of *R. opacus* PD630:

A 50 mL culture of *R. opacus* PD630 was incubated for 24 h at 30° C. Cells were harvested by centrifugation (4000×g) for 15 min, washed twice with sterile saline (0.8% (wt/vol) NaCl) and suspended in 5 mL of 50 mM sodium phosphate buffer (pH 7.4). Cells were lysed by tenfold passage through a precooled French Pressure Cell at 1.000 MPa. The obtained lysates were centrifuged as before in order to remove residual cells and the soluble and membrane fraction were prepared by 1 h centrifugation of the supernatant at 100,000×g and 4° C.

It could be found that cellulase activity was only present in the soluble cell fraction, thus indicating that the truncated enzyme was no longer secreted through the cell membrane and that vice versa the native enzyme is translocated and not leaked. Thus, it was proven that cellulases are translocated through the membrane.

Example 3. Qualitative Cellulase Activity Assay

Qualitative analysis of cellulase activity was done as described by (Beguin, 1983). In brief, recombinant strains of *R. opacus* PD630 harboring cellulases were incubated on MSM plates containing 0.5% (wt/vol) carboxymethyl cellulose (CMC) at 30° C. for 2 days. Directly thereafter the plates were stained with a 0.1% (wt/vol) Congo red solution for 5 minutes. Destaining was done with a 1 M NaCl solution until clear zones were visible.

Figure 1:
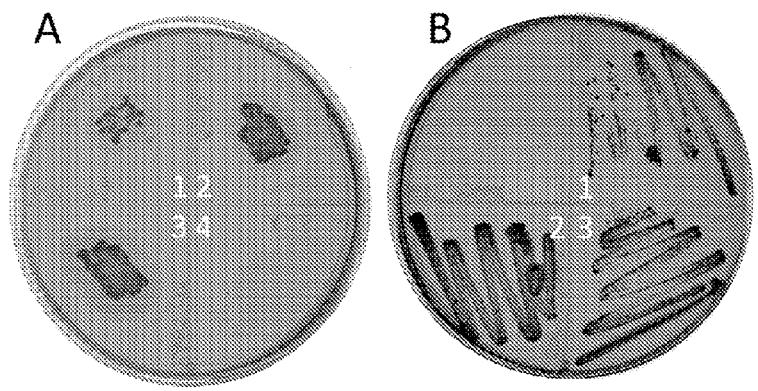
FIG. 1. Qualitative cellulase enzyme assay. Recombinant strains of *E. coli* Mach1-T1 and *R. opacus* PD630 were transferred onto MSM plates with 0.5% (wt/vol) carboxymethyl cellulose and 0.1% (wt/vol) glucose as carbon source. After 2 days, plates were stained with 0.1% (wt/vol) congo red and destained with 1 M NaCl. A: 1, *E. coli* Mach1-T1 pEC-K18mob2::cenB; 2, *R. opacus* pEC-K18mob2::cenA; 3, *R. opacus* pJAM2::cenC::cex::cbhA; 4, *E. coli* Mach1-T1 pEC-K18mob2::cenA. B: 1, *R. opacus* pEC-K18mob2; 2, *R. opacus* pJAM2::cenC::cex::cbhA; 3, *R. opacus* pEC-K18mob2::cenA.

All tested cellulases exhibited activity, visible by clear zone formation on MSM plates containing 0.5% (wt/vol) carboxymethyl cellulose (CMC) after staining with Congo red, and the corresponding plasmids were subsequently transferred to *R. opacus* PD630. Interestingly, no transformants could be obtained neither for plasmid pEC-K18mob2::cenB nor the double construct pEC-K18mob2:: cenBA. In contrast to the tested recombinant *E. coli* strains, all plasmids with the exception of plasmid pEC-K18mob2:: cbhA (FIG. 11) and pEC-K18mob2::cex (FIG. 12), conferred the ability to degrade cellulose to *R. opacus* PD630, whereas cellulase activity was absent in the vector control strains (FIG. 1). However it was noted that no clear zone formation could be observed after staining of MSM plates with 0.1% (wt/vol) MCC-overlay instead of CMC.

Example 4. Quantitative Determination of Enzyme Activities

Cells of *R. opacus* PD630 were cultivated at 30° C. in mineral salts medium (MSM) as described by (Schlegel, H. G., Kaltwasser, H., and G. Gottschalk, 1961). Carbon sources were added to liquid MSM as indicated in the text. Liquid cultures in Erlenmeyer flasks were incubated on a horizontal rotary shaker at an agitation of 110 rpm. Solid media for qualitative cellulase assay were prepared by addition of 1.5% (wt/vol) agar/agar.

Cells of *Escherichia coli* were cultivated at 37° C. in Lysogeny Broth (LB, (Bertani, 2004)). Cells of *Thermobifida fusca* DSM43792 were grown in Czapek peptone medium at 42° C. (Waksman, 1961) and cells of *Cellulomonas fimi* ATCC484 were grown in Standard I medium at 30° C. (Carl Roth, Karlsruhe, Germany). Antibiotics were applied according to (Sambrook, Fritsch, & Manitas, 1989) and as indicated in the text.

Figure 3:
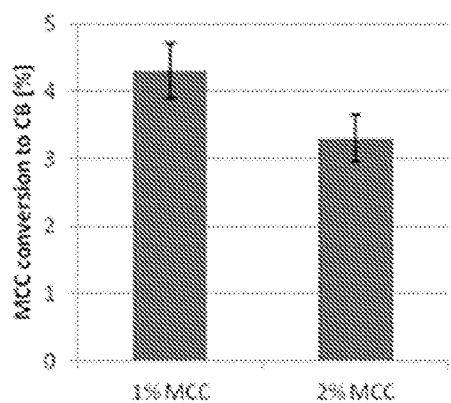
FIG. 3. Quantitative cellulase enzyme assay. Recombinant strains of *R. opacus* PD630 were alone or in combination cultivated in liquid MSM with 1% (wt/vol) microcrystalline cellulose and 1% (wt/vol) glucose if not indicated otherwise, and cellobiose contents were determined at the indicated time points. Error bars indicate standard deviations of triplicate measurements.
Figure 4:
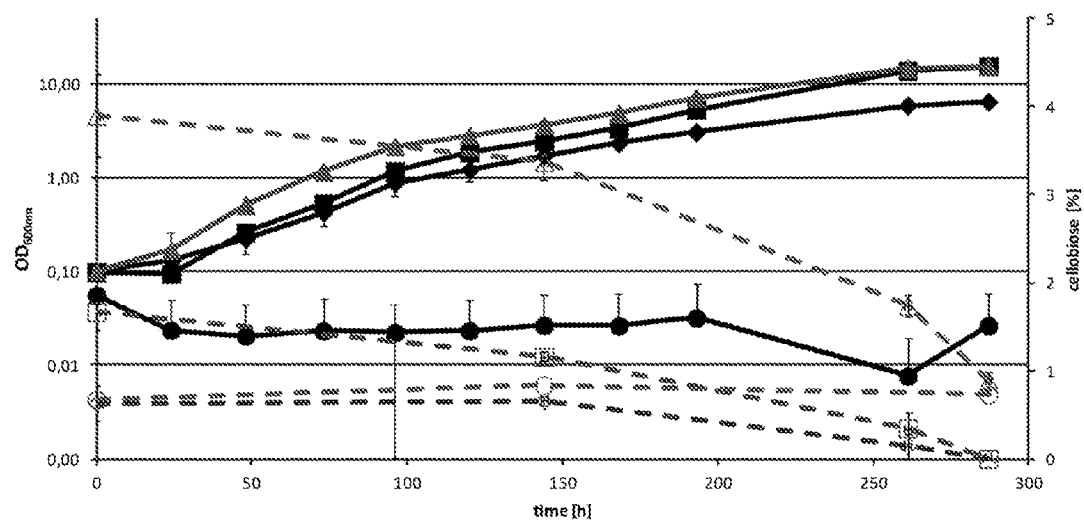
FIG. 4. Growth of recombinant *R. opacus* PD630 pEC-K18mob2::bglABC and cellobiose concentration of the medium. Cells were cultivated in liquid MSM containing 1%, 2% and 4% (wt/vol) cellobiose as sole carbon source. ♦ 1% (wt/vol) cellobiose, ■ 2% (wt/vol) cellobiose, ▲ 4% (wt/vol) cellobiose, ● control strain *R. opacus* PD630 pEC-K18mob2 with 1% (wt/vol) cellobiose. △ cellobiose concentration [%] 4% (wt/vol) culture, △ 2% (wt/vol) culture, ◇ 1% (wt/vol) culture, ○ control culture 1% (wt/vol).

To quantify cellulase activities in the culture medium of recombinant strains, cells were cultured in liquid MSM with microcrystalline cellulose (MCC) as substrate. Culture media were centrifuged at 14.000×g to remove cells. Supernatants were filtered using Spartan 0.2 µm filters (Whatman, Dassel, Germany) and applied on an Eurokat Pb column (30GX350EKN, Knauer, Berlin, Germany) using water/ acetonitrile 95:5 as eluent at 75° C. and a flow rate of 0.5 mL×min$^{-1}$. The HPLC systems used comprises a Kontron system 522 pump and HPLC 560 autosampler (Kontron, München, Germany) and a Sedex 80 LT-ELS detector (Sedere, Alfortville, France). The concentrations of the main cellulase product cellobiose were determined by HPLC after 16, 25, 38 and 45 days of incubation (FIG. 3).

Consistent with the previous experiments with CMC as substrate, all tested cellulases exhibited activity toward MCC in liquid culture, and no activity was found in the vector control strains. In comparison to each other, *R. opacus* PD 630 recombinant strains expressing cenA exhibited the highest MCC conversion rates, reaching 2.16%±0.07% (wt/vol) of converted MCC after 35 days; whereas strains expressing cel6A reached 2.06%±0.02% (wt/vol). It was assumed that different amounts of the carbon source glucose added to the cultures should have an effect on the MCC conversion rate due to the lower cell densities and thus lower amounts of cellulase. To verify this assumption, recombinant *R. opacus* PD 630 cells expressing cenA were cultivated with 0.5% (wt/vol) and 0.1% (wt/vol) glucose as carbon source. The MCC conversion rates of these cultures reached 1.78%±0.02% (wt/vol) and 1.31%±0.04% (wt/vol) respectively, indicating a non-proportional dependency of carbon source and cellobiose product formation. However, the addition of 0.2% (wt/vol) yeast extract was shown to increase cellobiose formation (2.6%±0.05% (wt/vol). Cellulases, especially exo- and endocellulases, act in concert to degrade cellulose (Lynd et al., 2005; Mosier et al., 1999). To find suitable enzyme combinations, different co-cultivations of recombinant *R. opacus* PD630 expressing different cellulase genes were done. As expected, cultures with combinations of exo- and endocellulases exhibited conversion rates superior to single or double-endocellulase cultures. Highest cellobiose contents could be measured when all available cellulases were used (3.73%±0.03% (wt/vol), followed by pEC-K18mob2::cenA/pJAM2::cenC::cex::cbhA and pEC-K18mob2::cel6A/pJAM2::cenC::cex::cbhA cultures (3.64%±0.05% (wt/vol) and 3.16%±0.05% (wt/vol), respectively). The double culture pEC-K18mob2::cenA/cel6A exhibited only 2.14%±0.02% (wt/vol), thus lower than CenA alone.

Example 5. Optimization of Conversion Rates

Figure 2:
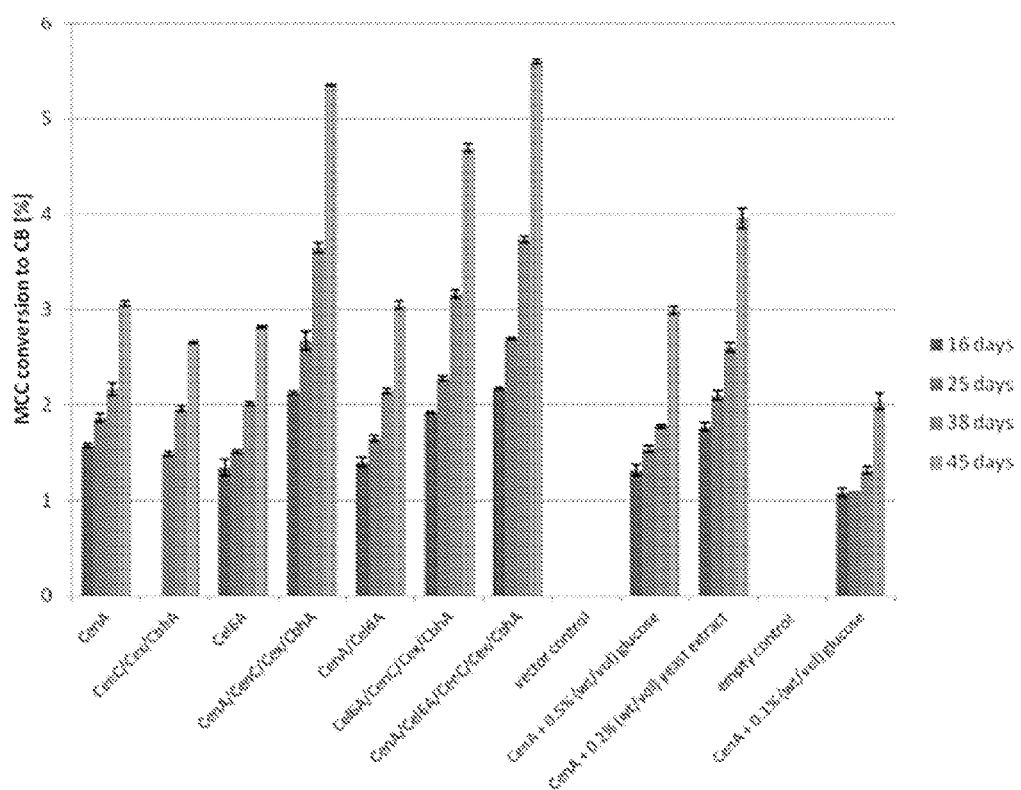
FIG. 2. Quantitative cellulase enzyme assay. Strains of *R. opacus* PD630 pEC-K18mob2::cenA/cenC/cel6A/pJAM2::cenC::cex::cbhA were cultivated in liquid MSM with 1% (dark grey) or 2% (wt/vol) microcrystalline cellulose and 1% (wt/vol) glucose (light grey), and cellobiose contents were determined after 25 days. Error bars indicate standard deviations of triplicate measurements.

Because the achieved conversion rates in the first experiments were comparably low, further studies aimed on a preliminary optimization. The pH of the culture medium was lowered from originally pH 6.9 to 6.5 and 6, and for additional cultures the amount of substrate was augmented to 2% (wt/vol) MCC. All cultures were co-inoculated with recombinant cells of *R. opacus* PD630 expressing genes for cellulases (pEC-K18mob2::cenA/cenC/cel6A/pJAM2::cenC::cex::cbhA) and contents of cellobiose were determined after 25 days of incubation (FIG. 2). It turned out that lowered pH values of the culture medium had a strongly inhibitory effect on the growth of *R. opacus* PD630 and thus only minor amounts of cellobiose could be detected (data not shown). However, it could be observed that compared to previous cultivations the additional expression of cenC by the high copy vector pEC-K18mob2 increased the MCC conversion rate by 60% (2.7±0.01% (wt/vol) to 4.3±0.08% (wt/vol), respectively). In the 2% (wt/vol) MCC culture, total cellobiose concentration was highest, however the conversion rate reached 3.3%±0.16% (wt/vol).

Example 6. Degradation of Cellulosic Materials

Besides artificial cellulose substrates, the capability of recombinant *R. opacus* PD630 to degrade natural cellulose containing materials is of special interest. In total 5 different unprocessed materials, softwood sawdust, shredded copy paper, wheat straw, cotton and sanitary paper were tested as possible substrates. 1% (wt/vol) of the corresponding material served as substrate, whereas 1% (wt/vol) glucose was used as carbon source. Cellulase activity could be observed for all tested substrates except for sawdust (Table 3). In general, cellulase activity augmented with an increase in the substrates surface, e.g. sanitary paper which became rapidly suspended versus the more rigid copy paper, and decreased with lignin content, e.g. wheat straw and softwood sawdust. Where tested, the use of different cellulases in concert again proofed superior to the use of the endocellulase CenA alone. These experiments clearly demonstrated that not only commercially available, purified cellulose derivates can be hydrolyzed by recombinant strains, but also real cellulosic raw materials including waste and residue materials can be hydrolyzed. Furthermore, total cellobiose yield for cultures with sanitary paper reached the highest level of all substrates tested in this study (7.2% (wt/vol)).

TABLE 3

Conversion rates of different cellulosic materials by recombinant cellulases. Co-cultivation: *R. opacus* PD630 pEC-K18mob2::cenAlcenClcel6A/pJAM2::cenC::cex::cbhA. CenA reference: *R. opacus* PD630 pEC-K18mob2::cenA.

| Substrate | co-cultivation | CenA reference |
| --- | --- | --- |
| copy paper | 3.31% ± 0.18% | 1.8% |
| cotton | 5.33% ± 0.91% | 4.3% |
| sawdust | ND | 0% |
| sanitary paper | ND | 7.2% |
| wheat straw | ND | 1.3% |

ND, not determined.

Example 7. Utilization of Cellobiose

Search for Genes Encoding Enzymes Catabolizing Beta-Glucosidases and Cellobiose Sugar Transporters in *R. opacus* PD630:

Previous studies concluded that the cellobiose deficiency is due to a missing active glycoside hydrolase enzyme (Holder and others 2011). An in silico analysis employing the blastp algorithm, the pfam CD database and a protein database for *R. opacus* strain PD630 investigated the genome of *R. opacus* strain PD630 for genes coding for functional enzymes required for catabolism of cellobiose. One gene of 2439 bp, OPAG_01566 identified as glycosyl hydrolase, was found using beta-glucosidases as query. The predicted protein contains both N-terminal glycosyl hydrolase family 3 (pfam00933) and a disrupted C-terminal glycoside hydrolase family 3 (pfam01915) domain. No signal peptide is predicted by SignalP, suggesting a cytoplasmic located enzyme. Additionally, the search for ATP-sugar transport proteins only yielded multiple proteins identified as 2-aminoethylphosphonate ABC transporter with relatively low similarities to annotated cellobiose-ATP-transporters (data not shown).

Strategies to Establish Cellobiose Utilization in *R. opacus* PD630:

In order to establish cellobiose utilization, four different strategies were applied. The first one, employing two extracellular β-glucosidases from *R. erythropolis* and *G. polyisoprenivorans*, respectively, which both can use cellobiose as sole carbon and energy source, aimed at the extracellular cleavage of cellobiose and subsequent uptake of the generated glucose. The second and third attempts were to complement the lack of a suitable sugar transporter (Rer36840, ATP-dependent cellobiose uptake protein) or cytoplasmic β-glucosidase (Bglx, (Yang and others 1996)), respectively, and finally the fourth attempt to complement both (BglABC). The operon bglABC, first described and partially characterized by (Spiridonov and Wilson 2001) comprises two ABC sugar transport proteins (BglA, BglB) and a cytoplasmic β-glucosidase (BglC).

Isolation, Analysis and Modification of DNA:

Plasmid DNA was prepared from crude lysates by the alkaline extraction method (Birnboim and Doly 1979). Total DNA of R. erythropolis, G. polyisoprenivorans, T. fusca and of E. coli strain K-12 was prepared using the Qiagen DNeasy Blood & Tissue Kit (Qiagen, Hilden, Germany) according to the manufacturer's protocol. Restriction endo-

TABLE 4

Bacterial strains, plasmids and oligonucleotides used in this study

Figure 10:
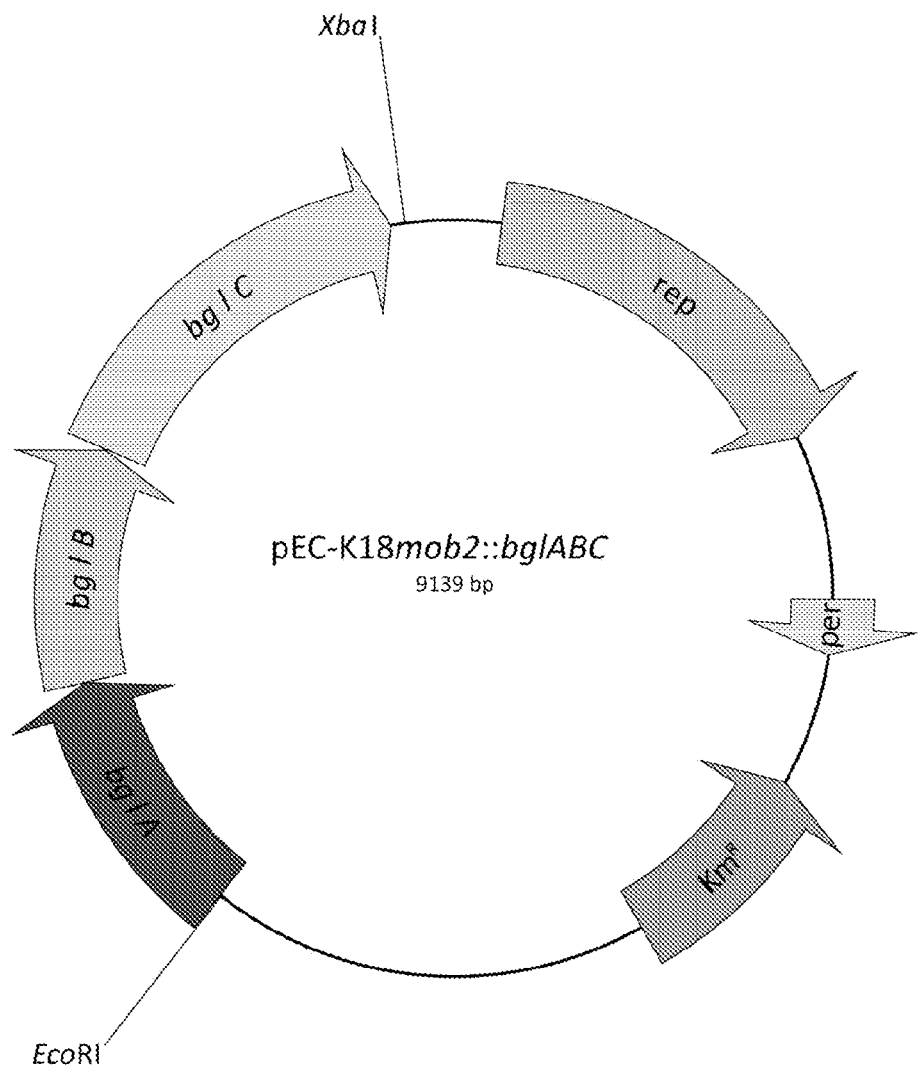
FIG. 10. Physical map of the constructed plasmid pEC-K18mob2::bglABC. Relevant cleavage sites and structural genes are indicated (KmR, kanamycin resistance cassette, rep, origin of replication; bglABC operon encoding two sugar transporters (bglAB, ACCESSION No. YP_288996 and YP_288997; SEQ ID NOs: 13 to 16) and a beta-glucosidase (bglC, ACCESSION No. YP_288998, SEQ ID NOs: 17 and 18) from *T. fusca*.

| Strain, plasmid or primer | Relevant characteristics | Source or reference |
|---|---|---|
| Strains | | |
| E. coli XL10 Gold | endA1 glnV44 recA1 thi-1 gyrA96 relA1 lac Hte Δ(mcrA)183 Δ(mcrCB-hsdSMR-mrr)173 tet$^R$ F'[proAB lacI$^q$ZΔM15 Tn10(Tet$^R$ Amy Cm$^R$)] | Stratagene |
| R. opacus PD630 | TAG producing strain | (Alvarez and others 1996) |
| R. erythropolis DSM43066 | Cellobiose utilization | (Goodfellow, Alderson, Lacey 1979) |
| T. fusca DSM43792 | Cellobiose utilization | (McCarthy 1984) |
| G. polyisoprenivorans VH2 | Cellobiose utilization | (Linos and others 1999) |
| Plasmids | | |
| pEC-K18mob2 | | (Tauch and others 2002) |
| pEC-K18mob2::bglRER | bglRER as BamHI/XbaI fragment | this study |
| pEC-K18mob2::bglVH2 | bglVH2 as XbaI fragment | this study |
| pEC-K18mob2::bglx | bglx as EcoRI/KpnI fragment | this study |
| pEC-K18mob2::bglABC | bglABC as EcoRI/XbaI fragment | this study; FIG. 10 |
| Oligonucleotides | | |
| FbglRER | AAAGGATCCGGGAGCTCCTTGA TGGCACTGACGTGCCTGCT | |
| RbglRER | AAATCTAGATCATCGAGTAGCC GTACAGCTGCG | |
| FbglVH2 | AAATCTAGAGGAAGAGGACCCC ATGAGCCGACCTCACCACC | |
| RbglVH2 | AAATCTAGACTAGAGCTGTGCC CGCGGCC | |
| Fbglx | AAAGAATTCGGGAGCTCCTTGA TGGATTTATTCGGCAACCATCC ATTAA | |
| Rbglx | AAGGTACCTTACAGCAACTCAA ACTCGCCTTTCTTAACG | |
| FbglABC | AAAGAATTCGGCCGTCCTCTCT TCCATCTGACATCTGACCTCTC | |
| RbglABC | AAATCTAGAGCCGCCGGGACG GCGAGATTTTGACCTATC | | nucleases (Fermentas, St. Leon Rot, Germany) were applied under conditions recommended by the manufacturer. All other genetic procedures and manipulations were conducted as described by (Sambrook, Fritsch, Manitas 1989).

Construction of Different pEC-K18mob2 Expression Vectors for *R. opacus* PD630:

The PCR products of the bglRER, bglVH2, rer36840 and bglABC, comprising suitable ribosome binding sites for *R. opacus* PD630 were cloned into the *E. coli/C. glutamicum* shuttle vector pEC-K18mob2 under the control of the lac-promoter, which should allow constitutive expression of the cloned genes in *R. opacus* PD630, yielding plasmids pEC-K18mob2::bglRER, pEC-K18mob2::bglVH2, pEC-K18mob2::rer36840 and pEC-K18mob2::bglABC (FIG. 10). Additionally, the bglx gene from *E. coli* was amplified by PCR removing the signal sequence for periplasmic location and subsequently ligated to pEC-K18mob2 (pEC-K18mob2::bglx).

Constructions of Plasmids and Transfer into *R. opacus*:

The coding regions of bglRER from *R. erythropolis*, bglVH2 from *G. polyisoprenivorans*, bglx from *E. coli* and bglABC from *T. fusca*, were amplified by PCR using oligonucleotides FbglRER and RbglRER for bglRER, FbglVH2 and RbglVH2 for bglVH2, Fbglx and Rbglx for bglx, Frer36840 and Rrer36840 for rer36840 and FbglABC and RbglABC for bglABC respectively (Table 4). For PCR, Herculase II DNA Polymerase (Agilent, Santa Clara, USA) was used according to the manufacturer's instructions. PCR products were extracted from gel after separation using the PeqGOLD gel extraction kit (Peqlab, Erlangen, Germany). For expression experiments in *R. opacus*, the vector pEC-K18mob2 (Tauch and others 2002) was used for cloning of bglrer, bglVH2, bglx, rer36840 and bglABC that conferred kanamycin (50 μg/ml) resistance for selection to *E. coli* and *R. opacus* strain PD630, using the respective restriction enzymes (Table 4). All plasmids were transferred to *E. coli* strain XL10 Gold by transformation (Hanahan 1983).

Transfer of Plasmids to *R. opacus* Strain PD630 and Establishment of Cellobiose Utilization:

All plasmids including empty pEC-K18mob2 as vector control were transferred to *R. opacus* PD630 by electroporation. Recombinant strains were cultivated both on solid and in liquid MSM with 1% (w/v) glucose and/or cellobiose as carbon and energy sources.

Transfer of DNA by Electroporation:

Plasmids pEC-K18mob2::bglRER, pEC-K18mob2::bglVH2, pEC-K18mob2::bglx, pEC-K18mob2::rer36840 and pEC-K18mob2::bglABC (Table 4) were transferred by electroporation applying the previously described protocol (Kalscheuer, Arenskotter, Steinbuchel 1999).

Cells of *R. opacus* PD630 and *R. erythropolis* DSM43066 were cultivated in mineral salts medium (MSM) as described by (Schlegel, H. G., Kaltwasser, H., and G. Gottschalk 1961). Carbon sources were added to liquid MSM as indicated in the text. Liquid cultures in Erlenmeyer flasks were incubated on a horizontal rotary shaker at an agitation of 110 rpm. Solid media were prepared by addition of 1.5% (wt/vol) agar/agar. Cells of *Escherichia coli* were cultivated at 37° C. in Lysogeny Broth (LB, (Bertani 2004)), cells of *Thermobifida fusca* DSM43792 were grown in Czapek peptone medium at 42° C. (Waksman 1961) and cells of *G. polyisoprenivorans* VH2 were grown in Standard I medium (Carl Roth, Karlsruhe, Germany). Antibiotics were applied according to (Sambrook, Fritsch, Manitas 1989) and as indicated in the text.

Only recombinant strains harboring pEC-K18mob2::bglABC exhibited significant growth on solid and liquid MSM with cellobiose as sole carbon sources, whereas all strains grew as expected with glucose. Based on this observations it was assumed that both the sugar transporters and the β-glucosidase are required for growth.

Example 8. β-Glucosidase (BGL) Activity Assays

The presence of functional active BGL in the recombinant strains was investigated by enzymatic analyses as described previously (Adin, Visick, Stabb 2008). Enzyme assays employing either the soluble protein fractions obtained from cells of the recombinant strains of *R. opacus* PD630 harboring pEC-K18mob2::bglABC (FIG. 10), pEC-K18mob2::bglx and pEC-K18mob2 (FIG. 9) or culture supernatants for pEC-K18mob2::bglRER and pEC-K18mob2::bglVH2, demonstrated the presence of active BGL in the strains *R. opacus* PD630 pEC-K18mob2::bglABC (FIG. 10) and pEC-K18mob2::bglx, whereas no BGL activity was detected in the soluble protein fractions and culture supernatants, respectively, of other strains (Table 4).

Example 9. Quantitative Analysis of Cellobiose

Analysis of medium cellobiose contents was done by HPLC. Culture media were centrifuged at 14.000×g to remove cells. Supernatants were filtered using Spartan 0.2 μm filters (Whatman, Dassel, Germany) and applied on a Eurokat Pb column (30GX350EKN, Knauer, Berlin, Germany) using water/acetonitrile 95:5 as eluent at 75° C. and a flow rate of 0.5 mL/min. The HPLC systems used comprises a Kontron system 522 pump and HPLC 560 autosampler (Kontron, Munchen, Germany) and a Sedex 80 LT-ELS detector (Sedere, Alfortville, France).

Example 10. Investigations of TAG Accumulation by Recombinant *R. opacus* Strains by GC Determination of the TAG content was performed as described in detail elsewhere (Brandl and others 1988; Waltermann and others 2000).

To investigate if the recombinant *R. opacus* strain can be used for TAG production from cellobiose, cells were cultivated under conditions permissive for TAG accumulation. The TAG contents of the cells were analyzed gas chromatographically as described in the materials and methods section. Samples were taken in the early stationary growth phase. GC analysis of the cells revealed a fatty acid content of 20.6±0.1% (wt/wt).

Figure 5:
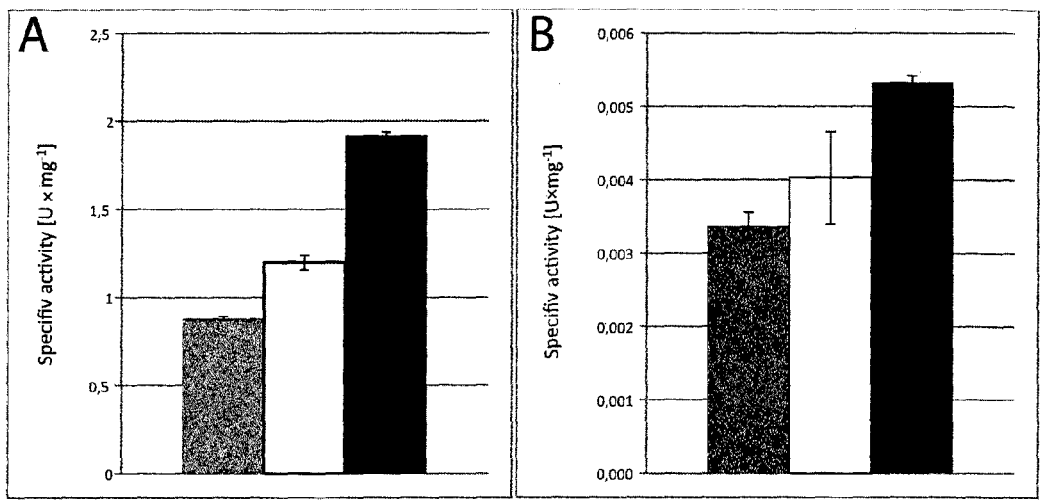
FIG. 5. Assay of specific β-glucosidase activity of the cell free lysates of engineered *R. opacus* PD630 strains at different temperatures (30° C., grey bar; 35° C., white bar; 40° C., black bar). A, *R. opacus* PD630 pEC-K18mob2::bglABC; B, *R. opacus* PD630 pEC-K18mob2::bglX. Activity is expressed as specific activity, one unit is defined as µmol×min−1 of converted pONPG. Error bars indicate standard deviations of triplicate measurements.

Example 11. Growth of the Recombinant *R. opacus* PD630 pEC-K18mob2::bglABC with Cellobiose as Sole Carbon Source All recombinant strains were tested for growth with cellobiose as sole carbon source in liquid and on solid MSM with glucose and/or cellobiose as sole carbon source. Only strain *R. opacus* PD630 pEC-K18mob2::bglABC (FIG. 10) was able to utilize cellobiose (FIG. 2), but the growth rates were far less than observed with glucose (data not shown). Additionally, HPLC analysis of culture supernatants revealed that cellobiose was only utilized by the growing strain *R. opacus* PD630 pEC-K18mob2::bglABC (FIG. 10), whereas cellobiose concentration remained static in all other cultures. Results are shown in FIG. 5.

Example 12. Producing Fatty Acid on Cellulosic Substrate

Degradation of Cellulose to Cellobiose:

Recombinant strains of *R. opacus* harboring plasmids pEC-K18mob2::cenA (FIG. 13), pEC-K18mob2::cenC (FIG. 15), pEC-K18mob2::cel6A(FIG. 11) and pJAM2::cenC::cex::cbhA were cultivated in MS-medium with 1% (wt/vol) birch cellulose, 1% (wt/vol) glucose and 75 µg×ml$^{-1}$ kanamycin on a rotary shaker (110 rpm) at 30° C. After 11 and 18 days, cellobiose and glucose contents of cultures were determined by HPLC (Culture media were centrifuged at 14.000×g to remove cells. Supernatants were filtered using Spartan 0.2 µm filters (Whatman, Dassel, Germany) and applied on a Eurokat Pb column (30GX350EKN, Knauer, Berlin, Germany) using water/acetonitrile 95:5 as eluent at 75° C. and a flow rate of 0.5 mL×min$^{-1}$. The HPLC systems used comprises a Kontron system 522 pump and HPLC 560 autosampler (Kontron, Munchen, Germany) and a Sedex 80 LT-ELS detector (Sedere, Alfortville, France)). Cellobiose concentrations reached 0.174±0.01% (wt/vol) after 11 days and 0.2±0% (wt/vol) after 18 days, respectively. Initially added glucose was completely depleted after 11 days already.

Fatty Acid Production:

Cells and residual birch cellulose were removed by centrifugation at 3500×g for 15 min and supernatants were filtered using Spartan 0.2 µm filters (Whatman, Dassel, Germany) and filled in new, sterile flasks. Cultures were then inoculated with 1% (vol/vol) of a *R. opacus* PD630 pEC-K18mob2::bglABC preculture and incubated at 30° C. on a rotary shaker until cellobiose was completely consumed (4 days). Cells were harvested by centrifugation (3500×g, 15 min), washed once with sterile saline solution (0.9% (wt/vol) NaCl) and freeze dried. Analysis of total fatty acid content was performed as described in detail elsewhere (Brandl, Gross, Lenz, & Fuller, 1988; Waltermann et al., 2000). A total fatty acid content of 15.15±0.2% (wt/wt) was determined, which is comparable to fatty acid contents achieved with propionic acid as substrate (18% (wt/wt)) (Alvarez et al. 1996)

Example 13. Analysis of Storage Lipids by TLC

Figure 6:
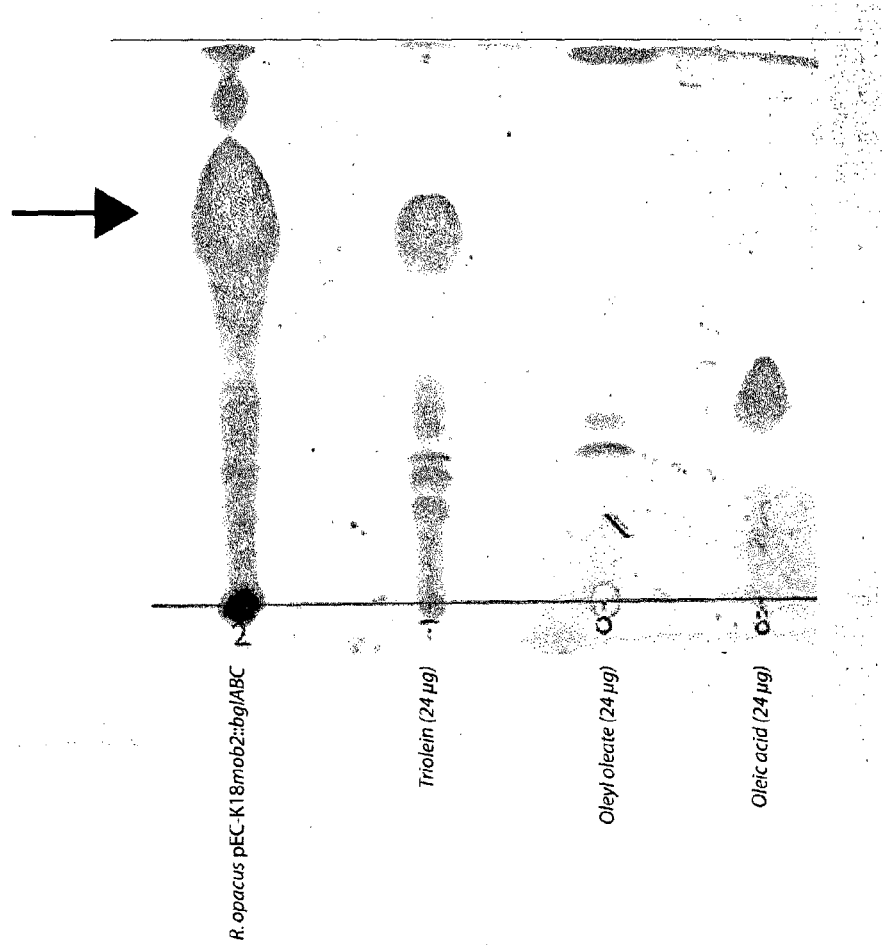
FIG. 6. TLC-analysis of storage lipids: 10-15 mg of lyophilized cell masses were extracted 2 times with 1 ml chloroform/methanol (2:1, vol/vol) for 1 h at room temperature. 80 µl of each extract and 25 µg triolein, oleyl oleate and oleic acid as standard substances were applied to a Silica 60 TLC plate (Merck, Darmstadt, Germany). The TLC was developed using hexane/diethyl ether/acetic acid (80:15:1, vol/vol/vol) as the solvent system and later on spots were visualized with sublimated iodine.

The analysis of intracellular lipids was done by thin-layer chromatography (TLC) as follows. Cells of *Rhodococcus* were lyophilized. Intracellular lipids were extracted 2 times from 10-15 mg (dry weight) cell material with 1 ml of chloroform-methanol (2:1 [vol/vol]). TLC analysis of lipid extracts was done using the solvent system hexane-diethyl etheracetic acid (80:20:1 [vol/vol/vol]). Lipids were visualized on the plates by staining with iodine vapor. Triolein, oleic acid, and oleyl oleate were used as reference substances for TAGs, FAs, and WEs, respectively. The results are shown as FIG. 6.

Example 14. Construction of Oleaginous Stain Capable of Utilizing Cellulosic Substrate The coding regions of the bglABC operon from *Thermobifida fusca* DSM43792, encoding two sugar transport proteins (BglA and B) and a cytoplasmic β-glucosidase (3.2.1.21) (BglC), and cenA, encoding an endoglucanase (EC 3.2.1.4) (CenA), from *Cellulomonas fimi* ATCC484, were amplified from genomic DNA using the primers FbglABC and RbglABC for bglABC and FcenA and RcenA for cenA. Both fragments were ligated to the *Escherichia coli/Corynebacterium* shuttle vector pEC-K18mob2 (Tauch et al., 2002) under control of the $P_{lac}$-promoter, yielding plasmid pEC-K18mob2::cenA::bglABC. The plasmid was transferred to *R. opacus* PD630 by electroporation as described by Kalscheuer et al. (Kalscheuer, Arenskötter, and Steinbüchel, 1999). Transformants were selected on selective LB plates containing 50 µg×ml$^{-1}$ kanamycin. Two transformants were randomly chosen and tested for their ability to degrade cellulose.

TABLE 5

Strains, plasmids and oligonucleotides used.

| Strain, plasmid or primer | Relevant characteristics | Source or reference |
|---|---|---|
| Strains | | |
| *E. coli* XL10 Gold | endA1 glnV44 recA1 thi-1 gyrA96 relA1 lac Hte Δ(mcrA)183 Δ(mcrCB-hsdSMR-mrr)173 tet$^R$ F'[proAB lacI$^q$ZΔM15 Tn10(Tet$^R$ Amy Cm$^R$)] | Stratagene |
| *R. opacus* PD630 | TAG producing strain | (Alvarez et al., 1996) |
| *C. fimi* ATCC484 | Cellobiose utilization | (Stackebrandt E., 1979) |
| *T. fusca* DSM43792 | Cellobiose utilization | (McCarthy, 1984) |
| Plasmids | | |
| pEC-K18mob2 | | (Tauch et al., 2002) |
| pEC-K18mob2::cenA::bglABC | cenA/bglABC as EcoRI/PstI fragment | this study |
| Oligonucleotides | | |
| FbglABC | AAATCTAGAAAAGAATTCGGCCGT CCTCTCTTCCATCTGACATCTGAC CTCTC | |

TABLE 5-continued

Strains, plasmids and oligonucleotides used.

| Strain, plasmid or primer | Relevant characteristics | Source or reference |
|---|---|---|
| RbglABC | AAACTGCAGGCCGCCGGGACGG CGAGATTTTGACCTATC | |
| FcenA | AAGAATTCGGGAGGTCCTTGATG TCCACCCGCAG | |
| RcenA | AAGAGCTCACCACCTGGCGTTGC GCGC | |

Example 15. Complete Cellulose Degradation by Recombinant Strains

Figure 7:
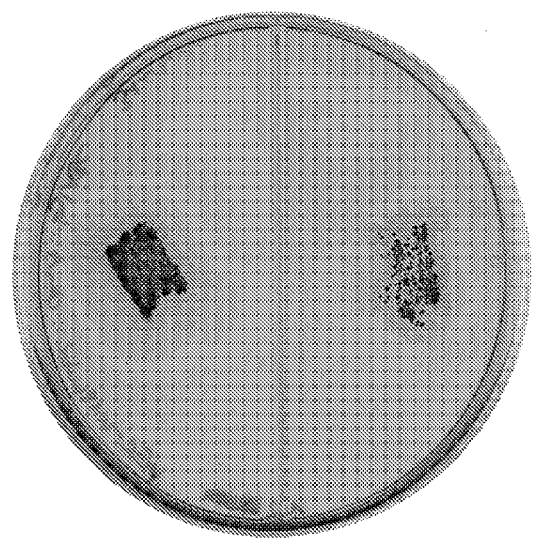
FIG. 7. Qualitative cellulase enzyme assay. Recombinant strains of *R. opacus* PD630 pEC-K18mob2::cenA::bglABC were transferred onto MSM plates with 0.5% (wt/vol) carboxymethyl cellulose (CMC) and 0.5% (wt/vol) glucose as carbon source. After 3 days, plates were stained with 0.1% (wt/vol) Congo Red and destained with 1 M NaCl.

Both recombinant R. opacus PD630 strains, R. opacus PD630 pEC-K18mob2::cenA::bglABC and R. opacus PD630 pEC-K18mob2::bglABC, were transferred onto MSM plates with 0.5% (wt/vol) CMC and 0.5% (wt/vol) glucose and incubated for 3 days at 30° C. Directly thereafter the plates were stained with Congo-Red (0.1% (wt/vol), and destained with 1 M NaCl until clear zones were visible. Activity of CenA and cellulose degradation capability was thereby confirmed (FIG. 7).

Figure 8:
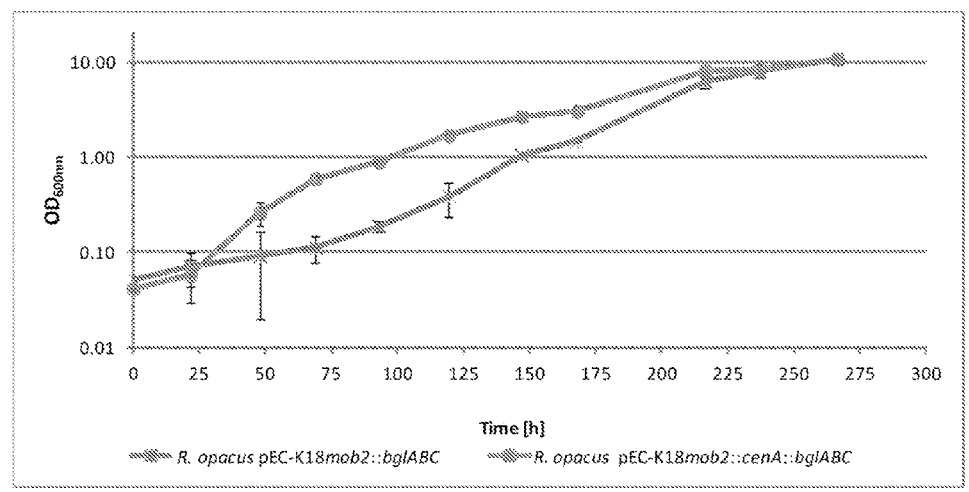
FIG. 8. Growth of the recombinant strain *R. opacus* PD630 pEC-K18mob2::bglABC and *R. opacus* PD630 pEC-K18mob2::cenA::bglABC. Cells were cultivated in liquid MSM containing 1.3% (wt/vol) cellobiose as sole carbon source. Error bars indicate standard deviations of triplicate measurements.

In parallel, both recombinant strains were cultivated in liquid MSM with 1.3% (wt/vol) cellobiose as sole carbon source; strain R. opacus PD630 pEC-K18mob2::bglABC (FIG. 10) served as control (FIG. 8). It was found that strain R. opacus PD630 pEC-K18mob2::cenA::bglABC exhibited a shorter lag-phase than strain R. opacus PD630 pEC-K18mob2::bglABC, whereas both strains reached a maximal optical density of about 12.5. Thus, both recombinant strains were able to use cellobiose.

Also, strain R. opacus PD630 pEC-K18mob2::cenA::bglABC was cultured in liquid MSM with 1% (wt/vol) birch cellulose or 1% (wt/vol) MCC as substrates. For the initial production of cellulase, 0.1% (wt/vol) glucose was added to the flasks, and cellobiose content of the medium was analyzed by HPLC as follows. Culture media were centrifuged at 14.000×g to remove cells. Supernatants were filtered using Spartan 0.2 µm filters (Whatman, Dassel, Germany) and applied on a Eurokat Pb column (30GX350EKN, Knauer, Berlin, Germany) using water/acetonitrile 95:5 as eluent at 75° C. and a flow rate of 0.5 mL×min$^{-1}$. The HPLC systems used comprises a Kontron system 522 pump and HPLC 560 autosampler (Kontron, Munchen, Germany) and a Sedex 80 LT-ELS detector (Sedere, Alfortville, France).

Analysis revealed that no cellobiose was accumulated but readily degraded by the recombinant strain R. opacus PD630 pEC-K18mob2::cenA::bglABC.

Quantitative Analysis of Cellobiose:

Analysis of medium cellobiose contents was done by HPLC. Culture media were centrifuged at 14.000×g to remove cells. Supernatants were filtered using Spartan 0.2 µm filters (Whatman, Dassel, Germany) and applied on a Eurokat Pb column (30GX350EKN, Knauer, Berlin, Germany) using water/acetonitrile 95:5 as eluent at 75° C. and a flow rate of 0.5 mL×min$^{-1}$. The HPLC systems used comprises a Kontron system 522 pump and HPLC 560 autosampler (Kontron, Munchen, Germany) and a Sedex 80 LT-ELS detector (Sedere, Alfortville, France).

Analysis of Fatty Acid Content of Recombinant R. opacus PD630 Cells by GC:

Determination of the fatty acid contents was performed as described in detail elsewhere (Brandl et al., 1988; Waltermann et al., 2000).

Investigations of Fatty Acid Accumulation by Recombinant R. opacus Strains:

To investigate if recombinant R. opacus harboring pEC-K18mob2::cenA::bglABC can be used for TAG production from cellobiose, cells were cultivated in MSM with 2.0% (wt/vol) cellobiose as sole carbon source and cultivated until the stationary phase was reached. The fatty acid contents of the cells were analyzed gas chromatographically as described earlier. GC analysis of the cells revealed total fatty acid contents of 32.46±0.00% (wt/wt) of the cell dry mass.

Figure 17:
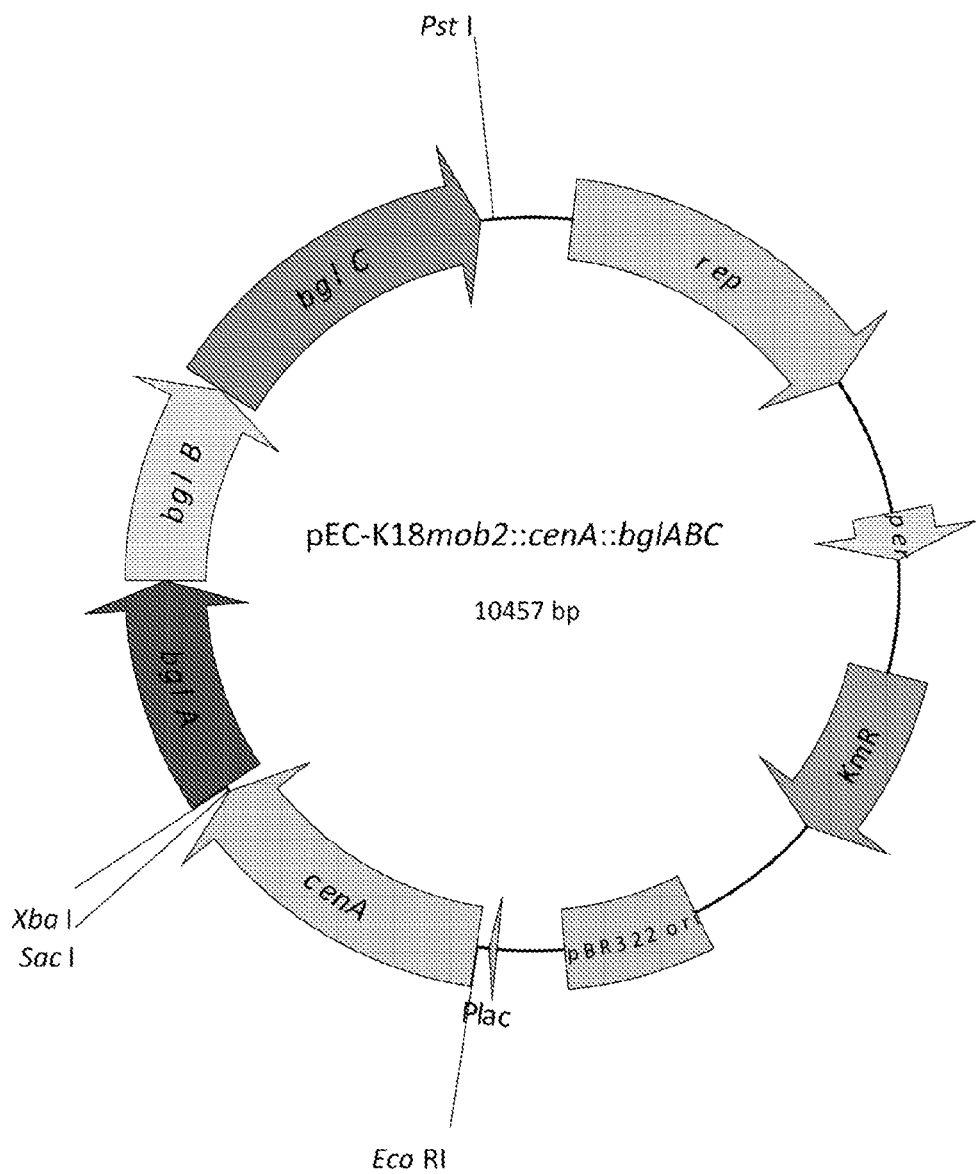
FIG. 17. Physical maps of the constructed plasmid pEC-K18mob2::cenA::bglABC. Relevant cleavage sites and structural genes are indicated (KmR, kanamycin resistance cassette, rep, origin of replication, per, positive effector of replication; cenA encoding endocellulase A (accession no. M15823) from *C. fimi*; bglAB encoding sugar transport proteins (accession no. YP_288996 and YP_288997) and bglC encoding a cytoplasmic β-glucosidase (accession no. YP_288998) from *T. fusca*.

Example 16. Construction of pCelluloseCB, Transfer to R. opacus and Test of Cellulase and β-Glucosidase-Activity The coding region of bglABC were amplified with the primers FbglABC2 and RbglABC2 with the plasmid pEC-K18mob2::bglABC as template. The DNA-fragment was subsequently ligated to the vector pEC-K18mob2::cenA by the XbaI/PstI restriction sites, yielding plasmid pEC-K18mob2::cenA::bglABC (FIG. 17).

Figure 18:
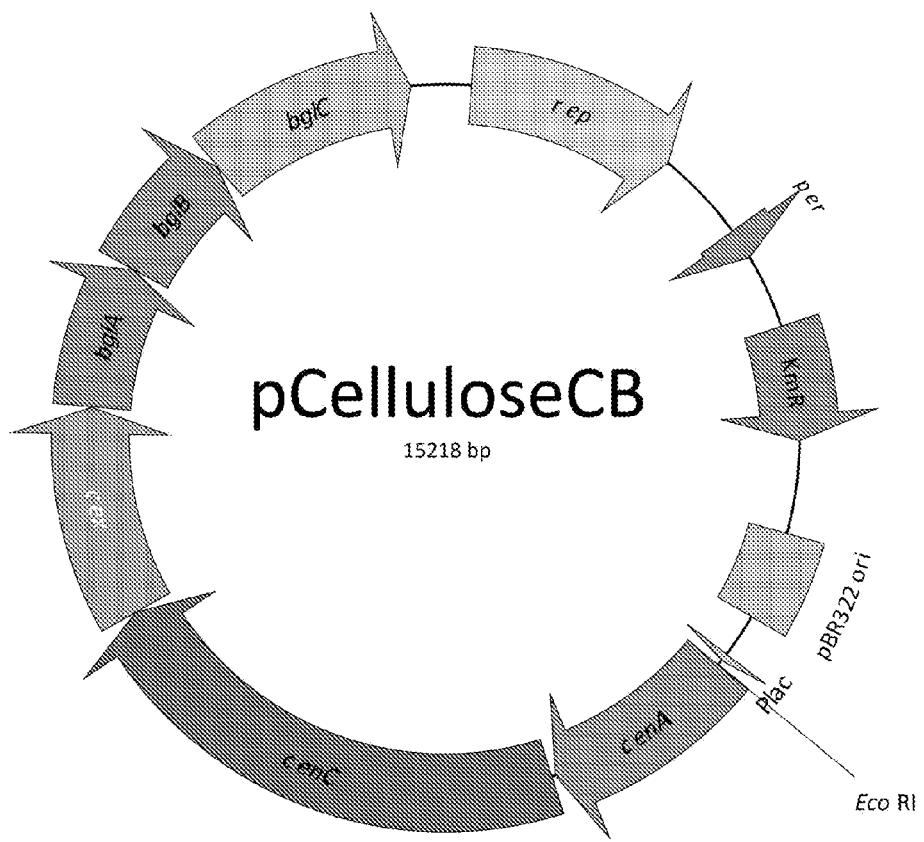
FIG. 18. Physical map of the constructed plasmid pCelluloseCB. Relevant cleavage sites and structural genes are indicated (KmR, kanamycin resistance cassette, rep, origin of replication, per, positive effector of replication; cenA encoding endocellulase A (accession no. M15823), cenC encoding endocellulase C (accession no. X57858.1), cex encoding exocellulase (accession no. M15824) from *C. fimi*; bglAB encoding sugar transport proteins (accession no.

The coding regions of cenC and cex were amplified with the primers FcenC and Rcex with plasmid pJAM2::cenC::cex::cbhA as template. The fragment was ligated to Plasmid pEC-K18mob2::cenA::bglABC after restriction with XbaI yielding plasmid pCelluloseCB (pEC-K18mob2:: cenA:: cenC::cex::bglABC, FIG. 18).

TABLE 6

Strains, plasmids and oligonucleotides used.

| Strain, plasmid or primer | Relevant characteristics | Source or reference |
|---|---|---|
| Strains | | |
| R. opacus PD630 | TAG producing strain | (Alvarez et al., 1996) |

TABLE 6-continued

Strains, plasmids and oligonucleotides used.

| Strain, plasmid or primer | Relevant characteristics | Source or reference |
|---|---|---|
| Plasmids | | |
| pEC-K18mob2::cenA::bglABC | cenA/bglABC as EcoRI/PstI fragment | |
| pEC-K18mob2::cenA | | |
| pJAM2::cenC::cex::cbhA | | |
| pCelluloseCB | | |
| Oligonucleotides | | this study |
| FbglABC2 | AAATCTAGAAAAGAATTCGGCCGT CCTCTCTTCCATCTGACATCTGAC CTCTC | this study |
| RbglABC2 | AAACTGCAGGCCGCCGGGACGG CGAGATTTTGACCTATC | this study |
| FcenC | AAATCTAGAAGGGGAGACAGAGT GGTTTCTCGCAGGTCATC | |
| Rcex | AAATCTAGATCAGCCGACCGTGC AGGG | |

Transfer to *R. opacus* and Test of Cellulase and β-Glucosidase-Activity:

Both plasmids pEC-K18mob2::cenA::bglABC and pCelluloseCB were transferred to *R. opacus* by electroporation. Recombinant strains of *R. opacus* PD630 pEC-K18mob2::cenA::bglABC and *R. opacus* PD630 pCelluloseCB were tested for their ability to degrade cellulose. For this, the strains were streaked out onto mineral salts medium plates with 0.5% (wt/vol) glucose, 0.5% (wt/vol) CMC and 50 μg×mL$^{-1}$ kanamycin. After 2 days of incubation at 30° C., the plates were stained with Congo Red (0.1% in H$_2$O) for 5 min and destained with 1 M NaCl until clear zones were visible. Both strains were able to degrade CMC, visible by clear zone formation (FIG. 19).

In addition, the activities of the employed endocellulases in the culture medium of recombinant strains *R. opacus* PD630 pEC-K18mob2::cenA::bglABC and *R. opacus* PD630 pCelluloseCB were tested quantitatively with Azo-CMC (Megazyme, Ireland) (FIG. 20). For *R. opacus* PD630 pEC-K18mob2::cenA::bglABC an activity of 0.25±0.02 U×mg$^{-1}$ could be determined, whereas the activity of *R. opacus* PD630 pCelluloseCB was 0.474±0.01 U×mg$^{-1}$.

Additionally, both strains were tested for their ability to utilize cellobiose as sole source of carbon and energy. For this, *R. opacus* PD630 pEC-K18mob2::cenA::bglABC and *R. opacus* PD630 pCelluloseCB were cultivated in liquid mineral salts medium with 1.3% (wt/vol) cellobiose as sole carbon source and 50 μg×mL$^{-1}$ kanamycin. Both strains exhibited growth with cellobiose as sole carbon source. Interestingly, the growth of strain *R. opacus* PD630 pEC-K18mob2::cenA::bglABC was improved compared to strain pEC-K18mob2::bglABC (FIG. 21).

The specific activity of the β-glucosidase BglC was also determined according to Adin et al. 2008, employing the soluble protein fractions obtained from cells of the recombinant strains of *R. opacus* PD630 harboring pEC-K18mob2::bglABC, pEC-K18mob2::cenA::bglABC or pCelluloseCB. This demonstrated the presence of an active β-glucosidase (0.881±0.011 U×mg$^{-1}$, 0.155±0.005 U×mg$^{-1}$ and 0.05±0.002 U×mg$^{-1}$, respectively, at 30° C.), whereas no activity was detected in the soluble protein fraction of the control strain PD630 harboring plasmid pEC-K18mob2 (FIG. 22).

Example 17. Production of Lipids Directly from Cellulose

Cells of *R. opacus* PD630 pCelluloseCB were cultivated in liquid mineral salts medium with 0.1% (wt/vol) glucose, 1% (wt/vol) Whatman-paper and 50 μg×mL$^{-1}$ kanamycin. After 14 days of incubation, the size of the cellulose particles had significantly decreased in the culture, whereas the particle size in the not inoculated control culture remained constant (data not shown). Additionally, cellobiose was directly metabolized by the cells and not accumulated in the medium, as was shown by HPLC analysis.

For the production of lipids directly from cellulose, recombinant cells of *R. opacus* pEC-K18mob2::cenA::bglABC were cultivated for 14 days in liquid mineral salts medium with 0.1% (wt/vol) of glucose, 1% (wt/vol) birch cellulose and 50 μg×mL$^{-1}$ kanamycin. For fluorescence microscopy, cells were stained with Nile Red for 20 min and immobilized by the addition of 2% (wt/vol) agarose. Lipid inclusions could be detected after excitation of the stained cells with 312 nm (data not shown). These analysis clearly indicated lipid storage from cellulose of the recombinant strains. By GC analysis, a fatty acid content of these cells of only 3-6.5% (wt/wt) could be determined, possibly a result of the poor separation of cells and remaining cellulosic substrate.

Example 18. Lipid Production Using Glucose or Cellobiose as a Carbon Source

Recombinant strains were cultivated both on solid and in liquid MSM (25) with 1% (wt/vol) glucose and/or cellobiose as carbon sources. Only recombinant strains harboring pEC-K18mob2::bglABC exhibited significant growth with cellobiose, whereas all other strains grew like the wild type. When *R. opacus* pEC-K18mob2::bglABC was cultivated in liquid MSM containing different concentrations (1, 1.7, or 4%, wt/vol) of cellobiose as sole carbon source, similar growth for all cultivation was observed ($\mu$=0.021-0.025) (FIG. 23). However, cultures with 1.7 and 4% (wt/vol) cellobiose exhibited a shorter lag phase and higher final optical densities compared to cultures with 1% (wt/vol) cellobiose.

HPLC Analysis of Medium Cellobiose:

Culture media were centrifuged at 14.000×g to remove cells. Supernatants were filtered using Spartan 0.2 µm filters (Whatman, Dassel, Germany) and applied on a Eurokat Pb column (30GX350EKN, Knauer, Berlin, Germany) using water/acetonitrile 95:5 as eluent at 75° C. and a flow rate of 1 mL×min$^{-1}$. The HPLC systems used comprises a Kontron system 522 pump and HPLC 560 autosampler (Kontron, Munchen, Germany) and a Sedex 80 LT-ELS detector (Sedere, Alfortville, France). Determination of cellobiose contents of the culture supernatants revealed that cellobiose was only utilized by growing cells of strain *R. opacus* PD630 pEC-K18mob2::bglABC. After 250 h cultivation, cellobiose was completely consumed in the 1% culture (FIG. 23), whereas in the 2 and 4% cultures, it was noted that glucose was accumulated in the medium after a cultivation period of 229 h, most likely as a result of cell death and subsequent leakage of BglC into the medium. Glucose levels reached up to 0.66±0.01% and 2.73±0.06% (wt/vol) in the 2 and 4% culture, respectively. The latter was higher than what could have been expected; however, the extenuated volume lead to accelerated evaporation of the medium. In general, growth of the recombinant *R. opacus* PD630 pEC-K18mob2::bglABC was considerably slower with cellobiose when compared with wild type *R. opacus* PD630 with sucrose or glucose ($\mu$=0.088 h$^{-1}$ and $\mu$=0.072 h$^{-1}$, respectively. Taking into account the fact that slow growth rates could also be observed in complex media, this provides evidence that expression of bglABC represents a strong metabolic burden to the cells, thereby decreasing consumption and growth rates. Interestingly, the additional stabilization of the plasmid by kanamycin resulted in a significantly shorter lag-phase of recombinant strains (data not shown).

Analysis of Storage Lipids:

Determination of the TAG content was performed as described in detail elsewhere. Qualitative analysis by TLC revealed a spot corresponding to the triolein standard for all three cellobiose cultivations. In addition, the fatty acid content of cells cultivated with 4% (wt/vol) cellobiose was determined at different time points (FIG. 23), which increased from 8.13±0.94% (wt/wt) at 167 h to 39.27±2.45% (wt/wt) after 229 h of cultivation and remained almost constant until the cultivation ended. These values are clearly lower than the lipid levels that can be achieved with sucrose or gluconate as carbon sources, but reflect on the one hand the basic metabolic rate for nitrogen accompanied by the long cultivation time, and on the other hand the elevated nitrogen content of the medium (0.1% (wt/vol), that was employed to stimulate cell growth.

REFERENCES

Adin D M, Visick K L, Stabb E V. 2008. Identification of a cellobiose utilization gene cluster with cryptic beta-galactosidase activity in vibrio fischeri. Appl Environ Microbiol 74(13):4059-69.

Alvarez H M and Steinbuchel A. 2002. Triacylglycerols in prokaryotic microorganisms. Appl Microbiol Biotechnol 60(4):367-76.

Alvarez H M, Mayer F, Fabritius D, Steinbuchel A. 1996. Formation of intracytoplasmic lipid inclusions by *rhodococcus opacus* strain PD630. Arch Microbiol 165(6):377-86.

Bertani G. 2004. Lysogeny at mid-twentieth century: P1, P2, and other experimental systems. J Bacteriol 186(3):595-600.

Birnboim H C and Doly J. 1979. A rapid alkaline extraction procedure for screening recombinant plasmid DNA. Nucleic Acids Res 7(6):1513-23.

Bokinsky G, Peralta-Yahya P P, George A, Holmes B M, Steen E J, Dietrich J, Soon Lee T, Tullman-Ercek D, Voigt C A, Simmons B A, et al. 2011. Synthesis of three advanced biofuels from ionic liquid-pretreated switchgrass using engineered *escherichia coli*. Proc Natl Acad Sci USA 108(50):19949-54.

Brandl H, Gross R A, Lenz R W, Fuller R C. 1988. *Pseudomonas oleovorans* as a source of poly(beta-hydroxyalkanoates) for potential applications as biodegradable polyesters. Appl Environ Microbiol 54(8):1977-82.

Goodfellow M, Alderson G, Lacey J. 1979. Numerical taxonomy of actinomadura and related actinomycetes. J Gen Microbiol 112(1):95-111.

Hanahan D. 1983. Studies on transformation of *escherichia coli* with plasmids. J Mol Biol 166(4):557-80.

Kalscheuer R, Arenskotter M, Steinbuchel A. 1999. Establishment of a gene transfer system for *rhodococcus opacus* PD630 based on electroporation and its application for recombinant biosynthesis of poly(3-hydroxyalkanoic acids). Appl Microbiol Biotechnol 52(4):508-15.

Linos A, Steinbuchel A, Sproer C, Kroppenstedt R M. 1999. *Gordonia polyisoprenivorans* sp. nov., a rubber-degrading actinomycete isolated from an automobile tyre. Int J Syst Bacteriol 49 Pt 4:1785-91.

Lynd L R, van Zyl W H, McBride J E, Laser M. 2005. Consolidated bioprocessing of cellulosic biomass: An update. Curr Opin Biotechnol 16(5):577-83.

McCarthy A J&C, T. 1984. A taxonomic study of thermomonospora and other monosporic actinomycetes. J Gen Microbiol 130:5-25.

Mosier N S, Hall P, Ladisch C M, Ladisch M R. 1999. Reaction kinetics, molecular action, and mechanisms of cellulolytic proteins. Adv Biochem Eng Biotechnol 65:23-40.

Sambrook J, Fritsch E F, Manitas T. 1989. Molecular cloning: A laboratory manual, 2nd edition.

Schlegel, H.G., Kaltwasser, H., and G. Gottschalk. 1961. Ein submersverfahren zur kultur wasserstoffoxidierender bakterien: Wachstumsphysiologische untersuchungen. Arch Mikrobiol 38:209-22.

Spiridonov N A and Wilson D B. 2001. Cloning and biochemical characterization of BglC, a beta-glucosidase from the cellulolytic actinomycete thermobifida *fusca*. Curr Microbiol 42(4):295-301.

Tauch A, Kirchner O, Loffler B, Gotker S, Puhler A, Kalinowski J. 2002. Efficient electrotransformation of *corynebacterium diphtheriae* with a mini-replicon derived from the *corynebacterium glutamicum* plasmid pGA1. Curr Microbiol 45(5):362-7.

Waksman S A. 1961. The actinomycetes. II.

Waltermann M, Luftmann H, Baumeister D, Kalscheuer R, Steinbuchel A. 2000. *Rhodococcus opacus* strain PD630 as a new source of high-value single-cell oil? isolation and characterization of triacylglycerols and other storage lipids. Microbiology 146 (Pt 5)(Pt 5):1143-9.

Yang M, Luoh S M, Goddard A, Reilly D, Henzel W, Bass S. 1996. The bglX gene located at 47.8 min on the *escherichia coli* chromosome encodes a periplasmic beta-glucosidase. Microbiology 142 (Pt 7)(Pt 7):1659-65.

Beguin, P. (1983). Detection of cellulase activity in polyacrylamide gels using congo red-stained agar replicas. Analytical Biochemistry, 131(2), 333-336.

Guo Z., Arfman N., Ong E., Gilkes N. R., Kilburn D. G., Warren R. A. J., et al. (1988). Leakage of *Cellulomonas fimi* cellulases from *Escherichia coli*. FEMS Microbiology Letters, 49, 279-283.

Petersen, T. N., Brunak, S., von Heijne, G., & Nielsen, H. (2011). SignalP 4.0: Discriminating signal peptides from transmembrane regions. Nature Methods, 8(10), 785-786.

Stackebrandt E, K. O. (1979). Taxonomy of the genus *Cellulomonas*, based on phenotypic characters and deoxyribonucleic acid-deoxyribonucleic acid homology, and proposal of seven neotype strains. International Journal of Systematic and Evolutionary Microbiology, 29(4), 273-282.

Triccas, J. A., Parish, T., Britton, W. J., & Gicquel, B. (1998). An inducible expression system permitting the efficient purification of a recombinant antigen from *Mycobacterium smegmatis*. FEMS Microbiology Letters, 167 (2), 151-156.

Wong, W. K., Gerhard, B., Guo, Z. M., Kilburn, D. G., Warren, A. J., & Miller, R. C., Jr. (1986). Characterization and structure of an endoglucanase gene cenA of *Cellulomonas fimi*. Gene, 44(2-3), 315-324.

Stackebrandt E, Kandler O. 1979. Taxonomy of the genus *Cellulomonas*, based on phenotypic characters and deoxyribonucleic acid-deoxyribonucleic acid homology, and proposal of seven neotype strains. International Journal of Systematic and Evolutionary Microbiology 29 (4): 273-82.

The invention claimed is:

1. An oleaginous bacterial cell that accumulates at least 10% (w/w) of its biomass dry weight as lipids after cultivation in conditions for lipid production, wherein genes encoding at least one endocellulase, at least one exocellulase, at least one cellobiase, and at least one ABC type transporter capable of facilitating cellobiose uptake operably linked to a suitable promoter sequence have been introduced.

2. The oleaginous bacterial cell according to claim 1, wherein the cell belongs to genus *Rhodococcus*.

3. The oleaginous bacterial cell according to claim 1, wherein further the lipid production pathway has been modified.

4. A method for lipid production comprising the steps of
   (a) providing a culturing medium where at least part of the carbon source is in cellulosic form;
   (b) providing a bacterial cell capable of expressing and secreting one or more cellulolytic activity/cellulolytic activities;
   (c) contacting said medium and said cell;
   (d) cultivating said medium and said cell in conditions allowing expression of said cellulolytic activities;
   (e) providing (i) the cellulolytic bacterial cell of (b) being oleaginous, or (ii) another oleaginous bacterial cell genetically modified to use cellobiose as a carbon source;
   (f) contacting the culturing medium of step (c) or the spent culturing medium obtained from step (c) with said cell;
   (g) cultivating said cell in conditions allowing lipid production; and
   (h) recovering the lipids,
   wherein at least one of the bacterial cell secreting cellulolytic activity in step (b) and the oleaginous bacterial cell of step (e) is the oleaginous bacterial cell of claim 1.

5. The method according to claim 4, wherein the bacterial cell secreting cellulolytic activity in step (b) and the oleaginous bacterial cell of step (e) are cultivated sequentially.

6. The method according to claim 4, wherein the bacterial cell secreting cellulolytic activity in step (b) and the oleaginous bacterial cell of step (e) are cultivated simultaneously in the same culturing medium.

7. The method according to claim 4, wherein the bacterial cell secreting cellulolytic activity in step (b) secretes endoglucanase and exoglucanase activities and the oleaginous bacterial cell according to step (e) expresses cellobiase activity.

8. The method according to claim 4, wherein the oleaginous bacterial cell according to step (e) further expresses transporter(s) for cellobiose intake.

9. The method according to claim 4, wherein the bacterial cell secreting cellulolytic activity in step (b) and the oleaginous bacterial cell of step (e) both are the oleaginous bacterial cell of claim 1.

10. The method according to claim 4, wherein at least 10%, preferably 30% of the carbon source is in cellulosic form.

11. The method according to claim 4, wherein the carbon source is pretreated cellulose.

12. A method for lipid production comprising the steps of
   (a) contacting the oleaginous bacterial cell of claim 1 with a culture medium wherein at least part of the carbon source is cellobiose, preferably cellobiose from hydrolysis of cellulosic substrate;
   (b) cultivating the cell in conditions allowing for the lipid production; and
   (c) recovering the lipids.

13. A method for lipid production comprising cultivating the oleaginous bacterial cell according to claim 1 in a culture medium under conditions allowing for the lipid production and recovering the lipids.

14. The oleaginous bacterial cell according to claim 1, wherein the cell is a modified *Rhodococcus opacus*.

15. An oleaginous bacterial cell that accumulates at least 10% (w/w) of its biomass dry weight as lipids after cultivation in conditions for lipid production, wherein genes encoding at least one endocellulase, at least one exocellulase, at least one cellobiase, and at least one ABC type transporter capable of facilitating cellobiose uptake operably linked to a suitable promoter sequence have been introduced, and
   wherein:
   (i) the endocellulase is a polypeptide comprising an amino acid sequence having at least 80% identity to SEQ ID NO: 1 (CenA), SEQ ID NO: 3 (CenB), SEQ ID NO: 5 (CenC) or SEQ ID NO: 11 (Ce16A);
   (ii) the exocellulase is a polypeptide comprising an amino acid sequence having at least 80% identity to SEQ ID NO: 9 (Cex) or SEQ ID NO: 7 (CbhA);
   (iii) the cellobiase is a polypeptide comprising an amino acid sequence having at least 80% identity to polypeptide SEQ ID NO: 17 (BglC); and
   (iv) the ABC type transporter is a polypeptide comprising an amino acid sequence having at least 80% identity to SEQ ID NO: 13 (Bg1A) or SEQ ID NO: 15 (Bg1B).

16. The oleaginous bacterial cell according to claim 15, wherein:
   (i) the endocellulase is a polypeptide comprising an amino acid sequence having at least 90% identity to SEQ ID NO: 1 (CenA), SEQ ID NO: 3 (CenB), SEQ ID NO: 5 (CenC) or SEQ ID NO: 11 (Ce16A);
   (ii) the exocellulase is a polypeptide comprising an amino acid sequence having at least 90% identity to SEQ ID NO: 9 (Cex) or SEQ ID NO: 7 (CbhA);
   (iii) the cellulobiose is a polypeptide comprising an amino acid sequence having at least 90% identity to SEQ ID NO: 17 (BglC); and
   (iv) the ABC type transporter is a polypeptide comprising an amino acid sequence having at least 90% identity to SEQ ID NO: 13 (Bg1A) or SEQ ID NO: 15 (Bg1B).

17. The oleaginous bacterial cell according to claim 15, wherein:
   (i) the endocellulase is a polypeptide comprising an amino acid sequence having at least 95% identity to SEQ ID NO: 1 (CenA), SEQ ID NO: 3 (CenB), SEQ ID NO: 5 (CenC) or SEQ ID NO: 11 (Ce16A);
   (ii) the exocellulase is a polypeptide comprising an amino acid sequence having at least 95% identity to SEQ ID NO: 9 (Cex) or SEQ ID NO: 7 (CbhA);
   (iii) the cellulobiose is a polypeptide comprising an amino acid sequence having at least 95% identity to SEQ ID NO: 17 (BglC); and
   (iv) the ABC type transporter is a polypeptide comprising an amino acid sequence having at least 95% identity to SEQ ID NO: 13 (Bg1A) or SEQ ID NO: 15 (Bg1B).

18. The oleaginous bacterial cell according to claim 15, wherein:
   (i) the endocellulase is a polypeptide comprising an amino acid selected from the group consisting of SEQ ID NO: 1 (CenA), SEQ ID NO: 3 (CenB), SEQ ID NO: 5 (CenC) and SEQ ID NO: 11 (Ce16A);

(ii) the exocellulase is a polypeptide comprising an amino acid selected from the group consisting of SEQ ID NO: 9 (Cex) and SEQ ID NO: 7 (CbhA); and (iii) the cellulobiose is a polypeptide comprising an amino acid sequence of SEQ ID NO: 17 (BglC); and (iv) the ABC type transporter take is a polypeptide comprising an amino acid sequence of SEQ ID NO: 13 (Bg1A) or SEQ ID NO: 15 (Bg1B).

19. A method for lipid production comprising the steps of (a) contacting the oleaginous bacterial cell of claim 15 with a culture medium wherein at least part of the carbon source is cellobiose, preferably cellobiose from hydrolysis of cellulosic substrate;

(b) cultivating the cell in conditions allowing for the lipid production; and (c) recovering the lipids.

20. A method for lipid production comprising the steps of (a) contacting the oleaginous bacterial cell of claim 16 with a culture medium wherein at least part of the carbon source is cellobiose, preferably cellobiose from hydrolysis of cellulosic substrate;

(b) cultivating the cell in conditions allowing for the lipid production; and (c) recovering the lipids.

21. A method for lipid production comprising the steps of (a) contacting the oleaginous bacterial cell of claim 17 with a culture medium wherein at least part of the carbon source is cellobiose, preferably cellobiose from hydrolysis of cellulosic substrate;

(b) cultivating the cell in conditions allowing for the lipid production; and (c) recovering the lipids.

22. A method for lipid production comprising the steps of (a) contacting the oleaginous bacterial cell of claim 18 with a culture medium wherein at least part of the carbon source is cellobiose, preferably cellobiose from hydrolysis of cellulosic substrate;

(b) cultivating the cell in conditions allowing for the lipid production; and (c) recovering the lipids.

* * * * *

SEQUENCE LISTING

```
<160> NUMBER OF SEQ ID NOS: 44

<210> SEQ ID NO 1
<211> LENGTH: 449
<212> TYPE: PRT
<213> ORGANISM: Cellulomonas fimi

<400> SEQUENCE: 1

Met Ser Thr Arg Arg Thr Ala Ala Ala Leu Leu Ala Ala Ala Ala Val
1               5                   10                  15

Ala Val Gly Gly Leu Thr Ala Leu Thr Thr Ala Ala Gln Ala Ala
            20                  25                  30

Pro Gly Cys Arg Val Asp Tyr Ala Val Thr Asn Gln Trp Pro Gly Gly
        35                  40                  45

Phe Gly Ala Asn Val Thr Ile Thr Asn Leu Gly Asp Pro Val Ser Ser
    50                  55                  60

Trp Lys Leu Asp Trp Thr Tyr Thr Ala Gly Gln Arg Ile Gln Gln Leu
65                  70                  75                  80

Trp Asn Gly Thr Ala Ser Thr Asn Gly Gly Gln Val Ser Val Thr Ser
                85                  90                  95

Leu Pro Trp Asn Gly Ser Ile Pro Thr Gly Gly Thr Ala Ser Phe Gly
            100                 105                 110

Phe Asn Gly Ser Trp Ala Gly Ser Asn Pro Thr Pro Ala Ser Phe Ser
        115                 120                 125

Leu Asn Gly Thr Thr Cys Thr Gly Thr Val Pro Thr Thr Ser Pro Thr
    130                 135                 140

Pro Thr Pro Thr Pro Thr Pro Thr Pro Thr Pro Thr Pro Thr Pro
145                 150                 155                 160

Thr Pro Thr Pro Thr Val Thr Pro Gln Pro Thr Ser Gly Phe Tyr Val
                165                 170                 175

Asp Pro Thr Thr Gln Gly Tyr Arg Ala Trp Gln Ala Ala Ser Gly Thr
            180                 185                 190

Asp Lys Ala Leu Leu Glu Lys Ile Ala Leu Thr Pro Gln Ala Tyr Trp
        195                 200                 205

Val Gly Asn Trp Ala Asp Ala Ser His Ala Gln Ala Glu Val Ala Asp
    210                 215                 220

Tyr Thr Gly Arg Ala Val Ala Ala Gly Lys Thr Pro Met Leu Val Val
225                 230                 235                 240
```

```
Tyr Ala Ile Pro Gly Arg Asp Cys Gly Ser His Ser Gly Gly Gly Val
            245                 250                 255

Ser Glu Ser Glu Tyr Ala Arg Trp Val Asp Thr Val Ala Gln Gly Ile
        260                 265                 270

Lys Gly Asn Pro Ile Val Ile Leu Glu Pro Asp Ala Leu Ala Gln Leu
            275                 280                 285

Gly Asp Cys Ser Gly Gln Gly Asp Arg Val Gly Phe Leu Lys Tyr Ala
        290                 295                 300

Ala Lys Ser Leu Thr Leu Lys Gly Ala Arg Val Tyr Ile Asp Ala Gly
305                 310                 315                 320

His Ala Lys Trp Leu Ser Val Asp Thr Pro Val Asn Arg Leu Asn Gln
                325                 330                 335

Val Gly Phe Glu Tyr Ala Val Gly Phe Ala Leu Asn Thr Ser Asn Tyr
            340                 345                 350

Gln Thr Thr Ala Asp Ser Lys Ala Tyr Gly Gln Gln Ile Ser Gln Arg
        355                 360                 365

Leu Gly Gly Lys Lys Phe Val Ile Asp Thr Ser Arg Asn Gly Asn Gly
    370                 375                 380

Ser Asn Gly Glu Trp Cys Asn Pro Arg Gly Arg Ala Leu Gly Glu Arg
385                 390                 395                 400

Pro Val Ala Val Asn Asp Gly Ser Gly Leu Asp Ala Leu Leu Trp Val
                405                 410                 415

Lys Leu Pro Gly Glu Ser Asp Gly Ala Cys Asn Gly Gly Pro Ala Ala
            420                 425                 430

Gly Gln Trp Trp Gln Glu Ile Ala Leu Glu Met Ala Arg Asn Ala Arg
        435                 440                 445

Trp

<210> SEQ ID NO 2
<211> LENGTH: 1350
<212> TYPE: DNA
<213> ORGANISM: Cellulomonas fimi

<400> SEQUENCE: 2
atgtccaccc gcagaaccgc cgcagcgctg ctggcggccg cggccgtcgc cgtcggcggt      60
ctgaccgccc tcaccaccac cgccgcgcag gcggctcccg gctgccgcgt cgactacgcc     120
gtcaccaacc agtggcccgg cggcttcggc gccaacgtca cgatcaccaa cctcggcgac     180
cccgtctcgt cgtggaagct cgactggacc tacaccgcag ccagcggat ccagcagctg      240 tggaacggca ccgcgtcgac caacggcggc caggtctccg tcaccagcct gcctggaac      300 ggcagcatcc cgaccggcgg cacggcgtcg ttcgggttca acggctcgtg ggccgggtcc     360
aacccgacgc cggcgtcgtt ctcgctcaac ggcaccacct gcacgggcac cgtgccgacg     420 accagccccca cgccgacccc gacgccgacg accccacgc cgacgccgac cccgaccccc      480 accccacgc cgacggtcac gccgcagccg ccagcggct ctacgtcga cccgacgacg        540 cagggctacc gcgcgtggca ggccgcgtcc ggcacggaca aggcgctgct cgagaagatc     600
gcgctcaccc cgcaggcgta ctgggtcggc aactgggccg acgcgtcgca gcgcaggcc      660 gaggtcgccg actacaccgg ccgcgccgtc gcggccggga agacgccgat gctcgtcgtc     720
tacgcgatcc cgggccgcga ctgcggctcg cactccggcg gtggtgtgtc cgagtccgag     780
tacgcgcgct gggtcgacac cgtcgcgcag ggcatcaagg gcaacccgat cgtgatcctc     840
gagcccgacg cgctcgcgca gctcggcgac tgctccggcc agggtgaccg cgtcggcttc     900
```

-continued

```
ctcaagtacg ccgccaagtc gctcaccctc aagggcgcgc gcgtctacat cgacgcgggc    960
cacgcgaagt ggctgtcggt cgacacgccg gtgaaccgcc tcaaccaggt cggcttcgag   1020
tacgcggtgg gcttcgcgct caacacgtcg aactaccaga cgacggcgga cagcaaggcg   1080
tacggccagc agatctcgca gcggctgggc ggcaagaagt tcgtcatcga cacctcgcgc   1140
aacggcaacg gctcgaacgg cgagtggtgc aacccgcgcg gccgcgcgct cggcgaacgc   1200
ccggtcgcgg tgaacgacgg ctccggcctg gacgcgctcc tgtgggtcaa gctgcccggc   1260
gagtccgacg gcgcgtgcaa cggcggcccg gccgccggcc agtggtggca ggagatcgcc   1320
ctggagatgg cgcgcaacgc caggtggtga                                    1350
```

```
<210> SEQ ID NO 3
<211> LENGTH: 1045
<212> TYPE: PRT
<213> ORGANISM: Cellulomonas fimi

<400> SEQUENCE: 3

Met Leu Arg Gln Val Pro Arg Thr Leu Val Ala Gly Gly Ser Ala Leu
1               5                   10                  15

Ala Val Ala Val Gly Val Leu Val Ala Pro Leu Ala Thr Gly Ala Ala
            20                  25                  30

Ala Ala Pro Thr Tyr Asn Tyr Ala Glu Ala Leu Gln Lys Ser Met Phe
        35                  40                  45

Phe Tyr Gln Ala Gln Arg Ser Gly Asp Leu Pro Ala Asp Phe Pro Val
    50                  55                  60

Ser Trp Arg Gly Asp Ser Gly Leu Thr Asp Gly Ala Asp Val Gly Lys
65                  70                  75                  80

Asp Leu Thr Gly Gly Trp Tyr Asp Ala Gly Asp His Val Lys Phe Gly
                85                  90                  95

Phe Pro Met Ala Phe Ser Ala Thr Met Leu Ala Trp Gly Ala Ile Glu
            100                 105                 110

Ser Pro Thr Gly Tyr Ser Lys Ala Gly Ser Leu Asp Glu Leu Lys Asp
        115                 120                 125

Asn Leu Arg Phe Val Ser Asp Tyr Phe Val Lys Ala His Thr Ala Pro
    130                 135                 140

Asn Glu Leu Tyr Val Gln Val Gly Asp Gly Glu Ala Asp His Lys Trp
145                 150                 155                 160

Trp Gly Pro Ala Glu Val Met Thr Met Ala Arg Pro Ser His Lys Ile
                165                 170                 175

Ser Ala Ser Cys Pro Gly Ser Asp Val Ala Ala Glu Thr Ala Ala Ala
            180                 185                 190

Leu Ala Ser Ser Ala Ile Val Leu Lys Gly Asp Asp Pro Ala Tyr Ala
        195                 200                 205

Ala Thr Leu Val Ser His Ala Lys Gln Leu Tyr Thr Phe Ala Asp Thr
    210                 215                 220

Tyr Arg Gly Ala Tyr Ser Asp Cys Val Thr Ala Ala Ser Ala Tyr Tyr
225                 230                 235                 240

Lys Ser Trp Ser Gly Tyr Gln Asp Glu Leu Val Trp Gly Ala Tyr Trp
                245                 250                 255

Leu Tyr Lys Ala Thr Gly Asp Ala Thr Tyr Leu Ala Lys Ala Glu Ala
            260                 265                 270

Glu Tyr Asp Lys Leu Gly Thr Glu Asn Gln Ser Thr Thr Arg Ser Tyr
        275                 280                 285

Lys Trp Thr Ile Ala Trp Asp Asn Lys Gln Phe Gly Thr Tyr Ala Leu
```

```
         290                 295                 300
Leu Ala Met Glu Thr Gly Lys Gln Lys Tyr Val Asp Asp Ala Asn Arg
305                 310                 315                 320

Trp Leu Asp Tyr Trp Thr Val Gly Val Asn Gly Gln Lys Val Pro Tyr
                325                 330                 335

Ser Pro Gly Gly Gln Ala Val Leu Asp Ser Trp Gly Ala Leu Arg Tyr
                340                 345                 350

Ala Ala Asn Thr Ser Phe Val Ala Leu Val Tyr Ser Asp Trp Met Thr
                355                 360                 365

Asp Ala Thr Arg Lys Ala Arg Tyr His Asp Phe Gly Val Arg Gln Ile
                370                 375                 380

Asn Tyr Ala Leu Gly Asp Asn Pro Arg Ser Ser Tyr Val Val Gly
385                 390                 395                 400

Phe Gly Ala Asn Pro Pro Thr Ala Pro His His Arg Thr Ala His Gly
                405                 410                 415

Ser Trp Leu Asp Ser Ile Thr Thr Pro Ala Gln Ser Arg His Val Leu
                420                 425                 430

Tyr Gly Ala Leu Val Gly Gly Pro Gly Ser Pro Asn Asp Ala Tyr Thr
                435                 440                 445

Asp Ser Arg Gln Asp Tyr Val Ala Asn Glu Val Ala Thr Asp Tyr Asn
                450                 455                 460

Ala Gly Phe Thr Ser Ala Leu Ala Arg Leu Val Glu Glu Tyr Gly Gly
465                 470                 475                 480

Thr Pro Leu Ala Ser Phe Pro Thr Pro Glu Gln Pro Asp Gly Asp Gln
                485                 490                 495

Leu Phe Val Glu Ala Met Leu Asn Gln Pro Pro Ser Gly Thr Phe Thr
                500                 505                 510

Glu Val Lys Ala Met Ile Arg Asn Gln Ser Ala Phe Pro Ala Arg Ser
                515                 520                 525

Leu Lys Asn Ala Lys Val Arg Tyr Trp Phe Thr Thr Asp Gly Phe Ala
                530                 535                 540

Ala Ser Asp Val Thr Leu Ser Ala Asn Tyr Ser Glu Cys Gly Ala Gln
545                 550                 555                 560

Ser Gly Lys Gly Val Ser Ala Gly Gly Thr Leu Gly Tyr Val Glu Leu
                565                 570                 575

Ser Cys Val Gly Gln Asp Ile His Pro Gly Gly Gln Ser Gln His Arg
                580                 585                 590

Arg Glu Ile Gln Phe Arg Leu Thr Gly Pro Ala Gly Trp Asn Pro Ala
                595                 600                 605

Asn Asp Pro Ser Tyr Thr Gly Leu Thr Gln Thr Ala Leu Ala Lys Ala
                610                 615                 620

Ser Ala Ile Thr Leu Tyr Asp Gly Ser Thr Leu Val Trp Gly Lys Glu
625                 630                 635                 640

Pro Thr Gly Thr Thr Thr Asp Thr Thr Pro Thr Thr Pro Gly Thr
                645                 650                 655

Pro Val Ala Thr Gly Val Thr Val Gly Ala Ser Leu Ser Trp Ala
                660                 665                 670

Ala Ser Thr Asp Ala Gly Ser Gly Val Ala Gly Tyr Glu Leu Tyr Arg
                675                 680                 685

Val Gln Gly Thr Thr Gln Thr Leu Val Gly Thr Thr Ala Ala Ala
                690                 695                 700

Tyr Ile Leu Arg Asp Leu Thr Pro Gly Thr Ala Tyr Ser Tyr Val Val
705                 710                 715                 720
```

```
Lys Ala Lys Asp Val Ala Gly Asn Val Ser Ala Ala Ser Ala Ala Val
            725                 730                 735

Thr Phe Thr Thr Asp Thr Thr Gly Glu Thr Glu Pro Pro Thr Thr Pro
            740                 745                 750

Gly Thr Pro Val Ala Ser Ala Val Thr Ser Thr Gly Ala Thr Leu Ala
            755                 760                 765

Trp Ala Pro Ser Thr Gly Asp Pro Ala Val Ser Gly Tyr Asp Val Leu
            770                 775                 780

Arg Val Gln Gly Thr Thr Thr Val Ala Gln Thr Thr Val Pro
785                 790                 795                 800

Thr Val Thr Leu Ser Gly Leu Thr Pro Ser Thr Ala Tyr Thr Tyr Ala
            805                 810                 815

Val Arg Ala Lys Asn Val Ala Gly Asp Val Ser Ala Leu Ser Ala Pro
            820                 825                 830

Val Thr Phe Thr Thr Ala Ala Pro Pro Val Asp Thr Val Ala Pro Thr
            835                 840                 845

Val Pro Gly Thr Pro Val Ala Ser Asn Val Ala Thr Thr Gly Ala Thr
            850                 855                 860

Leu Thr Trp Thr Ala Ser Thr Asp Ser Gly Ser Gly Leu Ala Gly
865                 870                 875                 880

Tyr Glu Val Leu Arg Val Ser Gly Thr Thr Gln Thr Leu Val Ala Ser
            885                 890                 895

Pro Thr Thr Ala Thr Val Ala Leu Ala Gly Leu Thr Pro Ala Thr Ala
            900                 905                 910

Tyr Ser Tyr Val Val Arg Ala Lys Asp Gly Ala Gly Asn Val Ser Ala
            915                 920                 925

Val Ser Ser Pro Val Thr Phe Thr Thr Leu Pro Val Thr Ser Thr Pro
            930                 935                 940

Ser Cys Thr Val Val Tyr Ser Thr Asn Ser Trp Asn Val Gly Phe Thr
945                 950                 955                 960

Gly Ser Val Lys Ile Thr Asn Thr Gly Thr Thr Pro Leu Thr Trp Thr
            965                 970                 975

Leu Gly Phe Ala Phe Pro Ser Gly Gln Gln Val Thr Gly Gly Trp Ser
            980                 985                 990

Ala Thr Trp Ser Gln Thr Gly Thr  Thr Val Thr Ala Thr Gly Leu Ser
            995                 1000                 1005

Trp Asn  Ala Thr Leu Gln Pro  Gly Gln Ser Thr Asp  Ile Gly Phe
   1010                 1015                  1020

Asn Gly  Ser His Pro Gly Thr  Asn Thr Asn Pro Ala  Ser Phe Thr
   1025                 1030                  1035

Val Asn  Gly Glu Val Cys Gly
   1040                 1045

<210> SEQ ID NO 4
<211> LENGTH: 3138
<212> TYPE: DNA
<213> ORGANISM: Cellulomonas fimi

<400> SEQUENCE: 4
atgctccgcc aagtcccacg cacgctcgtc gcgggtggct ccgccctcgc cgtcgccgtc    60
ggggtgctcg tcgccccgct cgcgaccggc gcggccgccg cgcccaccta caactacgcc   120
gaggccctgc agaagtcgat gttcttctac caggcgcagc gctccggcga cctgcccgcc   180
gacttcccgg tctcctggcg cggcgactcc ggcctgaccg acggcgccga cgtcggcaag   240
```

```
gacctcaccg gcggctggta cgacgccggc gaccacgtga agttcggctt cccgatggcg      300
ttcagcgcca cgatgctcgc gtggggcgcg atcgagagcc ccacgggcta ctcgaaggcc      360
ggctcgctcg acgagctcaa ggacaacctg cggttcgtca gcgactactt cgtcaaggcg      420
cacactgccc cgaacgagct gtacgtgcag gtcggcgacg gcgaggcgga ccacaagtgg      480
tggggacccg ccgaggtcat gaccatggcg cggccgtcgc acaagatcag cgcgtcctgc      540
cccggctcgg acgtggccgc ggagacggcc gccgcgctgg cgtcgtcggc gatcgtcctc      600
aagggcgacg acccggccta cgcggcgacc ctcgtgtcgc acgccaagca gctctacacg      660
ttcgcggaca cctaccgcgg cgcgtactcc gactgcgtca cggccgcctc ggcgtactac      720
aagtcctggt ccggctacca ggacgagctc gtctggggcg cgtactggct ctacaaggcc      780
accggtgacg cgacgtacct cgccaaggcc gaggccgagt acgacaagct cggcacggag      840
aaccagagca ccacgcgctc ctacaagtgg acgatcgcgt gggacaacaa gcagttcggc      900
acgtacgcgc tgctcgcgat ggagaccggc aagcagaagt acgtcgacga cgcgaaccgc      960
tggctcgact actggaccgt cggcgtcaac ggccagaagg tgccgtactc gccgggaggc     1020
caggccgtcc tcgactcgtg gggtgcgctg cggtacgccg ccaacacctc gttcgtcgcg     1080
ctcgtctact ccgactggat gaccgacgcg acccgcaagg cccggtacca cgacttcggc     1140
gtgcggcaga tcaactacgc gctcggcgac aacccgcggt cgtcgtcgta cgtcgtcggc     1200
ttcggcgcga acccgccgac cgcgccccac caccgcaccg cgcacgggtc gtggctcgac     1260
tcgatcacga cgcccgcgca gtcgcggcac gtcctgtacg gcgccctcgt cggcggtccc     1320
ggctcgccca acgacgccta caccgacagc cggcaggact acgtcgccaa cgaggtcgcg     1380
accgactaca acgcgggctt caccagccgc ctcgctcggc tcgtcgagga gtacggcggc     1440
acgccgctcg cgtcgttccc gacgcccgag cagcccgacg cgaccagct gttcgtcgag     1500 gcgatgctca accagccgcc cagcggcacg ttcaccgagg tcaaggccat gatccgcaac     1560
cagtcggcgt tcccggcgcg gtcgctgaag aacgccaagg tccggtactg gttcacgacc     1620
gacggcttcg cggcctccga cgtcacgctc tccgccaact acagcgagtg cggcgcgcag     1680
tccggcaagg gcgtcagcgc gggcggcacg ctcggctacg tcgagctctc gtgcgtcggc     1740
caggacatcc accccggcgg ccagtcgcag caccgccgcg agatccagtt ccggctcacc     1800
ggccccgccg ggtggaaccc cgcgaacgac ccgtcgtaca cgggcctgac gcagaccgcg     1860
ctcgccaagg cgtccgcgat cacgctctac gacggcagca cgctcgtctg gggcaaggag     1920
ccgaccggga cgacgacgga caccaccccg ccgacgacgc cgggcacgcc cgtcgccacc     1980
ggcgtcacga ccgtcggcgc gtcgctgtcg tgggccgcgt ccaccgacgc cgggtcgggc     2040
gtcgccgggt acgagctgta ccgggtgcag ggcacgacg agacgctcgt cgggacgacg     2100
accgccgcgg cgtacatcct gcgcgacctc accccgggca cggcgtactc ctacgtcgtc     2160
aaggccaagg acgtcgccgg caacgtgtcc gccgcgtccg ccgccgtcac cttcacgacc     2220
gacacgaccg gggagaccga ccgccgacg acccgggca cgcccgtggc gtccgcggtc     2280
acgtcgacgg gtgcgacgct cgcgtgggcg ccgtcgaccg cgacccggc ggtgagcggc     2340 tacgacgtgc tgcgcgtcca gggcacgacg acgacggtgg tcgcgcagac gaccgtcccg     2400
accgtgacgc tgtccggcct gaccccgagc acggcgtaca cctacgcggt gcgggcgaag     2460
aacgtcgcag gtgacgtctc ggccctctcg gcgccggtca cgttcacgac ggccgcaccg     2520
ccggtcgaca ccgtcgcacc gaccgtcccc ggcacgccgg tcgcgtcgaa cgtcgccacg     2580
```

-continued

```
acgggcgcca cgctcacgtg gaccgcgtcg accgacagcg gcggcagcgg gctggccggc    2640
tacgaggtgc tccgggtcag cgggacgacg cagaccctcg tcgcctcgcc cacgacggcg    2700
accgtcgccc tcgccggcct cacgccggcc accgcgtaca gctacgtggt gcgggccaag    2760
gacgcgcgg ggaacgtctc cgcggtgagc agcccggtga cgttcacgac cctgccggtg    2820
acgagcaccc cgtcgtgcac ggtcgtgtac tcgacgaaca gctggaacgt cggcttcacg    2880
gggtcggtga agatcaccaa cacgggcacc acgccgctga cctggaccct cgggttcgcc    2940
ttcccctctg gccagcaggt cacgcagggc tggagcgcca cgtggtcgca gaccgggacg    3000
acggtcaccg cgaccggcct gtcgtggaac gccaccctgc agccgggcca gagcaccgac    3060
atcgggttca acgggtccca ccccgggacc aacacgaacc cggcgtcgtt caccgtgaac    3120
ggtgaggtct gcggctga                                                 3138
```

<210> SEQ ID NO 5
<211> LENGTH: 1101
<212> TYPE: PRT
<213> ORGANISM: Cellulomonas fimi

<400> SEQUENCE: 5

```
Val Val Ser Arg Arg Ser Ser Gln Ala Arg Gly Ala Leu Thr Ala Val
  1               5                  10                  15

Val Ala Thr Leu Ala Leu Ala Leu Ala Gly Ser Gly Thr Ala Leu Ala
             20                  25                  30

Ala Ser Pro Ile Gly Glu Gly Thr Phe Asp Asp Gly Pro Glu Gly Trp
         35                  40                  45

Val Ala Tyr Gly Thr Asp Gly Pro Leu Asp Thr Ser Thr Gly Ala Leu
     50                  55                  60

Cys Val Ala Val Pro Ala Gly Ser Ala Gln Tyr Gly Val Gly Val Val
 65                  70                  75                  80

Leu Asn Gly Val Ala Ile Glu Glu Gly Thr Thr Tyr Thr Leu Arg Tyr
                 85                  90                  95

Thr Ala Thr Ala Ser Thr Asp Val Thr Val Arg Ala Leu Val Gly Gln
            100                 105                 110

Asn Gly Ala Pro Tyr Gly Thr Val Leu Asp Thr Ser Pro Ala Leu Thr
        115                 120                 125

Ser Glu Pro Arg Gln Val Thr Glu Thr Phe Thr Ala Ser Ala Thr Tyr
    130                 135                 140

Pro Ala Thr Pro Ala Ala Asp Asp Pro Glu Gly Gln Ile Ala Phe Gln
145                 150                 155                 160

Leu Gly Gly Phe Ser Ala Asp Ala Trp Thr Phe Cys Leu Asp Asp Val
                165                 170                 175

Ala Leu Asp Ser Glu Val Glu Leu Leu Pro His Thr Ser Phe Ala Glu
            180                 185                 190

Ser Leu Gly Pro Trp Ser Leu Tyr Gly Thr Ser Glu Pro Val Phe Ala
        195                 200                 205

Asp Gly Arg Met Cys Val Asp Leu Pro Gly Gly Gly Asn Pro Trp
    210                 215                 220

Asp Ala Gly Leu Val Tyr Asn Gly Val Pro Val Gly Glu Gly Glu Ser
225                 230                 235                 240

Tyr Val Leu Ser Phe Thr Ala Ser Ala Thr Pro Asp Met Pro Val Arg
                245                 250                 255

Val Leu Val Gly Glu Gly Gly Gly Ala Tyr Arg Thr Ala Phe Glu Gln
            260                 265                 270
```

```
Gly Ser Ala Pro Leu Thr Gly Glu Pro Ala Thr Arg Glu Tyr Ala Phe
            275                 280                 285

Thr Ser Asn Leu Thr Phe Pro Asp Gly Asp Ala Pro Gly Gln Val
    290                 295                 300

Ala Phe His Leu Gly Lys Ala Gly Ala Tyr Glu Phe Cys Ile Ser Gln
305                 310                 315                 320

Val Ser Leu Thr Thr Ser Ala Thr Pro Pro Gly Tyr Glu Pro Asp
                325                 330                 335

Thr Gly Pro Arg Val Arg Val Asn Gln Val Gly Tyr Leu Pro Phe Gly
            340                 345                 350

Pro Lys Arg Ala Thr Leu Val Thr Asp Ala Ala Glu Pro Val Ala Trp
        355                 360                 365

Glu Leu Arg Asp Ala Asp Gly Val Val Ala Asp Gly Thr Ser Glu
    370                 375                 380

Pro Arg Gly Val Glu Pro Ser Ala Ala Gln Ala Val His Val Leu Asp
385                 390                 395                 400

Phe Ser Asp Val Thr Thr Gln Gly Ala Gly Tyr Thr Leu Val Ala Asp
                405                 410                 415

Gly Glu Thr Ser Arg Pro Phe Asp Ile Asp Gly Asp Leu Tyr Gln Gln
            420                 425                 430

Leu Arg Tyr Asp Ala Leu Asn Tyr Phe Tyr Leu Ala Arg Ser Gly Thr
        435                 440                 445

Glu Ile Glu Ala Asp Val Val Gly Glu Gly Tyr Ala Arg Glu Ala Gly
    450                 455                 460

His Val Gly Val Ala Pro Asn Gln Gly Asp Thr Asp Val Pro Cys Ile
465                 470                 475                 480

Gly Pro Arg Asp Tyr Tyr Asp Gly Trp Thr Cys Asp Tyr Arg Leu Asp
                485                 490                 495

Val Ser Gly Gly Trp Tyr Asp Ala Gly Asp His Gly Lys Tyr Val Val
            500                 505                 510

Asn Gly Gly Ile Ala Val Gly Gln Leu Leu Gln Thr Tyr Glu Arg Ala
        515                 520                 525

Leu His Ala Gly Thr Ala Asp Ala Leu Ala Asp Gly Thr Leu Asp Val
    530                 535                 540

Pro Glu His Gly Asn Asp Val Pro Asp Val Leu Asp Glu Ala Arg Trp
545                 550                 555                 560

Glu Leu Glu Trp Met Leu Ser Met Ile Val Pro Glu Gly Glu Tyr Ala
                565                 570                 575

Gly Met Val His His Lys Val His Asp Glu Gly Trp Thr Gly Leu Pro
            580                 585                 590

Leu Leu Pro Ala Asp Asp Pro Gln Ala Arg Ser Leu His Arg Pro Ser
        595                 600                 605

Thr Ala Ala Thr Leu Asn Leu Ser Ala Val Ala Ala Gln Gly Ala Arg
    610                 615                 620

Leu Leu Glu Pro Tyr Asp Pro Gln Leu Ala Gln Thr Leu Leu Glu Ala
625                 630                 635                 640

Ala Arg Thr Thr Trp Ala Ala Ala Gln Glu His Pro Ala Leu Tyr Ala
                645                 650                 655

Pro Gly Glu Ala Gly Ala Asp Gly Gly Ala Tyr Asn Asp Ser Gln
            660                 665                 670

Val Ala Asp Glu Phe Tyr Trp Ala Ala Ala Glu Leu Tyr Leu Thr Thr
        675                 680                 685

Gly Glu Asp Ala Phe Ala Thr Ala Val Thr Thr Ser Pro Leu His Thr
```

```
                690             695             700
Ala Asp Val Phe Thr Ala Asp Gly Phe Gly Trp Gly Ser Val Ala Ala
705             710             715             720

Leu Gly Arg Leu Asp Leu Ala Thr Val Pro Asn Glu Leu Pro Gly Leu
            725             730             735

Asp Ala Val Gln Ser Ser Val Val Glu Gly Ala Gln Glu Tyr Leu Ala
            740             745             750

Ala Gln Ala Gly Gln Gly Phe Gly Ser Leu Tyr Ser Pro Pro Gly Gly
            755             760             765

Glu Tyr Val Trp Gly Ser Ser Ser Gln Val Ala Asn Asn Leu Val Val
770             775             780

Val Ala Thr Ala Tyr Asp Leu Thr Gly Asp Glu Arg Phe Arg Ala Ala
785             790             795             800

Thr Leu Glu Gly Leu Asp Tyr Leu Phe Gly Arg Asn Ala Leu Asn Gln
            805             810             815

Ser Tyr Val Thr Gly Trp Gly Glu Val Ala Ser His Gln Gln His Ser
            820             825             830

Arg Trp Phe Ala His Gln Leu Asp Pro Ser Leu Pro Ser Pro Pro Pro
            835             840             845

Gly Ser Leu Ala Gly Gly Pro Asn Ser Gln Ala Ala Thr Trp Asp Pro
850             855             860

Thr Thr Lys Ala Ala Phe Pro Asp Gly Cys Ala Pro Ser Ala Cys Tyr
865             870             875             880

Val Asp Glu Ile Gln Ala Trp Ser Thr Asn Glu Leu Thr Val Asn Trp
            885             890             895

Asn Ser Ala Leu Ser Trp Val Ala Ser Trp Val Ala Asp Gln Gly Ser
            900             905             910

Ala Glu Pro Val Pro Thr Ala Pro Val Val Thr Arg Gln Pro Val Asp
            915             920             925

Ala Thr Val Ala Leu Gly Ala Asp Ala Thr Phe Thr Ala Glu Ala Ser
            930             935             940

Gly Val Pro Ala Pro Thr Val Arg Trp Gln Val Arg Ala Gly Arg Gly
945             950             955             960

Trp Lys Asp Val Ala Gly Ala Thr Gly Thr Thr Leu Thr Val Arg Ala
            965             970             975

Thr Ala Arg Thr Asp Gly Thr Arg Tyr Arg Ala Val Phe Thr Asn Ala
            980             985             990

Ala Gly Ser Val Glu Ser Ala Val  Val Arg Leu Thr Val  Glu Arg Ala
            995             1000            1005

Ala Pro  Val Val Thr Gln His  Pro Ala Asp Val Arg  Ala Arg Val
    1010            1015            1020

Gly Thr  Arg Ala Val Phe Arg  Ala Ala Ala Asp Gly  Tyr Pro Thr
    1025            1030            1035

Pro Cys  Val Val Trp Gln Val  Arg Trp Gly Gly Gly  Ser Trp Arg
    1040            1045            1050

Pro Ile  Pro Trp Ala Thr Ser  Thr Thr Leu Ser Val  Pro Val Thr
    1055            1060            1065

Val Leu  Ala Ala Gly Thr Glu  Tyr Arg Ala Val Phe  Thr Asn Ala
    1070            1075            1080

Val Gly  Thr Ala Ala Thr Glu  Pro Ala Glu Leu Ala  Val Gln Arg
    1085            1090            1095

Pro Arg  Ser
    1100
```

<210> SEQ ID NO 6
<211> LENGTH: 3306
<212> TYPE: DNA
<213> ORGANISM: Cellulomonas fimi

<400> SEQUENCE: 6

| | | | | | | |
|---|---|---|---|---|---|---|
| gtggtttctc | gcaggtcatc | acaggcgcgc | ggcgcgctca | cggccgtcgt | cgcgacgctc | 60 |
| gccctcgcgc | tcgccgggag | cggcaccgcg | ctcgccgcgt | cgccgatcgg | ggagggaacg | 120 |
| ttcgacgacg | ggcccgaggg | gtgggtcgcg | tacggcaccg | acggccccct | cgacacgagc | 180 |
| acgggcgcgc | tgtgccgtcgc | cgtgccggcc | ggatccgcgc | agtacggcgt | cggcgtcgtg | 240 |
| ctcaacggcg | tcgcgatcga | ggaagggacc | acctacacgc | tccggtacac | cgcgacggcc | 300 |
| tcgaccgacg | tcaccgtgcg | ggcgctcgtc | gggcagaacg | cgcccccta | cggcaccgtg | 360 |
| ctcgacacga | gcccggccct | gacgtccgag | ccgcggcagg | tgaccgagac | gttcacggcc | 420 |
| tcggcgacgt | accccgcgac | acccgccgcc | gacgaccccg | aggggcagat | cgccttccag | 480 |
| ctcggcgggt | tcagcgccga | cgcgtggacg | ttctgcctcg | acgacgtcgc | gctcgactcc | 540 |
| gaggtcgagc | tcctgccgca | cacgtcgttc | gccgagtcgc | tcggcccgtg | gtccctgtac | 600 |
| ggcacgagcg | agccggtgtt | cgccgacggc | cggatgtgcg | tcgacctgcc | cggcgggcag | 660 |
| ggcaacccct | gggacgcggg | cctcgtctac | aacggcgttc | ccgtcggcga | gggcgagagc | 720 |
| tacgtcctgt | cgttcaccgc | gagcgcgacg | cccgacatgc | cggtgcgcgt | gctcgtcggc | 780 |
| gagggcggcg | cgcctaccg | gaccgccttc | gagcaggggt | cggcaccgct | gaccggcgag | 840 |
| cccgcgaccc | gcgagtacgc | gttcacctcg | aacctgacgt | tcccgcccga | cggcgacgca | 900 |
| cccggccagg | tcgcgttcca | cctcggcaag | gccggtgcgt | acgagttctg | catctcgcag | 960 |
| gtgtcgctca | ccacctcggc | gacgccgccg | cccgggtacg | agcccgacac | cggcccgcgc | 1020 |
| gtgcgggtca | accaggtggg | ctacctgccg | ttcgggccga | agcgcgccac | cctcgtcacc | 1080 |
| gacgcggccg | agccggtcgc | gtgggagctg | cgcgacgccg | acggcgtggt | cgtcgccgac | 1140 |
| gggaccagcg | agccgcgcgg | cgtcgagccg | tcggccgcgc | aggcggtgca | cgtgctcgac | 1200 |
| ttctccgacg | tcacgacgca | gggcgcgggg | tacacgctcg | tcgccgacgg | cgagacgagc | 1260 |
| cgccccttcg | acatcgacgg | cgacctgtac | cagcagctcc | ggtacgacgc | gctcaactac | 1320 |
| ttctacctcg | cgcgctccgg | caccgagatc | gaggcggacg | tggtcggcga | ggagtacgcc | 1380 |
| cgcgaggcgg | gccacgtcgg | cgtcgcgccc | aaccagggcg | acaccgacgt | gccgtgcatc | 1440 |
| ggcccgcgcg | actactacga | cggctggacg | tgcgactacc | ggctcgacgt | gagcggcggc | 1500 |
| tggtacgacg | ccggcgacca | cggcaagtac | gtcgtcaacg | gcggcatcgc | ggtcgggcag | 1560 |
| ctcctgcaga | cgtacgagcg | ggcgctgcac | gcgggcaccg | ccgacgcgct | cgcggacggc | 1620 |
| accctcgacg | tgcccgagca | cggcaacgac | gtgcccgacg | tcctggacga | ggcgcgctgg | 1680 |
| gagctcgagt | ggatgctctc | gatgatcgtg | cccgagggg | agtacgcggg | gatggtgcac | 1740 |
| cacaaggtgc | acgacgaggg | ctggaccggg | ctgccgctgc | tgccggccga | cgacccgcag | 1800 |
| gcgcgctcgc | tgcaccggcc | gtcgaccgcg | gcgacgctca | acctgtccgc | cgtcgcggcg | 1860 |
| caggggcgcg | gcctgctcga | gccgtacgac | ccgcagctcg | cgcagacgct | gctggaggcg | 1920 |
| gcacgcacga | cctgggctgc | ggcccaggag | cacccggcgc | tgtacgcccc | gggcgaggcc | 1980 |
| ggcgcggacg | gcgtggcgc | gtacaacgac | tcccaggtgg | ccgacgagtt | ctactgggcg | 2040 |
| gccgccgagc | tctacctgac | gacgggcgag | gacgcgttcg | ccaccgcggt | gacgacctcg | 2100 |

-continued

```
ccgctgcaca ccgcggacgt gttcaccgcg gacgggttcg gctgggggag cgtcgccgcg      2160
ctgggtcgcc tcgacctcgc gacggtgccg aacgagctgc cgggtctcga cgcggtgcaa      2220
tcgtcggtcg tcgaggggc gcaggagtac ctcgcggcgc aggcggggca gggattcggc       2280
tcgctgtact ccccgcccgg cggcgagtac gtctggggct cgagctcgca ggtcgcgaac      2340
aacctcgtcg tcgtcgcgac cgcgtacgac ctcacgggcg acgagcggtt ccgggcggcg      2400
acgctcgagg ggctcgacta cctgttcggc cgcaacgcgc tcaaccagtc gtacgtgacg      2460
ggctggggcg aggtcgcctc gcaccagcag cacagccggt ggttcgcgca ccagctcgac      2520
ccgtcgctcc cgagcccgcc gcccggctcg ctcgcgggcg ccccgaactc gcaggccgcg      2580
acgtgggacc cgacgacgaa ggcggcgttc cccgacggct gcgcgccgtc cgcgtgctac      2640
gtcgacgaga tccaggcgtg gtcgacgaac gagctcaccg tcaactggaa ctccgcgctg      2700
tcctgggtcg cctcgtgggt ggccgaccag ggctcggccg agccggtgcc gacggcgccg      2760
gtggtgacgc ggcagcccgt cgacgcgacc gtcgcgctcg gtgccgacgc cacgttcacc      2820
gcggaggcga gcggcgtgcc cgcgccgacc gtccggtggc aggtgcgggc cggccgcggc      2880
tggaaggacg tcgccggcgc gaccgggacc acgctcacgg tccgcgcgac cgcccgcacc      2940
gacggcacgg ggtaccgggc ggtgttcacc aacgcggccg gctcggtcga gagcgccgtc      3000
gtgcggctca ccgtcgagcg cgcggcaccc gtcgtgacgc agcacccggc cgacgtccgg      3060
gcacgggtcg gcacgcgtgc cgtgttccgc gcggccgccg acgggtaccc cacgccctgc      3120
gtcgtgtggc aggtgcggtg gggcggcggg agctggcggc cgatcccgtg gccacctcg      3180 acgacgctct ccgtgccggt cacggtgctc gcggcgggca cggagtaccg cgcggtgttc      3240
accaacgccg tcggcaccgc ggcgaccgag cctgccgagc tcgccgtgca cgtccgcgc      3300 agctga                                                                3306
```

<210> SEQ ID NO 7
<211> LENGTH: 872
<212> TYPE: PRT
<213> ORGANISM: Cellulomonas fimi

<400> SEQUENCE: 7

```
Val Ser Thr Leu Gly Lys Arg Ala Gly Val Arg Arg Val Arg Ala
1               5                   10                  15

Val Ala Thr Ala Ala Thr Ala Thr Ala Leu Val Ala Val Pro Leu Thr
            20                  25                  30

Thr Leu Ala Thr Ser Ala Ser Ala Ala Pro Val His Val Asp Asn Pro
        35                  40                  45

Tyr Ala Gly Ala Val Gln Tyr Val Asn Pro Thr Trp Ala Ala Ser Val
    50                  55                  60

Asn Ala Ala Ala Gly Arg Gln Ser Ala Asp Pro Ala Leu Ala Ala Lys
65                  70                  75                  80

Met Arg Thr Val Ala Gly Gln Pro Thr Ala Val Trp Met Asp Arg Ile
                85                  90                  95

Ser Ala Ile Thr Gly Asn Ala Asp Gly Asn Gly Leu Lys Phe His Leu
            100                 105                 110

Asp Asn Ala Val Ala Gln Gln Lys Ala Ala Gly Val Pro Leu Val Phe
        115                 120                 125

Asn Leu Val Ile Tyr Asp Leu Pro Gly Arg Asp Cys Phe Ala Leu Ala
    130                 135                 140

Ser Asn Gly Glu Leu Pro Ala Thr Asp Ala Gly Leu Ala Arg Tyr Lys
145                 150                 155                 160
```

-continued

```
Ser Glu Tyr Ile Asp Pro Ile Ala Asp Leu Leu Asp Asn Pro Glu Tyr
            165                 170                 175

Glu Ser Ile Arg Ile Ala Ala Thr Ile Glu Pro Asp Ser Leu Pro Asn
            180                 185                 190

Leu Thr Thr Asn Ile Ser Glu Pro Ala Cys Gln Gln Ala Ala Pro Tyr
            195                 200                 205

Tyr Arg Gln Gly Val Lys Tyr Ala Leu Asp Lys Leu His Ala Ile Pro
210                 215                 220

Asn Val Tyr Asn Tyr Ile Asp Ile Gly His Ser Gly Trp Leu Gly Trp
225                 230                 235                 240

Asp Ser Asn Ala Gly Pro Ser Ala Thr Leu Phe Ala Glu Val Ala Lys
            245                 250                 255

Ser Thr Thr Ala Gly Phe Ala Ser Ile Asp Gly Phe Val Ser Asp Val
            260                 265                 270

Ala Asn Thr Thr Pro Leu Glu Glu Pro Leu Leu Ser Asp Ser Ser Leu
            275                 280                 285

Thr Ile Asn Asn Thr Pro Ile Arg Ser Ser Lys Phe Tyr Glu Trp Asn
290                 295                 300

Phe Asp Phe Asp Glu Ile Asp Tyr Thr Ala His Met His Arg Leu Leu
305                 310                 315                 320

Val Ala Ala Gly Phe Pro Ser Ser Ile Gly Met Leu Val Asp Thr Ser
            325                 330                 335

Arg Asn Gly Trp Gly Gly Pro Asn Arg Pro Thr Ser Ile Thr Ala Ser
            340                 345                 350

Thr Asp Val Asn Ala Tyr Val Asp Ala Asn Arg Val Asp Arg Arg Val
            355                 360                 365

His Arg Gly Ala Trp Cys Asn Pro Leu Gly Ala Gly Ile Gly Arg Phe
370                 375                 380

Pro Glu Ala Thr Pro Ser Gly Tyr Ala Ala Ser His Leu Asp Ala Phe
385                 390                 395                 400

Val Trp Ile Lys Pro Pro Gly Glu Ser Asp Gly Ala Ser Thr Asp Ile
            405                 410                 415

Pro Asn Asp Gln Gly Lys Arg Phe Asp Arg Met Cys Asp Pro Thr Phe
            420                 425                 430

Val Ser Pro Lys Leu Asn Asn Gln Leu Thr Gly Ala Thr Pro Asn Ala
            435                 440                 445

Pro Leu Ala Gly Gln Trp Phe Glu Glu Gln Phe Val Thr Leu Val Lys
450                 455                 460

Asn Ala Tyr Pro Val Ile Gly Gly Thr Thr Pro Val Glu Asp Leu Val
465                 470                 475                 480

Ala Pro Thr Val Pro Thr Gly Leu Thr Ala Gly Thr Thr Ala Thr
            485                 490                 495

Ser Val Pro Leu Ser Trp Thr Ala Ser Thr Asp Asn Val Ala Val Thr
            500                 505                 510

Gly Tyr Asp Val Tyr Arg Gly Thr Thr Leu Val Gly Thr Thr Ala Ala
            515                 520                 525

Thr Ser Tyr Thr Val Thr Gly Leu Thr Pro Ala Thr Ala Tyr Ser Phe
            530                 535                 540

Thr Val Arg Ala Lys Asp Ala Ala Gly Asn Val Ser Ala Ala Ser Ala
545                 550                 555                 560

Ala Ala Ala Ala Thr Thr Gln Ser Gly Thr Val Thr Asp Thr Thr Ala
            565                 570                 575
```

-continued

```
Pro Ser Val Pro Ala Gly Leu Thr Ala Gly Thr Thr Thr Thr Thr
            580                 585                 590
Val Pro Leu Ser Trp Thr Ala Ser Thr Asp Asn Ala Gly Ser Gly
        595                 600                 605
Val Ala Gly Tyr Glu Val Leu Arg Gly Thr Thr Val Gly Thr Thr
    610                 615                 620
Thr Ala Thr Ser Tyr Thr Val Thr Gly Leu Thr Ala Gly Thr Thr Tyr
625                 630                 635                 640
Ser Phe Ser Val Arg Ala Lys Asp Val Ala Gly Asn Thr Ser Ala Ala
                645                 650                 655
Ser Ala Ala Val Ser Ala Thr Thr Gln Thr Gly Thr Val Asp Thr
            660                 665                 670
Thr Ala Pro Ser Val Pro Thr Gly Leu Thr Ala Gly Thr Thr Thr Thr
    675                 680                 685
Ser Ser Val Pro Leu Thr Trp Thr Ala Ser Thr Asp Asn Ala Gly Gly
690                 695                 700
Ser Gly Val Ala Gly Tyr Glu Val Phe Asn Gly Thr Thr Arg Val Ala
705                 710                 715                 720
Thr Val Thr Ser Thr Ser Tyr Thr Val Thr Gly Leu Ala Ala Asp Thr
                725                 730                 735
Ala Tyr Ser Phe Thr Val Lys Ala Lys Asp Val Ala Gly Asn Val Ser
            740                 745                 750
Ala Ala Ser Ala Ala Val Ser Ala Arg Thr Gln Ala Ala Thr Ser Gly
        755                 760                 765
Gly Cys Thr Val Lys Tyr Ser Ala Ser Ser Trp Asn Thr Gly Phe Thr
    770                 775                 780
Gly Thr Val Glu Val Lys Asn Asn Gly Thr Ala Ala Leu Asn Gly Trp
785                 790                 795                 800
Thr Leu Gly Phe Ser Phe Ala Asp Gly Gln Lys Val Ser Gln Gly Trp
                805                 810                 815
Ser Ala Glu Trp Ser Gln Ser Gly Thr Ala Val Thr Ala Lys Asn Ala
            820                 825                 830
Pro Trp Asn Gly Thr Leu Ala Ala Gly Ser Ser Val Ser Ile Gly Phe
        835                 840                 845
Asn Gly Thr His Asn Gly Thr Asn Thr Ala Pro Thr Ala Phe Thr Leu
    850                 855                 860
Asn Gly Val Ala Cys Thr Leu Gly
865                 870

<210> SEQ ID NO 8
<211> LENGTH: 2619
<212> TYPE: DNA
<213> ORGANISM: Cellulomonas fimi
<400> SEQUENCE: 8
gtgtccacac tcggcaagcg agcaggggtg aggcgtcgcg tacgcgccgt cgccaccgct      60
gcgacggcga cggctctcgt cgccgtcccc ctcaccaccc tggcgacgag cgcgagcgcc     120
gcgcccgtcc acgtcgacaa ccccctacgcc ggcgcggtgc agtacgtgaa ccccacgtgg     180
gccgcctcgg tgaacgccgc tgccggccgg cagagcgcgg accgccccct cgccgcgaag     240
atgcggacgg tcgcgggtca gcccaccgcc gtgtggatgg accggatcag cgcgatcacg     300
ggcaacgccg acgcaacgg cctgaagttc cacctcgaca cgccgtcgc gcagcagaag     360
gccgcgggcg tgccgctcgt gttcaacctc gtcatctacg acctgccggg ccgcgactgc     420
```

```
ttcgcgctcg cgtccaacgg cgagctgccc gcgaccgacg ccggcctcgc gcggtacaag      480
agcgagtaca tcgacccgat cgcggacctg ctcgacaacc cggagtacga gagcatccgg      540
atcgccgcga cgatcgagcc cgactcgctg ccgaacctca cgacgaacat ctcggagccc      600
gcctgccagc aggcggcgcc gtactaccgg cagggcgtca agtacgcgct cgacaagctg      660
cacgcgatcc gaacgtctca caactacatc gacatcggcc actccggctg gctcggctgg      720
gacagcaacg cgggcccgtc cgcgacgctg ttcgccgagg tcgccaagtc gacgacggcc      780
gggttcgcgt cgatcgacgg gttcgtgtcc gacgtcgcga acacgacgcc gctcgaggag      840
ccgctgctct ccgactcgtc cctgacgatc aacaacaccc cgatccggtc gtcgaagttc      900
tacgagtgga acttcgactt cgacgagatc gactacaccg cgcacatgca ccggctgctg      960
gtcgcggcgg gcttcccgtc gtcgatcggc atgctcgtcg cacgtcgcg caacggctgg     1020 ggcggcccca accgtccgac gtcgatcacc gcgagcaccg acgtgaacgc ctacgtcgac     1080
gcgaaccgcg tggaccgtcg cgtgcaccgc ggcgcgtggt gcaacccgct gggtgcgggc     1140
atcggccggt tcccggaggc cacgccgtcc ggctacgccg cgtcgcacct cgacgcgttc     1200
gtctggatca agcccccggg tgagtccgac ggcgcctcga ccgacatccc gaacgaccag     1260
ggcaagcggt cgaccgcat gtgcgacccg acgttcgtct cgcccaagct caacaaccag     1320
ctgacgggtg cgacgcccaa cgcgccgctc gccggccagt ggttcgagga gcagttcgtc     1380
accctcgtga agaacgcgta cccggtgatc ggcggcacga cgcccgtcga ggacctggtg     1440
gcgccgacgg tgccgaccgg cctgaccgcc ggcacgacca ccgcgacgtc ggtcccgctg     1500
tcgtggacgc cgtcgacgga caacgtcgcc gtcaccggct acgacgtcta ccgcggcacg     1560
accctcgtgg gcacgaccgc cgcgacgagc tacaccgtca cgggcctgac cccggccacg     1620
gcgtactcgt tcacggtccg ggcgaaggac gccgcgggca acgtctcggc ggcctccgcc     1680
gcggcggccg cgacgacgca gtccggcacc gtgacggaca cgacggcgcc gtccgtcccg     1740
gccggtctga cggccggcac gacgacgacc acgacggtcc cgctctcgtg gaccgcctcg     1800
accgacaacg ccggagggtc cggcgtcgcg ggctacgagg tcctgcgcgg cacgacggtc     1860
gtcggcacca cgacggcgac gagctacacg gtcacgggcc tgacggccgg caccacgtac     1920
tcgttctccg tgcgggccaa ggacgtcgcg ggcaacacgt ccgccgcctc cgccgcggtc     1980
tccgcgacga cgcagaccgg cacgtggtc gacaccacgg ccccgtccgt cccgaccggc     2040
ctgaccgccg gcacgacgac gacctcgtcg gtcccgctga cgtggaccgc ctcgacggac     2100
aacgcgggcg gctcgggcgt cgccggctac gaggtcttca acggcaccac gcgcgtggcg     2160
accgtgacct cgacgagcta cacggtcacc ggcctcgcgg cggacaccgc gtactcgttc     2220
acggtcaagg ccaaggacgt cgcgggcaac gtgtcggcag cctcggcagc cgtctccgcc     2280
cggacgcagg cggccacgtc cggcggctgc acggtgaagt actccgccag ctcgtggaac     2340
accggcttca ccggcacggt cgaggtgaag aacaacggca cggcggccct caacggctgg     2400
acgctcggct tctccttcgc cgacggccag aaggtgtcgc agggctggag cgccgagtgg     2460
tcgcagtccg gcaccgcggt gacggccaag aacgcgccgt ggaacggcac gctcgccgcc     2520
ggctccagcg tgtcgatcgg cttcaacggc acgcacaacg gcacgaacac cgcgccgacg     2580
gcgttcacgc tcaacggcgt cgcctgcacg ctcggctga                              2619

<210> SEQ ID NO 9
<211> LENGTH: 484
<212> TYPE: PRT
<213> ORGANISM: Cellulomonas fimi
```

```
<400> SEQUENCE: 9

Met Pro Arg Thr Thr Pro Ala Pro Gly His Pro Ala Arg Gly Ala Arg
1               5                   10                  15

Thr Ala Leu Arg Thr Thr Arg Arg Ala Ala Thr Leu Val Val Gly
            20                  25                  30

Ala Thr Val Val Leu Pro Ala Gln Ala Ala Thr Thr Leu Lys Glu Ala
                35                  40                  45

Ala Asp Gly Ala Gly Arg Asp Phe Gly Phe Ala Leu Asp Pro Asn Arg
    50                  55                  60

Leu Ser Glu Ala Gln Tyr Lys Ala Ile Ala Asp Ser Glu Phe Asn Leu
65                  70                  75                  80

Val Val Ala Glu Asn Ala Met Lys Trp Asp Ala Thr Glu Pro Ser Gln
                85                  90                  95

Asn Ser Phe Ser Phe Gly Ala Gly Asp Arg Val Ala Ser Tyr Ala Ala
                100                 105                 110

Asp Thr Gly Lys Glu Leu Tyr Gly His Thr Leu Val Trp His Ser Gln
            115                 120                 125

Leu Pro Asp Trp Ala Lys Asn Leu Asn Gly Ser Ala Phe Glu Ser Ala
130                 135                 140

Met Val Asn His Val Thr Lys Val Ala Asp His Phe Glu Gly Lys Val
145                 150                 155                 160

Ala Ser Trp Asp Val Val Asn Glu Ala Phe Ala Asp Gly Asp Gly Pro
                165                 170                 175

Pro Gln Asp Ser Ala Phe Gln Gln Lys Leu Gly Asn Gly Tyr Ile Glu
            180                 185                 190

Thr Ala Phe Arg Ala Ala Arg Ala Ala Asp Pro Thr Ala Lys Leu Cys
        195                 200                 205

Ile Asn Asp Tyr Asn Val Glu Gly Ile Asn Ala Lys Ser Asn Ser Leu
    210                 215                 220

Tyr Asp Leu Val Lys Asp Phe Lys Ala Arg Gly Val Pro Leu Asp Cys
225                 230                 235                 240

Val Gly Phe Gln Ser His Leu Ile Val Gly Gln Val Pro Gly Asp Phe
                245                 250                 255

Arg Gln Asn Leu Gln Arg Phe Ala Asp Leu Gly Val Asp Val Arg Ile
            260                 265                 270

Thr Glu Leu Asp Ile Arg Met Arg Thr Pro Ser Asp Ala Thr Lys Leu
        275                 280                 285

Ala Thr Gln Ala Ala Asp Tyr Lys Lys Val Val Gln Ala Cys Met Gln
    290                 295                 300

Val Thr Arg Cys Gln Gly Val Thr Val Trp Gly Ile Thr Asp Lys Tyr
305                 310                 315                 320

Ser Trp Val Pro Asp Val Phe Pro Gly Glu Gly Ala Ala Leu Val Trp
                325                 330                 335

Asp Ala Ser Tyr Ala Lys Lys Pro Ala Tyr Ala Ala Val Met Glu Ala
            340                 345                 350

Phe Gly Ala Ser Pro Thr Pro Thr Pro Thr Pro Thr Pro Thr Pro Pro
        355                 360                 365

Thr Thr Pro Thr Pro Thr Pro Thr Ser Gly Pro Ala Gly Cys Gln Val
    370                 375                 380

Leu Trp Gly Val Asn Gln Trp Asn Thr Gly Phe Thr Ala Asn Val Thr
385                 390                 395                 400

Val Lys Asn Thr Ser Ser Ala Pro Val Asp Gly Trp Thr Leu Thr Phe
```

```
                     405                 410                 415
Ser Phe Pro Ser Gly Gln Gln Val Thr Gln Ala Trp Ser Ser Thr Val
            420                 425                 430

Thr Gln Ser Gly Ser Ala Val Thr Val Arg Asn Ala Pro Trp Asn Gly
            435                 440                 445

Ser Ile Pro Ala Gly Gly Thr Ala Gln Phe Gly Phe Asn Gly Ser His
            450                 455                 460

Thr Gly Thr Asn Ala Ala Pro Thr Ala Phe Ser Leu Asn Gly Thr Pro
465                 470                 475                 480

Cys Thr Val Gly

<210> SEQ ID NO 10
<211> LENGTH: 1455
<212> TYPE: DNA
<213> ORGANISM: Cellulomonas fimi

<400> SEQUENCE: 10
atgcctagga ccacgcccgc acccggccac ccggcccgcg gcgcccgcac cgctctgcgc    60
acgacgcgcc gccgcgcggc gacgctcgtc gtcggcgcca cggtcgtgct gcccgcccag   120
gccgcgacca cgctcaagga ggccgccgac ggcgccggcc gggacttcgg cttcgcgctc   180
gaccccaacc ggctctcgga ggcgcagtac aaggcgatcg ccgacagcga gttcaacctc   240
gtcgtcgccg agaacgcgat gaagtgggac gccaccgagc cctcgcagaa cagcttctcc   300
ttcggcgcgg gcgaccgcgt cgcgagctac gccgccgaca ccggcaagga gctgtacggc   360
cacacgctcg tctggcactc gcagctgccc gactgggcga agaacctcaa cggctccgcg   420
ttcgagagcg cgatggtcaa ccacgtgacg aaggtcgccg accacttcga gggcaaggtc   480
gcgtcgtggg acgtcgtcaa cgaggcgttc gccgacggcg acggcccgcc gcaggactcg   540
gcgttccagc agaagctcgg caacggctac atcgagaccg cgttccgggc ggcacgtgcg   600
gcggacccga ccgccaagct gtgcatcaac gactacaacg tcgagggcat caacgcgaag   660
agcaactcgc tctacgacct cgtcaaggac ttcaaggcgc gcggcgtccc gctcgactgc   720
gtcgggttcc agtcgcacct catcgtcggc aggtgccgg cgacttccg gcagaacctg   780 cagcggttcg cggacctggg cgtggacgtg cgcatcaccg agctcgacat ccgcatgcgg   840
acgccctccg acgcgaccaa gctcgcgacc caggcggccg actacaagaa ggtcgtgcag   900
gcctgcatgc aggtgacccg ctgccagggc gtgaccgtct ggggcatcac cgacaagtac   960
tcgtgggtgc cggacgtctt cccgggcgag gggccgcgc tggtgtggga cgcgagctac  1020
gccaagaagc cggcctacgc cgccgtgatg gaggccttcg gcgcgagccc gacgccgacg  1080
cccaccacgc cgaccccgac gcccacgacg ccgacgccga ccccgacgtc cggtccggcc  1140
gggtgccagg tgctgtgggg cgtcaaccag tggaacaccg gcttcaccgc gaacgtcacc  1200
gtgaagaaca cgtcctccgc tccggtcgac ggctggacgc tcacgttcag cttcccgtcc  1260
ggccagcagg tcacccaggc gtggagctcg acggtcacgc agtccggctc ggccgtgacg  1320
gtccgcaacg ccccgtggaa cggctcgatc ccggcgggcg gcaccgcgca gttcggcttc  1380
aacggctcgc acacgggcac caacgccgcg ccgacggcgt tctcgctcaa cggcacgccc  1440
tgcacggtcg gctga                                                   1455

<210> SEQ ID NO 11
<211> LENGTH: 441
<212> TYPE: PRT
<213> ORGANISM: Cellulomonas fimi
```

<400> SEQUENCE: 11

```
Met Ser Pro Arg Pro Leu Arg Ala Leu Leu Gly Ala Ala Ala Ala Ala
1               5                   10                  15

Leu Val Ser Ala Ala Ala Leu Ala Phe Pro Ser Gln Ala Ala Ala Asn
            20                  25                  30

Asp Ser Pro Phe Tyr Val Asn Pro Asn Met Ser Ser Ala Glu Trp Val
        35                  40                  45

Arg Asn Asn Pro Asn Asp Pro Arg Thr Pro Val Ile Arg Asp Arg Ile
    50                  55                  60

Ala Ser Val Pro Gln Gly Thr Trp Phe Ala His His Asn Pro Gly Gln
65                  70                  75                  80

Ile Thr Gly Gln Val Asp Ala Leu Met Ser Ala Ala Gln Ala Ala Gly
                85                  90                  95

Lys Ile Pro Ile Leu Val Val Tyr Asn Ala Pro Gly Arg Asp Cys Gly
            100                 105                 110

Asn His Ser Ser Gly Gly Ala Pro Ser His Ser Ala Tyr Arg Ser Trp
        115                 120                 125

Ile Asp Glu Phe Ala Ala Gly Leu Lys Asn Arg Pro Ala Tyr Ile Ile
    130                 135                 140

Val Glu Pro Asp Leu Ile Ser Leu Met Ser Ser Cys Met Gln His Val
145                 150                 155                 160

Gln Gln Glu Val Leu Glu Thr Met Ala Tyr Ala Gly Lys Ala Leu Lys
                165                 170                 175

Ala Gly Ser Ser Gln Ala Arg Ile Tyr Phe Asp Ala Gly His Ser Ala
            180                 185                 190

Trp His Ser Pro Ala Gln Met Ala Ser Trp Leu Gln Gln Ala Asp Ile
        195                 200                 205

Ser Asn Ser Ala His Gly Ile Ala Thr Asn Thr Ser Asn Tyr Arg Trp
    210                 215                 220

Thr Ala Asp Glu Val Ala Tyr Ala Lys Ala Val Leu Ser Ala Ile Gly
225                 230                 235                 240

Asn Pro Ser Leu Arg Ala Val Ile Asp Thr Ser Arg Asn Gly Asn Gly
                245                 250                 255

Pro Ala Gly Asn Glu Trp Cys Asp Pro Ser Gly Arg Ala Ile Gly Thr
            260                 265                 270

Pro Ser Thr Thr Asn Thr Gly Asp Pro Met Ile Asp Ala Phe Leu Trp
        275                 280                 285

Ile Lys Leu Pro Gly Glu Ala Asp Gly Cys Ile Ala Gly Ala Gly Gln
    290                 295                 300

Phe Val Pro Gln Ala Ala Tyr Glu Met Ala Ile Ala Ala Gly Gly Thr
305                 310                 315                 320

Asn Pro Asn Pro Asn Pro Asn Pro Thr Pro Thr Pro Thr Pro Thr Pro
                325                 330                 335

Thr Pro Pro Pro Gly Ser Ser Gly Ala Cys Thr Ala Thr Tyr Thr Ile
            340                 345                 350

Ala Asn Glu Trp Asn Asp Gly Phe Gln Ala Thr Val Thr Val Thr Ala
        355                 360                 365

Asn Gln Asn Ile Thr Gly Trp Thr Val Thr Trp Thr Phe Thr Asp Gly
    370                 375                 380

Gln Thr Ile Thr Asn Ala Trp Asn Ala Asp Val Ser Thr Ser Gly Ser
385                 390                 395                 400

Ser Val Thr Ala Arg Asn Val Gly His Asn Gly Thr Leu Ser Gln Gly
```

```
            405                 410                 415
Ala Ser Thr Glu Phe Gly Phe Val Gly Ser Lys Gly Asn Ser Asn Ser
        420                 425                 430

Val Pro Thr Leu Thr Cys Ala Ala Ser
        435                 440

<210> SEQ ID NO 12
<211> LENGTH: 1326
<212> TYPE: DNA
<213> ORGANISM: Cellulomonas fimi

<400> SEQUENCE: 12
atgtccccca gacctcttcg cgctcttctg ggcgccgcgg cggcggcctt ggtcagcgcg      60
gctgctctgg ccttcccgtc gcaagcggcg gccaatgatt ctccgttcta cgtcaacccc     120
aacatgtcct ccgccgaatg ggtgcggaac aaccccaacg accgcgtac cccggtaatc     180 cgcgaccgga tcgccagcgt gccgcagggc acctggttcg cccaccacaa ccccgggcag    240
atcaccggcc aggtcgacgc gctcatgagc gccgcccagg ccgccggcaa gatcccgatc     300
ctggtcgtgt acaacgcccc gggccgcgac tgcggcaacc acagcagcgg cggcgccccc     360
agtcacagcg cctaccggtc ctggatcgac gaattcgctg ccggactgaa gaaccgtccc     420
gcctacatca tcgtcgaacc ggacctgatc tcgctgatgt cgagctgcat gcagcacgtc     480
cagcaggaag tcctggagac gatggcgtac gcgggcaagg ccctcaaggc cgggtcctcg     540
caggcgcgga tctacttcga cgccggccac tccgcgtggc actcgcccgc acagatggct     600
tcctggctcc agcaggccga catctccaac agcgcgcacg gtatcgccac caacacctcc     660
aactaccggt ggaccgctga cgaggtcgcc tacgccaagg cggtgctctc ggccatcggc     720
aacccgtccc tgcgcgcgt catcgacacc agccgcaacg gcaacggccc cgccggtaac     780
gagtggtgcg accccagcgg acgcgccatc ggcacgccca gcaccaccaa caccggcgac     840
ccgatgatcg acgccttcct gtggatcaag ctgccgggtg aggccgacgg ctgcatcgcc     900
ggcgccggcc agttcgtccc gcaggcggcc tacgagatgg cgatcgccgc gggcggcacc     960
aaccccaacc cgaaccccaa cccgacgccc accccactc cgaccccac gccgcctccc    1020 ggctcctcgg gggcgtgcac ggcgacgtac acgatcgcca acgagtggaa cgacggcttc    1080
caggcgaccg tgacggtcac cgcgaaccag aacatcaccg gctggaccgt gacgtggacc    1140
ttcaccgacg gccagaccat caccaacgcc tggaacgccg acgtgtccac cagcggctcc    1200
tcggtgaccg cgcggaacgt cggccacaac ggaacgctct cccagggagc tccacagag    1260 ttcggcttcg tcggctctaa gggcaactcc aactctgttc cgaccctta c ctgcgccgcc    1320 agctga                                                              1326

<210> SEQ ID NO 13
<211> LENGTH: 328
<212> TYPE: PRT
<213> ORGANISM: Thermobifida fusca

<400> SEQUENCE: 13

Met Thr Leu Leu Arg Arg Gly Ala Ala Pro Pro Gly Asp Lys Glu Ala
1               5                   10                  15

Thr Ser Leu Pro Arg Pro Gly Asn Asp Ala Val Thr Glu Arg Glu Arg
            20                  25                  30

Arg Gln Ile Phe Trp Thr Arg Met Asp Leu Arg Val Thr Pro Tyr Leu
        35                  40                  45
```

```
Phe Ile Ala Pro Phe Phe Ile Leu Phe Ala Ile Phe Gly Leu Phe Pro
 50                  55                  60
Leu Leu Tyr Thr Val Trp Val Ser Leu His Asp Trp Thr Leu Leu Gly
 65                  70                  75                  80
Gly Asn Gln Gly Phe Asn Trp Phe Ala His Tyr Thr Arg Leu Val Gln
                 85                  90                  95
Asp Ala Lys Phe Trp Asn Ser Leu Tyr Asn Thr Phe Gly Ile Phe Val
            100                 105                 110
Val Ala Val Val Pro Gln Leu Leu Leu Ala Met Tyr Leu Ala Asp Thr
        115                 120                 125
Leu Ser Arg Arg Ile Arg Ala Val Asn Phe Phe Arg Met Gly Leu Leu
130                 135                 140
Leu Pro Tyr Leu Thr Ser Ile Ala Ala Val Ala Ile Val Phe Ser Gln
145                 150                 155                 160
Leu Phe Gly Thr Gln Phe Gly Leu Ile Asn Tyr Val Leu Gly Phe Phe
                165                 170                 175
Gly Ile Asp Pro Ile Asn Trp Gln Ala Gly Arg Phe Ser Ser Trp Val
            180                 185                 190
Ala Ile Ala Val Met Ile Asp Trp Arg Trp Thr Gly Tyr Asn Ala Leu
        195                 200                 205
Ile Tyr Leu Ala Ala Met Ser Ala Ile Pro Arg Glu Ile Tyr Glu Ala
210                 215                 220
Ala Ala Ile Asp Gly Ala Ser Arg Met Arg Gln Phe Trp Gln Ile Thr
225                 230                 235                 240
Ile Pro Met Leu Arg Pro Thr Ile Ile Phe Thr Val Ile Val Ser Thr
                245                 250                 255
Ile Gly Gln Met Gln Leu Phe Thr Glu Pro Val Ile Phe Gly Asp Val
            260                 265                 270
Ala Gly Gly Thr Gln Gly Gln Phe Gln Thr Thr Met Met Leu Ile Phe
        275                 280                 285
Glu Glu Ala Phe Arg Phe Asn Asn Tyr Gly Tyr Gly Ser Ala Ile Ala
290                 295                 300
Trp Thr Leu Phe Met Ile Ile Val Val Leu Ser Ala Leu Asn Ala Leu
305                 310                 315                 320
Leu Thr Ser Lys Ile Lys Gly Ala
                325

<210> SEQ ID NO 14
<211> LENGTH: 987
<212> TYPE: DNA
<213> ORGANISM: Thermobifida fusca

<400> SEQUENCE: 14
gtgactcttc ttaggcgtgg cgccgccccg cccggggaca aggaggcgac cagccttccc      60
cgacccggga acgacgccgt gacggagagg gagcgcaggc agatcttctg gacccgaatg     120
gatctgcggg tcaccccta tctgttcatc gccccttct tcatcctgtt cgcgatcttc       180
ggcctgtttc cgctgctcta caccgtctgg gtgtcgctcc acgactggac gctgctcggc     240
ggaaaccagg ggttcaactg gttcgcgcac tacaccaggc tcgtccagga cgccaagttc     300
tggaactcgc tgtacaacac cttcggcatc ttcgtcgtcg cggttgttcc gcagctgctc     360
ctggccatgt acctggccga cacgctgagc cggaggatcc gcgcggtcaa cttcttccgc     420
atggggctcc tgctgcccta cctcacctcg atcgctgccg tggcgatcgt cttctcccag     480
ctgttcggta cccagttcgg tctcatcaac tacgtgctgg gcttcttcgg catcgacccg     540
```

```
atcaactggc aggcaggccg gttctcctcg tgggtcgcga tcgcggtgat gatcgactgg    600
cgctggaccg gctacaacgc gctgatctac ctggcggcga tgtcggccat ccccgggag    660 atctacgagg ccgctgccat tgacggggcg tcgcgcatgc ggcagttctg gcagatcacc    720
atccccatgc tgcggcccac catcatcttc accgtcatcg tctccacgat cggccagatg    780
cagctcttca ctgagccggt catcttcggc gacgtggcgg cggtactca aggacagttc    840 cagaccacga tgatgctgat cttcgaggag gcgttccgct tcaacaacta cgggtacggc    900
tccgcgatcg cctggacgct attcatgatc atcgtggtgc tcagcgcgct gaacgcgctg    960
ctcaccagca agatcaaggg ggcatga                                        987
```

<210> SEQ ID NO 15
<211> LENGTH: 304
<212> TYPE: PRT
<213> ORGANISM: Thermobifida fusca

<400> SEQUENCE: 15

```
Met Ala Ala Thr Ser Thr Pro Ser Ser Pro Ser Val Ser Ala Val Pro
1               5                   10                  15

Gln Ser Ala Lys Lys Arg Lys Arg Lys Asn Gly Gly Ser Ile Gly Met
            20                  25                  30

Arg Glu Ala Thr Pro Leu Thr Tyr Ile Gly Leu Ser Leu Thr Ile Leu
        35                  40                  45

Leu Ser Val Phe Pro Leu Trp Trp Met Phe Val Val Ala Ser Arg Asp
    50                  55                  60

Thr Ala Ala Ala Ser Ala Arg Pro Pro Tyr Leu Trp Pro Gly Gly Asn
65                  70                  75                  80

Phe Leu Glu Asn Leu Glu Arg Leu Phe Ala Asn Thr Thr Ala Asn Phe
                85                  90                  95

Thr Leu Gly Leu Leu Asn Ser Thr Ile Ser Ala Thr Ala Val Ala Leu
            100                 105                 110

Ser Val Val Phe Phe Ser Ser Leu Ala Gly Phe Ser Leu Ala Lys Leu
        115                 120                 125

Arg Phe Lys Gly Arg Asn Val Ala Ala Val Gly Val Val Leu Thr Met
    130                 135                 140

Ala Val Pro Val Gln Met Gly Ile Ile Pro Leu Leu Met Leu Met Glu
145                 150                 155                 160

Trp Phe Gly Trp Arg Gly Gln Ile Thr Ala Ile Ile Val Pro Phe Met
                165                 170                 175

Val Ser Gly Phe Gly Val Phe Met Met Arg Gln Tyr Cys Ile Gln Ala
            180                 185                 190

Ile Pro Asp Glu Leu Leu Glu Ala Ala Arg Met Asp Gly Cys Ser Thr
        195                 200                 205

Phe Arg Ile Tyr Trp Asn Val Val Leu Pro Ala Leu Arg Pro Ala Met
    210                 215                 220

Val Val Leu Gly Leu Leu Thr Phe Met Thr Gln Trp Asn Glu Phe Thr
225                 230                 235                 240

Trp Ala Leu Ala Val Leu Thr Pro Ala Asn Pro Thr Val Gln Ile Ala
                245                 250                 255

Ile Asn Gln Leu Asn Gln Ser Ala Tyr Ser Arg Asp Phe Ala Leu Met
            260                 265                 270

Phe Thr Gly Ser Val Val Ala Thr Leu Pro Leu Leu Ile Leu Phe Phe
        275                 280                 285
```

Val Leu Gly Arg Gln Leu Ile Gly Arg Ile Met Glu Gly Ala Ile Lys
    290                 295                 300

<210> SEQ ID NO 16
<211> LENGTH: 915
<212> TYPE: DNA
<213> ORGANISM: Thermobifida fusca

<400> SEQUENCE: 16

| | | | | | |
|---|---|---|---|---|---|
| atggctgcga | cttcgacccc | gtcttctccg | tctgtgtcgg | cagtccccca | gtccgcgaag | 60 |
| aagcggaagc | ggaaaaacgg | cggcagcatc | ggtatgcggg | aggcgacccc | gctcacctac | 120 |
| atcgggctgt | ccctcaccat | cctgctgtcg | gtcttccccc | tatggtggat | gttcgtcgtg | 180 |
| gccagccgcg | acactgctgc | cgcctcagcc | cgtccaccct | acctgtggcc | cggcgggaat | 240 |
| ttcctggaaa | atctggaacg | cctgttcgcg | aacaccaccg | ccaacttcac | gctcggtctg | 300 |
| ctcaactcga | cgatttccgc | taccgccgtg | cgctctcgg | tggtgttctt | ctcctcgctc | 360 |
| gccgggttct | ccctggccaa | gctgcgcttc | aagggccgca | acgtggccgc | ggtcggcgtt | 420 |
| gtgctgacca | tggccgtgcc | tgtgcagatg | ggaatcatcc | cgctgctgat | gctcatggag | 480 |
| tggttcggct | ggcgcggcca | gatcaccgcg | atcatcgtgc | ccttcatggt | cagcggcttc | 540 |
| ggcgtgttca | tgatgcgcca | gtactgcatc | caggcgatcc | ctgacgaact | gctggaagcg | 600 |
| gcgcgtatgg | acggctgctc | cacgttccgc | atctactgga | acgtggtcct | tcctgccctc | 660 |
| cgccctgcga | tggtggtgct | cggcctgctg | acgttcatga | cgcagtggaa | cgagttcacc | 720 |
| tgggcgctgg | cggtgctgac | tcccgccaac | ccgaccgtcc | agatcgccat | caaccagctc | 780 |
| aaccagtcgg | cgtactcgcg | tgacttcgcg | ctcatgttca | ccgggtccgt | cgtcgcaacc | 840 |
| ctcccccctgc | tcatcctgtt | cttcgtcctc | ggccgtcaac | tcatcggccg | gatcatggaa | 900 |
| ggtgccatta | agtga | | | | | 915 |

<210> SEQ ID NO 17
<211> LENGTH: 484
<212> TYPE: PRT
<213> ORGANISM: Thermobifida fusca

<400> SEQUENCE: 17

Met Thr Ser Gln Ser Thr Thr Pro Leu Gly Asn Leu Glu Glu Thr Pro
1               5                   10                  15

Lys Pro Asp Ile Arg Phe Pro Ser Asp Phe Val Trp Gly Val Ala Thr
            20                  25                  30

Ala Ser Phe Gln Ile Glu Gly Ser Thr Thr Ala Asp Gly Arg Gly Pro
        35                  40                  45

Ser Ile Trp Asp Thr Phe Cys Ala Thr Pro Gly Lys Val Glu Asn Gly
    50                  55                  60

Asp Thr Gly Asp Pro Ala Cys Asp His Tyr Asn Arg Tyr Arg Asp Asp
65                  70                  75                  80

Val Ala Leu Met Arg Glu Leu Gly Val Gly Ala Tyr Arg Phe Ser Ile
                85                  90                  95

Ala Trp Pro Arg Ile Gln Pro Glu Gly Lys Gly Thr Pro Val Glu Ala
            100                 105                 110

Gly Leu Asp Phe Tyr Asp Arg Leu Val Asp Cys Leu Leu Glu Ala Gly
        115                 120                 125

Ile Glu Pro Trp Pro Thr Leu Tyr His Trp Asp Leu Pro Gln Ala Leu
    130                 135                 140

Glu Asp Ala Gly Gly Trp Pro Asn Arg Asp Thr Ala Lys Arg Phe Ala

```
                    145                 150                 155                 160
Asp Tyr Ala Glu Ile Val Tyr Arg Arg Leu Gly Asp Arg Ile Thr Asn
                165                 170                 175

Trp Asn Thr Leu Asn Glu Pro Trp Cys Ser Ala Phe Leu Gly Tyr Ala
            180                 185                 190

Ser Gly Val His Ala Pro Gly Arg Gln Glu Pro Ala Ala Leu Ala
        195                 200                 205

Ala Ala His His Leu Met Leu Gly His Gly Leu Ala Ala Ala Val Met
    210                 215                 220

Arg Asp Leu Ala Gly Gln Ala Gly Arg Ser Val Arg Ile Gly Val Ala
225                 230                 235                 240

His Asn Gln Thr Thr Val Arg Pro Tyr Thr Asp Ser Glu Ala Asp Arg
                245                 250                 255

Asp Ala Ala Arg Arg Ile Asp Ala Leu Arg Asn Arg Ile Phe Thr Glu
            260                 265                 270

Pro Leu Val Lys Gly Arg Tyr Pro Glu Asp Leu Ile Glu Asp Val Ala
        275                 280                 285

Ala Val Thr Asp Tyr Ser Phe Val Gln Asp Gly Asp Leu Lys Thr Ile
    290                 295                 300

Ser Ala Asn Leu Asp Met Met Gly Val Asn Phe Tyr Asn Pro Ser Trp
305                 310                 315                 320

Val Ser Gly Asn Arg Glu Asn Gly Gly Ser Asp Arg Leu Pro Asp Glu
                325                 330                 335

Gly Tyr Ser Pro Ser Val Gly Ser Glu His Val Val Glu Val Asp Pro
            340                 345                 350

Gly Leu Pro Val Thr Ala Met Gly Trp Pro Ile Asp Pro Thr Gly Leu
        355                 360                 365

Tyr Asp Thr Leu Thr Arg Leu Ala Asn Asp Tyr Pro Gly Leu Pro Leu
    370                 375                 380

Tyr Ile Thr Glu Asn Gly Ala Ala Phe Glu Asp Lys Val Val Asp Gly
385                 390                 395                 400

Ala Val His Asp Thr Glu Arg Ile Ala Tyr Leu Asp Ser His Leu Arg
                405                 410                 415

Ala Ala His Ala Ala Ile Glu Ala Gly Val Pro Leu Lys Gly Tyr Phe
            420                 425                 430

Ala Trp Ser Phe Met Asp Asn Phe Glu Trp Ala Leu Gly Tyr Gly Lys
        435                 440                 445

Arg Phe Gly Ile Val His Val Asp Tyr Glu Ser Gln Thr Arg Thr Val
    450                 455                 460

Lys Asp Ser Gly Trp Trp Tyr Ser Arg Val Met Arg Asn Gly Gly Ile
465                 470                 475                 480

Phe Gly Gln Glu

<210> SEQ ID NO 18
<211> LENGTH: 1455
<212> TYPE: DNA
<213> ORGANISM: Thermobifida fusca

<400> SEQUENCE: 18
gtgacctcgc aatcgacgac tcctctgggc aatctcgagg agactcccaa accggatatc      60
cgcttcccgt ccgatttcgt gtggggagtg gcgaccgctt cgttccagat cgaaggctcc     120 accacgccg acgccgcgg ccccagcatc tgggacacct tctgcgccac tccgggcaag     180
gtcgagaacg gcgacacggg cgaccctgcc tgcgaccact acaaccggta ccgcgatgac     240
```

```
gtggccttga tgcgggagct gggcgtgggc gcctaccgct tctccatcgc ctggccgcgg    300
atccagcccg agggcaaggg cacgcccgtg gaggccgggc tggacttcta cgaccggctt    360
gtggactgcc tgctggaggc cggcatcgag ccgtggccga ccctctacca ctgggacctg    420
ccgcaggcgc tggaggacgc gggcggctgg cccaaccggg acacggccaa gcggttcgcc    480
gactacgcgg agatcgtcta ccgccggctc ggcgaccgga tcaccaactg aacacgctc    540 aacgagccgt ggtgctccgc gttcctgggc tacgcctccg gcgtgcacgc cccgggccgc    600
caggagccgg ctgctgcgct ggccgccgcc caccacctga tgctgggcca cgggctggcc    660
gctgccgtga tgcgggactt ggcgggccag gccggacgtt ccgtgcggat cggtgtcgcg    720
cacaaccaga ccacggtccg tccctacact gacagtgagg ccgaccggga cgctgcgcgc    780
cggattgacg ccctgcggaa ccgcatcttc accgagccgc tggtgaaggg ccgctacccg    840
gaggacctga tcgaggacgt cgccgcggtc accgactaca gcttcgtcca ggacggcgac    900
ctgaagacca tctccgccaa cctggacatg atgggcgtca acttctacaa cccgagctgg    960
gtgtcaggca accgggagaa cgggggctcc gaccggctgc ccgacgaggg ctactcgccg   1020
tcggtcggca gcgagcatgt cgtggaggtg accccggcc tgccggtgac cgccatgggc    1080
tggccgatcg acccgaccgg gctgtacgac acgctgaccc ggctggccaa cgactacccg   1140
ggcctgccgc tgtacatcac cgagaacggc gccgccttcg aggacaaggt ggtcgacggc    1200
gcggtgcacg acaccgagcg gatcgcctac ctggactcgc acctgcgggc cgcgcacgct   1260
gccattgagg cgggcgtgcc gctcaagggc tacttcgcct ggtcgttcat ggacaacttc   1320
gagtgggccc tcgggtacgg gaagcggttc ggcatcgtgc acgtggacta cgagagccag   1380
acgcgcacgg tgaaggacag cggctggtgg tactcccggg tgatgcgcaa cgggggaatc   1440
ttcggacagg aatag                                                    1455
```

<210> SEQ ID NO 19
<211> LENGTH: 3352
<212> TYPE: DNA
<213> ORGANISM: artificial
<220> FEATURE:
<223> OTHER INFORMATION: fusion construct

<400> SEQUENCE: 19

```
gtgactcttc ttaggcgtgg cgccgccccg cccggggaca aggaggcgac cagccttccc     60
cgacccggga acgacgccgt gacggagagg gagcgcaggc agatcttctg gacccgaatg    120
gatctgcggg tcaccccta tctgttcatc gcccccttct tcatcctgtt cgcgatcttc    180
ggcctgtttc cgctgctcta caccgtctgg gtgtcgctcc acgactggac gctgctcggc    240
ggaaaccagg ggttcaactg gttcgcgcac tacaccaggc tcgtccagga cgccaagttc    300
tggaactcgc tgtacaacac cttcggcatc ttcgtcgtcg cggttgttcc gcagctgctc    360
ctggccatgt acctggccga cacgctgagc cggaggatcc gcgcggtcaa cttcttccgc    420
atggggctcc tgctgcccta cctcacctcg atcgctgccg tggcgatcgt cttctcccag    480
ctgttcggta cccagttcgg tctcatcaac tacgtgctgg gcttcttcgg catcgacccg    540
atcaactggc aggcaggccg gttcctcctcg tgggtcgcga tcgcggtgat gatcgactgg    600
cgctggaccg gctacaacgc gctgatctac ctggcggcga tgtcggccat ccccggggag    660
atctacgagg ccgctgccat tgacggggcg tcgcgcatgc ggcagttctg gcagatcacc    720
atccccatgc tgcggcccac catcatcttc accgtcatcg tctccacgat cggccagatg    780
```

```
cagctcttca ctgagccggt catcttcggc gacgtggcgg gcggtactca aggacagttc    840
cagaccacga tgatgctgat cttcgaggag gcgttccgct caacaacta cgggtacggc     900
tccgcgatcg cctggacgct attcatgatc atcgtggtgc tcagcgcgct gaacgcgctg    960
ctcaccagca agatcaaggg ggcatgatgg ctgcgacttc gaccccgtct tctccgtctg   1020
tgtcggcagt cccccagtcc gcgaagaagc ggaagcggaa aaacggcggc agcatcggta   1080
tgcgggaggc gaccccgctc acctacatcg ggctgtccct caccatcctg ctgtcggtct   1140
tcccccctatg gtggatgttc gtcgtggcca gccgcgacac tgctgccgcc tcagcccgtc   1200
caccctacct gtggcccggc gggaatttcc tggaaaatct ggaacgcctg ttcgcgaaca   1260
ccaccgccaa cttcacgctc ggtctgctca actcgacgat ttccgctacc gccgtggcgc   1320
tctcggtggt gttcttctcc tcgctcgccg ggttctccct ggccaagctg cgcttcaagg   1380
gccgcaacgt ggccgcggtc ggcgttgtgc tgaccatggc cgtgcctgtg cagatgggaa   1440
tcatcccgct gctgatgctc atggagtggt tcggctggcg cggccagatc accgcgatca   1500
tcgtgcccttt catggtcagc ggcttcggcg tgttcatgat cgccagtac tgcatccagg   1560
cgatccctga cgaactgctg aagcggcgc gtatggacgg ctgctccacg ttccgcatct   1620
actgaacgt ggtccttcct gccctccgcc ctgcgatggg ggtgctcggc ctgctgacgt   1680
tcatgacgca gtggaacgag ttcacctggg cgctggcggt gctgactccc gccaacccga   1740
ccgtccagat cgccatcaac cagctcaacc agtcggcgta ctcgcgtgac ttcgcgctca   1800
tgttcaccgg gtccgtcgtc gcaaccctcc ccctgctcat cctgttcttc gtcctcggcc   1860
gtcaactcat cggccggatc atggaaggtg ccattaagtg acctcgcaat cgacgactcc   1920
tctgggcaat ctcgaggaga ctcccaaacc ggatatccgc ttcccgtccg atttcgtgtg   1980
gggagtggcg accgcttcgt tccagatcga aggctccacc acggccgacg gccgcggccc   2040
cagcatctgg gacaccttct gcgccactcc gggcaaggtc gagaacggcg acacgggcga   2100
ccctgcctgc gaccactaca accggtaccg cgatgacgtg gccttgatgc gggagctggg   2160
cgtgggcgcc taccgcttct ccatcgcctg gccgcggatc cagcccgagg caagggcac   2220
gcccgtggag gccgggctgg acttctacga ccggcttgtg gactgcctgc tggaggccgg   2280
catcgagccg tggccgaccc tctaccactg ggacctgccg caggcgctgg aggacgcggg   2340
cggctggccc aaccgggaca cggccaagcg gttcgccgac tacgcggaga tcgtctaccg   2400
ccggctcggc gaccggatca ccaactggaa cacgctcaac gagccgtggt gctccgcgtt   2460
cctgggctac gcctccggcg tgcacgcccc gggccgccag gagccggctg ctgcgctggc   2520
cgccgcccac cacctgatgc tgggccacgg gctggccgct gccgtgatgc gggacttggc   2580
gggccaggcc ggacgttccg tgcggatcgg tgtcgcgcac aaccagacca cggtccgtcc   2640
ctacactgac agtgaggccg accggacgc tgcgcgccgg attgacgccc tgcggaaccg   2700
catcttcacc gagccgctgg tgaagggccg ctaccggag gacctgatcg aggacgtcgc   2760
cgcggtcacc gactacagct tcgtccagga cggcgacctg aagaccatct ccgccaacct   2820
ggacatgatg ggcgtcaact tctacaaccc gagctgggtg tcaggcaacc gggagaacgg   2880
gggctccgac cggctgcccg acgagggcta ctcgccgtcg tcggcagcg agcatgtcgt   2940
ggaggtggac cccggcctgc cggtgaccgc catgggctgg ccgatcgacc cgaccgggct   3000
gtacgacacg ctgaccccggc tggccaacga ctacccgggc ctgccgctgt acatcaccga   3060
gaacggcgcc gccttcgagg acaaggtggt cgacggcgcg gtgcacgaca ccgagcgat   3120
cgcctacctg gactcgcacc tgcgggccgc gcacgctgcc attgaggcgg gcgtgccgct   3180
```

-continued caagggctac ttcgcctggt cgttcatgga caacttcgag tgggccctcg ggtacgggaa    3240
gcggttcggc atcgtgcacg tggactacga gagccagacg cgcacggtga aggacagcgg    3300
ctggtggtac tcccgggtga tgcgcaacgg gggaatcttc ggacaggaat ag            3352

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
gggagctcct tgatgtccac ccgcagaacc                                     30

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
tcaccacctg gcgttgcgcg cc                                             22

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22
aaagaattcg gaagaggacc ccatgctccg cc                                  32

<210> SEQ ID NO 23
<211> LENGTH: 34
<212> TYPE: DNA
<213> ORGANISM: Artificial Sequence
<220> FEATURE:
<223> OTHER INFORMATION: primer

<400> SEQUENCE: 23
aaagaattct cagccgcaga cctcaccgtt cacg                                34

<210> SEQ ID NO 24
<211> LENGTH: 41
<212> TYPE: DNA
<213> ORGANISM: Artificial Sequence
<220> FEATURE:
<223> OTHER INFORMATION: primer

<400> SEQUENCE: 24
aaatctagaa ggggagacag agtggtttct cgcaggtcat c                        41

<210> SEQ ID NO 25
<211> LENGTH: 39
<212> TYPE: DNA
<213> ORGANISM: Artificial Sequence
<220> FEATURE:
<223> OTHER INFORMATION: primer

<400> SEQUENCE: 25
aaatctagat cagctgcgcg gacgctgcac ggcgagctc                           39

<210> SEQ ID NO 26
<211> LENGTH: 43
<212> TYPE: DNA
<213> ORGANISM: Artificial Sequence
<220> FEATURE:
<223> OTHER INFORMATION: primer

<400> SEQUENCE: 26
aaagaattca aggaggagat caaatgccta ggaccacgcc cgc          43

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
atatgaattc tcagccgacc gtgcagggcg                         30

<210> SEQ ID NO 28
<211> LENGTH: 34
<212> TYPE: DNA
<213> ORGANISM: Artificial Sequence
<220> FEATURE:
<223> OTHER INFORMATION: primer

<400> SEQUENCE: 28
aaaggatccg gaggaccacg tgtccacact cggc                    34

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
aaatctagat cagccgagcg tgcaggc                            27

<210> SEQ ID NO 30
<211> LENGTH: 43
<212> TYPE: DNA
<213> ORGANISM: Artificial Sequence
<220> FEATURE:
<223> OTHER INFORMATION: primer

<400> SEQUENCE: 30
aaagagctcg gaagaggacc ccatgtcccc cagacctctt cgc          43

<210> SEQ ID NO 31
<211> LENGTH: 30
<212> TYPE: DNA
<213> ORGANISM: Artificial Sequence
<220> FEATURE:
<223> OTHER INFORMATION: primer

<400> SEQUENCE: 31
aaaggtacct cagctggcgg cgcaggtaag                         30

<210> SEQ ID NO 32
<211> LENGTH: 44
<212> TYPE: DNA
<213> ORGANISM: Artificial Sequence
<220> FEATURE:
<223> OTHER INFORMATION: primer

<400> SEQUENCE: 32
aaagaattcg gccgtcctct cttccatctg acatctgacc tctc        44

<210> SEQ ID NO 33
<211> LENGTH: 39
<212> TYPE: DNA
<213> ORGANISM: Artificial Sequence
<220> FEATURE:
<223> OTHER INFORMATION: primer

<400> SEQUENCE: 33
aaatctagag ccgccgggac ggcgagattt tgacctatc        39

<210> SEQ ID NO 34
<211> LENGTH: 48
<212> TYPE: DNA
<213> ORGANISM: Artificial Sequence
<220> FEATURE:
<223> OTHER INFORMATION: primer

<400> SEQUENCE: 34
aaagaattcg ggagctcctt gatggctccc ggctgccgcg tcgactac        48

<210> SEQ ID NO 35
<211> LENGTH: 41
<212> TYPE: DNA
<213> ORGANISM: Artificial Sequence
<220> FEATURE:
<223> OTHER INFORMATION: primer

<400> SEQUENCE: 35
aaaggatccg ggagctcctt gatggcactg acgtgcctgc t        41

<210> SEQ ID NO 36
<211> LENGTH: 33
<212> TYPE: DNA
<213> ORGANISM: Artificial Sequence
<220> FEATURE:
<223> OTHER INFORMATION: primer

<400> SEQUENCE: 36
aaatctagat catcgagtag ccgtacagct gcg        33

<210> SEQ ID NO 37
<211> LENGTH: 41
<212> TYPE: DNA
<213> ORGANISM: Artificial Sequence
<220> FEATURE:
<223> OTHER INFORMATION: primer

<400> SEQUENCE: 37
aaatctagag gaagaggacc ccatgagccg acctcaccac c        41

<210> SEQ ID NO 38
<211> LENGTH: 29
<212> TYPE: DNA
<213> ORGANISM: Artificial Sequence
<220> FEATURE:

<223> OTHER INFORMATION: primer

<400> SEQUENCE: 38
aaatctagac tagagctgtg cccgcggcc                                              29

<210> SEQ ID NO 39
<211> LENGTH: 49
<212> TYPE: DNA
<213> ORGANISM: Artificial Sequence
<220> FEATURE:
<223> OTHER INFORMATION: primer

<400> SEQUENCE: 39
aaagaattcg ggagctcctt gatggattta ttcggcaacc atccattaa                        49

<210> SEQ ID NO 40
<211> LENGTH: 39
<212> TYPE: DNA
<213> ORGANISM: Artificial Sequence
<220> FEATURE:
<223> OTHER INFORMATION: primer

<400> SEQUENCE: 40
aaggtacctt acagcaactc aaactcgcct ttcttaacg                                   39

<210> SEQ ID NO 41
<211> LENGTH: 53
<212> TYPE: DNA
<213> ORGANISM: Artificial Sequence
<220> FEATURE:
<223> OTHER INFORMATION: primer

<400> SEQUENCE: 41
aaatctagaa aagaattcgg ccgtcctctc ttccatctga catctgacct ctc                   53

<210> SEQ ID NO 42
<211> LENGTH: 39
<212> TYPE: DNA
<213> ORGANISM: Artificial Sequence
<220> FEATURE:
<223> OTHER INFORMATION: primer

<400> SEQUENCE: 42
aaactgcagg ccgccgggac ggcgagattt tgacctatc                                   39

<210> SEQ ID NO 43
<211> LENGTH: 34
<212> TYPE: DNA
<213> ORGANISM: Artificial Sequence
<220> FEATURE:
<223> OTHER INFORMATION: primer

<400> SEQUENCE: 43
aagaattcgg gaggtccttg atgtccaccc gcag                                        34

<210> SEQ ID NO 44
<211> LENGTH: 27
<212> TYPE: DNA
<213> ORGANISM: Artificial Sequence
<220> FEATURE:
<223> OTHER INFORMATION: primer

<400> SEQUENCE: 44
aagagctcac cacctggcgt tgcgcgc                                                27